(12) United States Patent
Naber et al.

(10) Patent No.: US 11,929,157 B2
(45) Date of Patent: Mar. 12, 2024

(54) TECHNIQUES FOR TRANSPORTING AUTONOMOUS PATIENT SUPPORT APPARATUSES AND MEDICAL EQUIPMENT TO AN INCIDENT SCENE

(71) Applicant: Stryker Corporation, Kalamazoo, MI (US)

(72) Inventors: Brandon David Naber, Portage, MI (US); Scott Zufall, Kalamazoo, MI (US); Jeffrey S. Dunfee, II, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 651 days.

(21) Appl. No.: 16/671,723

(22) Filed: Nov. 1, 2019

(65) Prior Publication Data

US 2020/0143927 A1 May 7, 2020

Related U.S. Application Data

(60) Provisional application No. 62/754,798, filed on Nov. 2, 2018, provisional application No. 62/754,836, filed
(Continued)

(51) Int. Cl.
*G16H 20/13* (2018.01)
*G05D 1/00* (2006.01)

(52) U.S. Cl.
CPC ........... *G16H 20/13* (2018.01); *G05D 1/0088* (2013.01); *G05D 2201/0206* (2013.01)

(58) Field of Classification Search
None
See application file for complete search history.

(56) References Cited

U.S. PATENT DOCUMENTS 8,439,416 B2   5/2013   Lambarth et al.
8,930,044 B1 *  1/2015   Peeters .................. B64C 19/00
                                                         709/201
(Continued)

FOREIGN PATENT DOCUMENTS

CN         106137570 A  * 11/2016
WO   WO-2018097574 A1 *  5/2018 .......... A47L 11/4011

*Primary Examiner* — Khoi H Tran
*Assistant Examiner* — Tristan J Greiner
(74) *Attorney, Agent, or Firm* — Howard & Howard Attorneys PLLC

(57) ABSTRACT

A method of transporting equipment modules to an incident scene with an comprises: determining an initial location of the incident scene; dispatching an ambulance loaded with the autonomous mobile response unit and a plurality of equipment modules to the initial location; determining a refined location of the incident scene; selecting a first equipment module; dispensing the first equipment module from the ambulance onto the autonomous mobile response unit; deploying the autonomous mobile response unit from the ambulance at the initial location; communicating the refined location of the incident scene to the autonomous mobile response unit; generating, with the navigation system, a drive path from the initial location to the refined location; and driving, with the drive system, the autonomous mobile response unit loaded with the first equipment module based on the drive path such that the autonomous mobile response unit travels from the initial location to the refined location.

18 Claims, 42 Drawing Sheets

Related U.S. Application Data on Nov. 2, 2018, provisional application No. 62/754,773, filed on Nov. 2, 2018.

(56) References Cited

U.S. PATENT DOCUMENTS

| | | |
|---|---|---|
| 8,948,935 B1 | 2/2015 | Peeters et al. |
| 9,051,043 B1 | 6/2015 | Peeters et al. |
| 9,307,383 B1* | 4/2016 | Patrick ................. B64C 39/024 |
| 9,994,315 B2 | 6/2018 | Walker et al. |
| 10,045,893 B2 | 8/2018 | Childs et al. |
| 2011/0277241 A1* | 11/2011 | Schejbal ................ A61G 7/018 |
| | | 5/510 |
| 2014/0076644 A1 | 3/2014 | Derenne et al. |
| 2014/0094997 A1* | 4/2014 | Hyde .................. G05D 1/0246 |
| | | 348/148 |
| 2014/0150806 A1* | 6/2014 | Hu ........................ B25J 11/009 |
| | | 901/1 |
| 2016/0000617 A1* | 1/2016 | Magill .................... A61G 1/04 |
| | | 296/20 |
| 2016/0367415 A1 | 12/2016 | Hayes et al. |
| 2017/0371353 A1* | 12/2017 | Millinger, III ....... G05D 1/0094 |
| 2018/0303689 A1 | 10/2018 | Souke et al. |
| 2019/0047462 A1* | 2/2019 | Vijayaraghavan .... B64C 39/024 |
| 2019/0130770 A1* | 5/2019 | Di Benedetto ....... B64C 39/024 |
| 2019/0320867 A1* | 10/2019 | Noh ........................ B25J 19/02 |

* cited by examiner

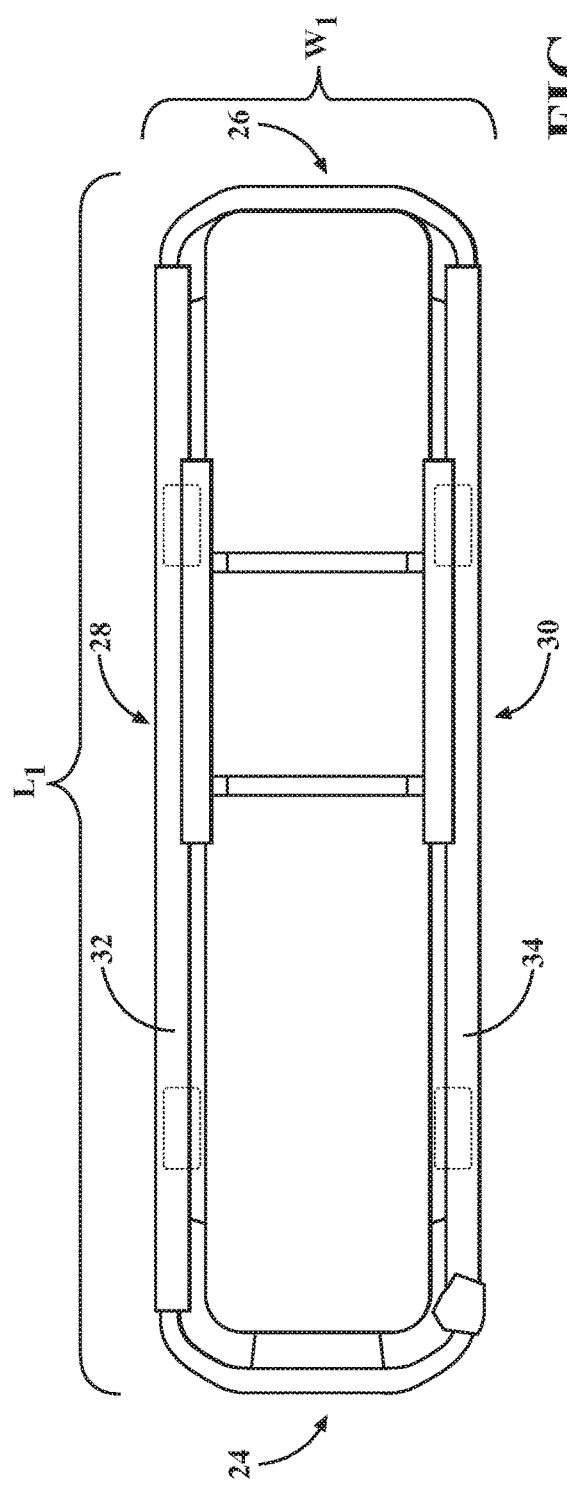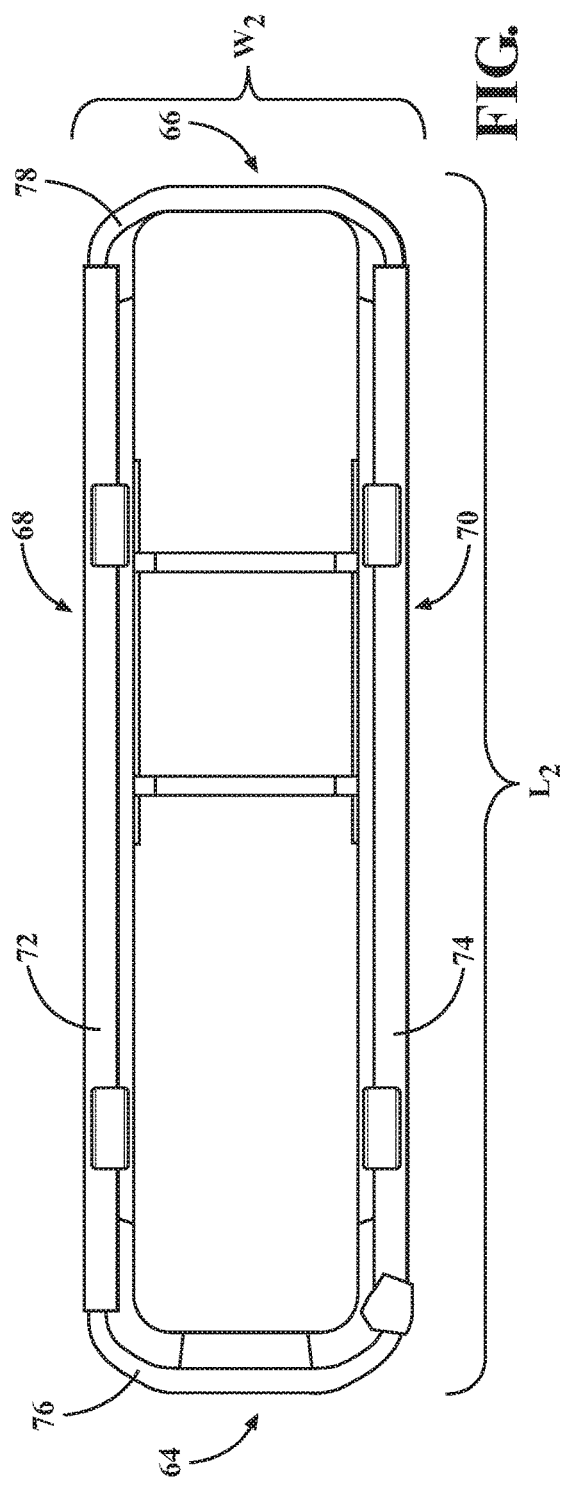

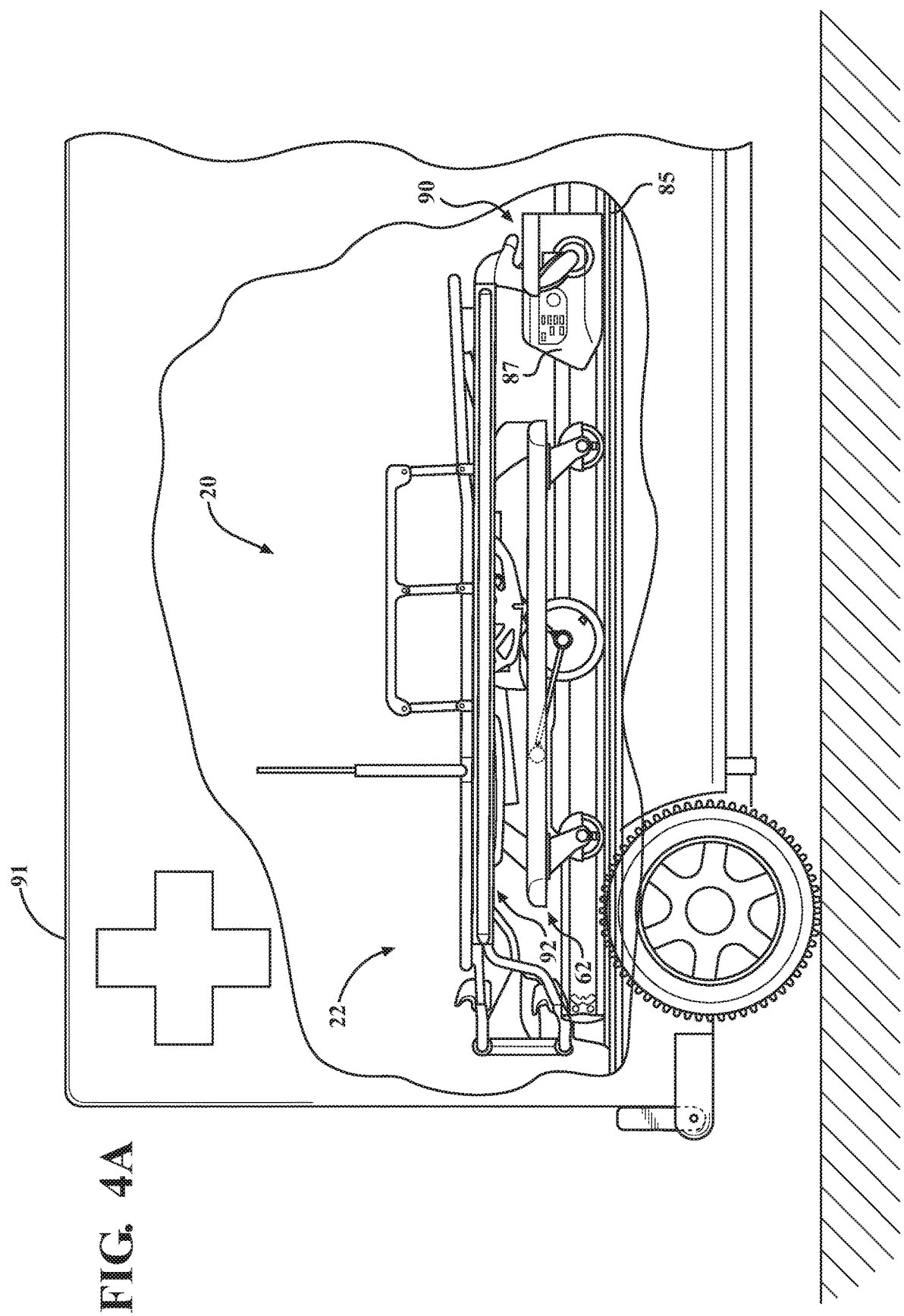

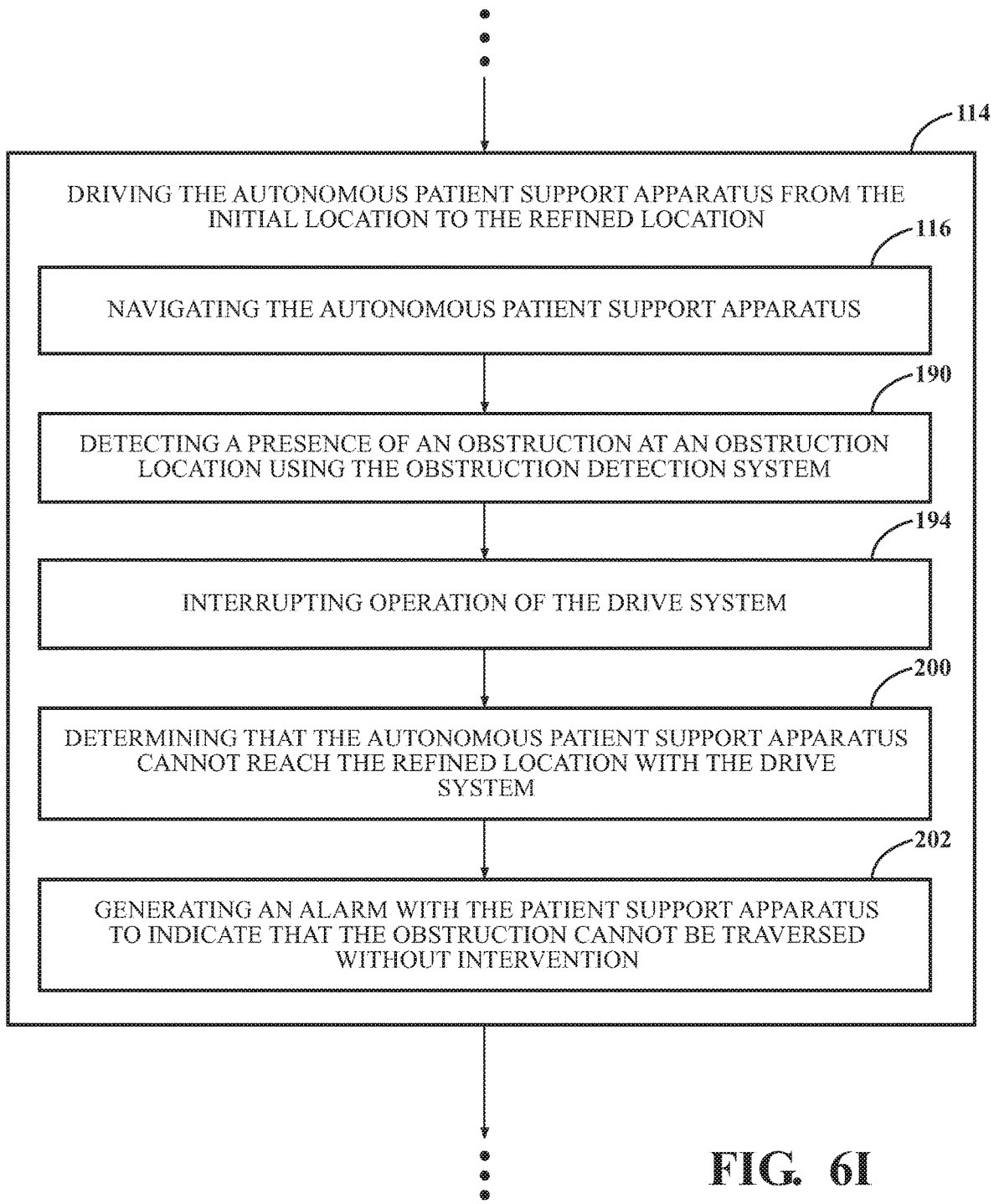

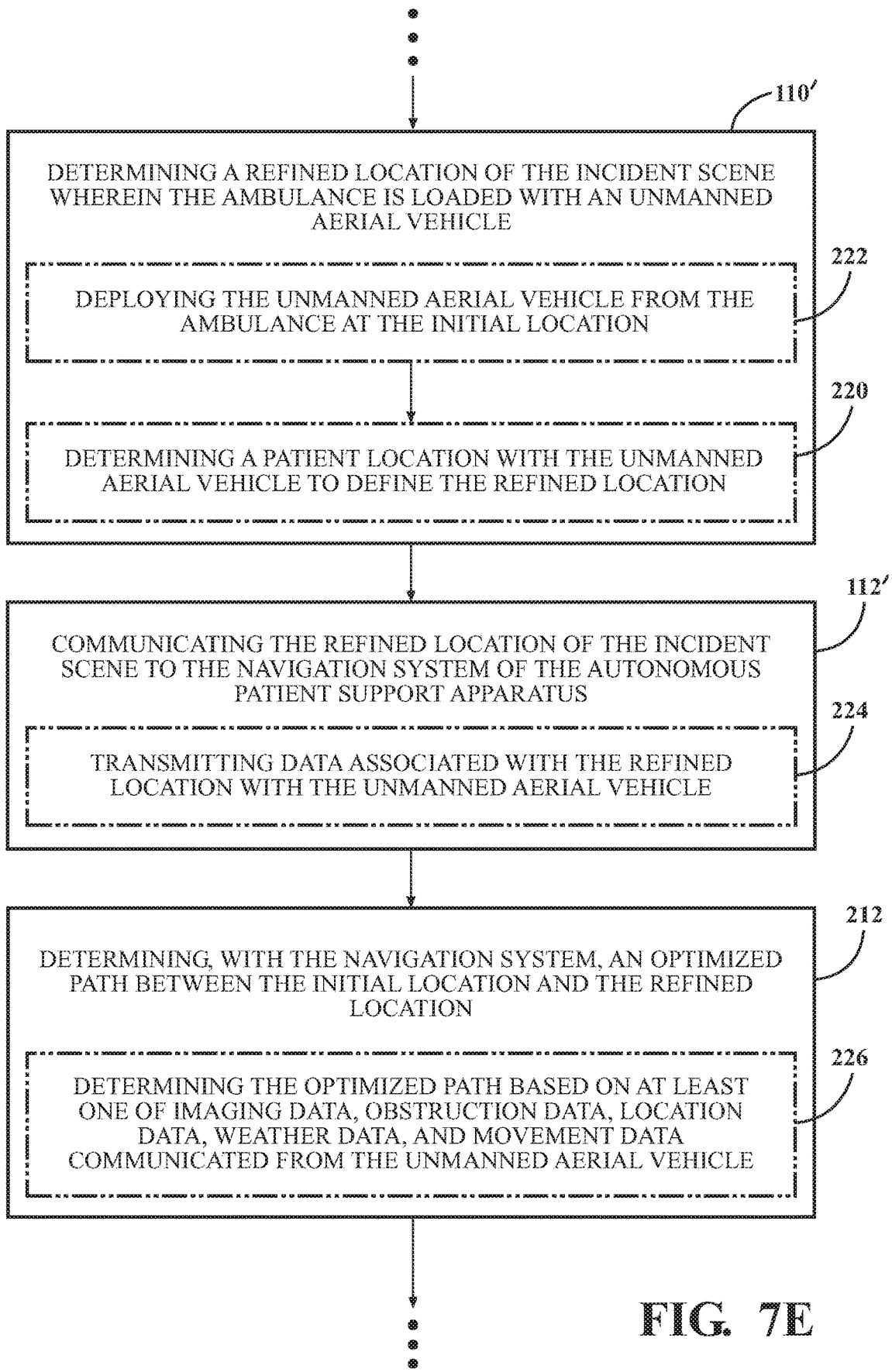

TECHNIQUES FOR TRANSPORTING AUTONOMOUS PATIENT SUPPORT APPARATUSES AND MEDICAL EQUIPMENT TO AN INCIDENT SCENE

CROSS-REFERENCE TO RELATED APPLICATIONS

The subject patent application claims priority to and all the benefits of: U.S. Provisional Patent Application No. 62/754,773 filed on Nov. 2, 2018; U.S. Provisional Patent Application No. 62/754,798 filed on Nov. 2, 2018; and U.S. Provisional Patent Application No. 62/754,836 filed on Nov. 2, 2018; the disclosures of each of which are hereby incorporated by reference in their entirety.

BACKGROUND

When an emergency occurs at an incident scene, service entities such as fire departments typically dispatch a variety of assets, such as an ambulance or other vehicles loaded with a patient support apparatus, a trauma kit, a drug box, an $O_2$ bottle, a defibrillator, and/or a heart monitor, as well as personnel, such as a first responder, an emergency medical technician (EMT), a firefighter, and/or a police officer, to a location near the incident scene. In some situations, the incident scene is a location the dispatched assets and personnel may reach directly. For example, if the incident scene is a place of residence or a public building, the dispatched assets and personnel may be dispatched to an address associated with the place of residence or public building.

Sometimes, however, the incident scene is a location that may be difficult to reach for dispatched assets and personnel. For example, the incident scene may be a backyard of a place of residence, a location along a hiking trail, or a disaster zone. In such situations, the service entity may be required to dispatch multiple personnel to efficiently and successfully locate the incident scene and subsequently treat one or more patients involved in the emergency. For example, one first responder may locate the incident scene and another first responder may subsequently receive the location of the incident scene before transporting medical supplies to the incident scene. There remains a need in the art for dispatching personnel and/or equipment to incident scenes with improved accuracy and efficiency.

BRIEF DESCRIPTION OF THE DRAWINGS

Advantages of the present disclosure will be readily appreciated as the same becomes better understood by reference to the following detailed description when considered in connection with the accompanying drawings.

FIG. 2A is a top view of the autonomous patient support apparatus of FIG. 1.

FIG. 2B is a bottom view of the autonomous patient support apparatus of FIG. 1.

FIGS. 4A-4C are side views of the patient transport apparatus of FIG. 1 being unloaded from an emergency response vehicle.

FIGS. 6B-6J are diagrammatic views of embodiments of the method of transporting the autonomous patient support apparatus to the incident scene.

DETAILED DESCRIPTION

Herein, an autonomous mobile response unit is described. The autonomous mobile response unit may include an autonomous patient support apparatus 20, as shown in FIGS. 1-4C. The autonomous patient support apparatus 20 may be configured to support and autonomously transport a patient and/or a medical equipment module in a health care or emergency response setting. The autonomous patient support apparatus 20 illustrated in FIGS. 1-4C includes a cot. In other embodiments, however, the autonomous patient support apparatus 20 may include an autonomous hospital bed, stretcher, table, wheelchair, chair, or similar apparatus utilized in the autonomous transportation and care of a patient.

Figure 1:
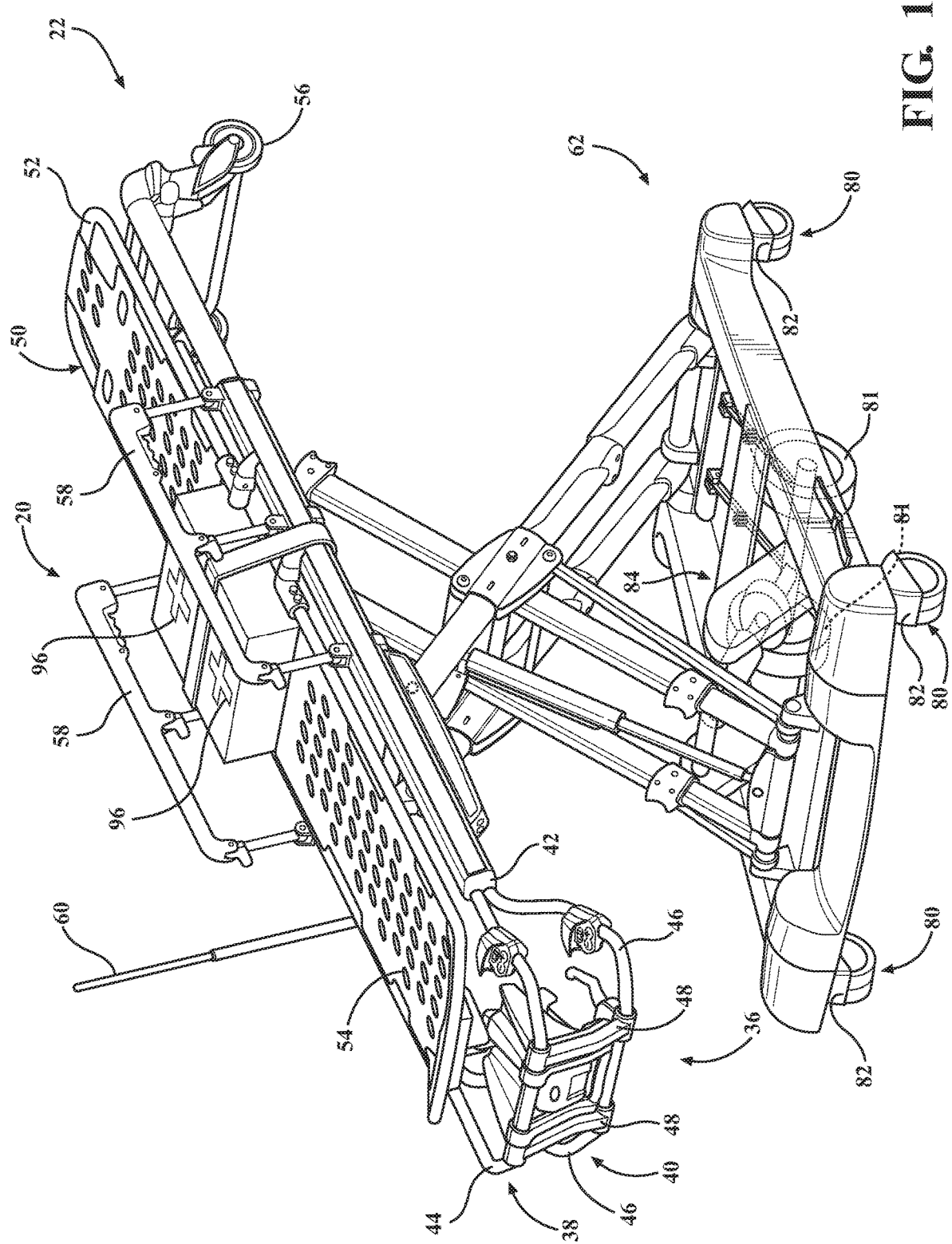
FIG. 1 is a perspective view of an autonomous patient support apparatus.

As shown in FIG. 1, the autonomous patient support apparatus 20 includes a support frame 22 configured to support a patient. The support frame 22 can be like that shown in U.S. Patent Application Publication No. 2018/0303689A1, which claims priority to U.S. Provisional Patent App. No. 62/488,441, filed on Apr. 21, 2017, entitled "Emergency Cot With A Litter Height Adjustment Mechanism," the disclosures of which are hereby incorporated by reference in their entirety.

The support frame 22 is further illustrated from a top view of the autonomous patient support apparatus 20 in FIG. 2A. As shown in FIG. 2A, the support frame 22 has a length $L_1$ defined extending longitudinally, and a width $W_1$ defined extending laterally, which is smaller than the length $L_1$. The support frame 22 may include two opposing lateral sides 24, 26 extending along the width $W_1$ coupled to two opposing end sides 28, 30 extending along the length $L_1$.

The support frame 22 may have various configurations and may include a variety of components. For example, in FIG. 1, end sides 28, 30 of the support frame 22 include hollow side rails 32, 34 (side rail 32 shown in FIG. 2A). In the example of FIG. 1, side 24 of the autonomous patient support apparatus 20 includes a foot end handle 36, which may include a pair of vertically spaced U-shaped frame members 38 and 40. The frame members 38, 40 may be joined together by frame brackets 42 (only one frame bracket 42 is shown in FIG. 1), which may be telescopingly affixed inside side rails 32, 34, as illustrated in FIG. 1. A fastener or pin (not illustrated) may be utilized to facilitate a connection of the frame brackets 42 to the interior of each of the respective side rails 32, 34. Furthermore, as shown, frame member 40 may diverge from frame member 38, providing pairs of vertically spaced hand grip areas 44, 46 on frame members 38, 40, respectively. Additionally, spacer brackets 48 may be connected to opposing portions of each of the frame members 38 and 40 to maintain the vertical spacing between the hand grip areas 44 and 46.

The support frame 22 may be coupled to a variety of components that aid in supporting and/or transporting the patient. For example, in FIG. 1, the support frame 22 is coupled to a patient support surface 50, upon which the patient directly rests. The patient support surface 50 may be defined by one or more articulable deck sections, for example, a back section 52 and a foot section 54, to facilitate care and/or transportation of the patient in various patient positions.

The support frame 22 may also be coupled to loading wheels 56. As shown in FIG. 1, the loading wheels 56 may extend from the support frame 22 proximal to the back section 52 of the patient support surface 50 and may facilitate loading and unloading of the autonomous patient support apparatus 20 from a vehicle. In one example, the loading wheels 56 may be positioned and configured to facilitate loading and unloading the autonomous patient support apparatus 20 into or from an ambulance.

The support frame 22 may also be coupled to hand rails 58. In FIG. 1, the hand rails 58 extend from opposing sides of the support frame 22 and provide egress barriers for the patient on the patient support surface 50. The hand rails 58 may also be utilized by an individual, such as a caregiver, an emergency medical technician (EMT), or another medical professional, to move or manipulate the autonomous patient support apparatus 20 manually. In some embodiments, the hand rails 58 may include a hinge, pivot or similar mechanism to allow the hand rails 58 to be folded or stored adjacent to or below the patient support surface 50. The support frame 22 may also be coupled to a vertical support member 60. The vertical support member 60 may be configured to hold a medical device or medication delivery system, such as a bag of fluid to be administered via an IV. The vertical support member 60 may also be configured for the operator of the autonomous patient support apparatus 20 to push or pull on the vertical support member 60 to manipulate or move the autonomous patient support apparatus 20.

The autonomous patient support apparatus 20 may include a base 62. As shown in FIG. 2B, the base 62 has a length $L_2$ defined longitudinally, and a width $W_2$, which is smaller than the length $L_2$. The base 62 may include two opposing lateral base sides 64, 66 extending along the width $W_2$ coupled to two opposing longitudinal base sides 68, 70 extending along the length $L_2$. As shown in FIG. 1, the longitudinal base sides 68, 70 may include longitudinally-extending rails 72, 74 and the lateral base sides 64, 66 may include crosswise-extending rails 76, 78 which may be coupled at the ends thereof to the rails 72, 74.

The base 62 may further include a plurality of caster wheel assemblies 80 operatively connected adjacent to each corner of the base 62 defined by the longitudinally-extending rails 72, 74 and the crosswise-extending rails 76, 78. As such, the autonomous patient support apparatus 20 of FIG. 1 may include four caster wheel assemblies 80. The wheel assemblies 80 may be configured to swivel to facilitate turning of the autonomous patient support apparatus 20. The wheel assemblies 80 may include a swivel locking mechanism to prevent the wheel assemblies 80 from swiveling when engaged. The wheel assemblies 80 may also include wheel brakes 82 to prevent rotation of the wheel.

The base 62 may also include at least one auxiliary wheel 81. The auxiliary wheel 81 may be configured to swivel to steer the autonomous patient support apparatus 20. In instances where the base 62 includes more than one auxiliary wheel 81, the auxiliary wheels 81 may be configured to swivel about their own, separate swivel axes, or a common swivel axis in order to steer the autonomous patient support apparatus 20. Additionally, in some instances, the auxiliary wheel may be deployed from the base 62 in a deployed position or stowed within the base 62 in a stowed position. The auxiliary wheels 81 can be like that shown in U.S. Pat. No. 10,045,893, which claims priority to U.S. Provisional Patent App. No. 62/270,704, filed on Dec. 22, 2015, entitled "Patient Transport Apparatus With Controllable Auxiliary Wheel Assembly," the disclosures of which are hereby incorporated by reference in their entirety.

Figure 3:
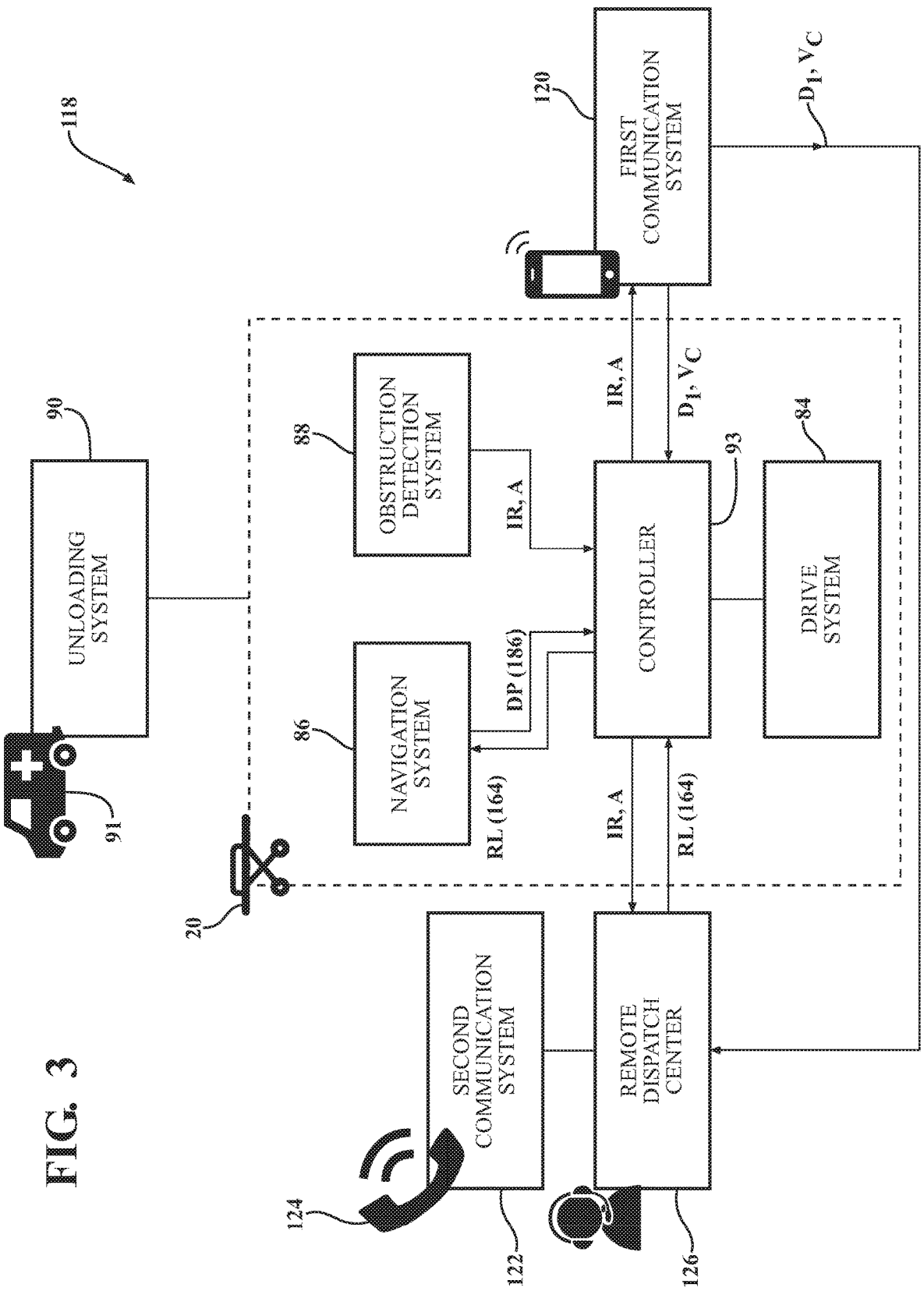
FIG. 3 is a schematic view of a system for transporting the autonomous patient support apparatus to an incident scene.

Referring to FIGS. 1 and 3, the autonomous patient support apparatus 20 may include a drive system 84 configured to drive the autonomous patient support apparatus 20 by driving the at least one auxiliary wheel 81. As shown in the embodiment of FIG. 1, the drive system 84 may be coupled to the at least one auxiliary wheel 81. The drive system 84 may be configured to drive the patient support apparatus 20 by driving, steering, deploying, and/or stowing the at least one auxiliary wheel 81. In some instances, the drive system 84 may also be configured to move the auxiliary wheel 81 between the deployed position and the stowed position. The drive system 84 may include an electric actuator, a hydraulic actuator, and/or a pneumatic actuator. The drive system 84 may also include rotary actuators, linear actuators, or any other suitable actuators for moving the at least one auxiliary wheel 81. Additionally, the drive system 84 may include reversible, DC motors, or other types of motors. The drive system 84 can be like that shown in U.S. Patent Application Publication No. 2016/0367415A1, which claims priority to U.S. Provisional Patent App. No. 62/184,911, filed on Jun. 22, 2015, entitled "Patient Support Apparatuses With Navigation And Guidance Systems," the disclosures of which are hereby incorporated by reference in their entirety.

As shown in FIG. 3, the autonomous patient support apparatus 20 may include a navigation system 86 configured to generate a drive path (shown as "DP (186)" in FIG. 3) for the autonomous patient support apparatus 20. The navigation system 86 may include a variety of sensors that provide a variety of inputs, which the navigation system 86 may use to generate the drive path 186. For example, the navigation system 86 may include an accelerometer for detecting accelerations of the autonomous patient support apparatus 20, including both the magnitude and direction of the accelerations. The navigation system 86 may also include a magnetometer for detecting a geographical orientation of the autonomous patient support apparatus 20 with respect to the Earth's magnetic field. A wheel counting sensor may also, or alternatively, be included that detects revolutions of at least one of the caster wheel assemblies 80 and/or auxiliary wheels 81. Still further, the navigation system 86 may include an altimeter adapted to detect an elevation of the autonomous patient support apparatus 20. In this way, the navigation system 86 can be like the navigation system shown in U.S. Patent Application Publication No. 2016/0367415A1.

Additionally, the navigation system 86 may generate the drive path 186 for the autonomous patient support apparatus 20 based on the variety of sensors. For example, the navigation system 86 may generate the drive path 186 based on a location and an acceleration of the autonomous patient support apparatus 20 received from the accelerometer and the magnetometer. Furthermore, the navigation system 86 may generate the drive path 186 prior to or concurrent with the autonomous patient support apparatus 20 being driven by the drive system 84.

Referring to FIG. 3, the autonomous patient support apparatus 20 may also include an obstruction detection system 88 configured to detect a presence of an obstruction. An obstruction may be defined as an object preventing, or that will prevent, the drive system 84 from driving the autonomous patient support apparatus 20 along the drive path 186 generated by the navigation system 86. As such, the obstruction detection system 88 may include a variety of sensors, such as an impact sensor, a proximity sensor, and/or a wheel position sensor configured to detect the presence of an obstruction. For example, an impact sensor, such as a strain gauge, may detect a force applied to a component, such as a wheel assembly 80, an auxiliary wheel 81, or the base 62 of the autonomous patient support apparatus 20, which may indicate the presence of an obstruction. In another example, a proximity sensor may use sonar, LiDAR, or imaging technology to determine a proximity of an obstruction. For instance, the proximity sensor may be a camera configured to capture an image, which the obstruction detection system 88 may process to determine the presence of an obstruction. In yet another example, the obstruction detection system 88 may include wheel position sensors configured to detect an actual speed of the autonomous patient support apparatus 20. The obstruction detection system 88 may then compare the actual speed to a commanded speed to determine the presence of an obstruction. The obstruction detection system 88 can be like the object/landmark detection system shown in U.S. Patent Application Publication No. 2016/0367415A1.

Also shown in FIG. 3, the autonomous patient support apparatus 20 may include a controller 93 configured to control the drive system 84 based on the drive path 186 generated by the navigation system 86. As such, the controller 93 may be coupled to the navigation system 86 and to the drive system 84, as shown in FIG. 3. Furthermore, the controller 93 may serve as a hub, allowing for communication between the drive system 84, the navigation system 86, and the obstruction detection system 88. For example, the controller 93 may be coupled to the obstruction detection system 88, which allows the obstruction detection system 88 to communicate a presence of an obstruction to the navigation system 86 via the controller 93. Additionally, the controller 93 may allow the drive system 84, the navigation system 86, and the obstruction detection system 88 to communicate with a first communication system 120 (described in further detail below), a remote dispatch center 126 (described in further detail below), and an unmanned aerial vehicle 94 (described in further detail below). The controller 93 can be like the controller shown in U.S. Patent Application Publication No. 2016/0367415A1.

Figure 4B:
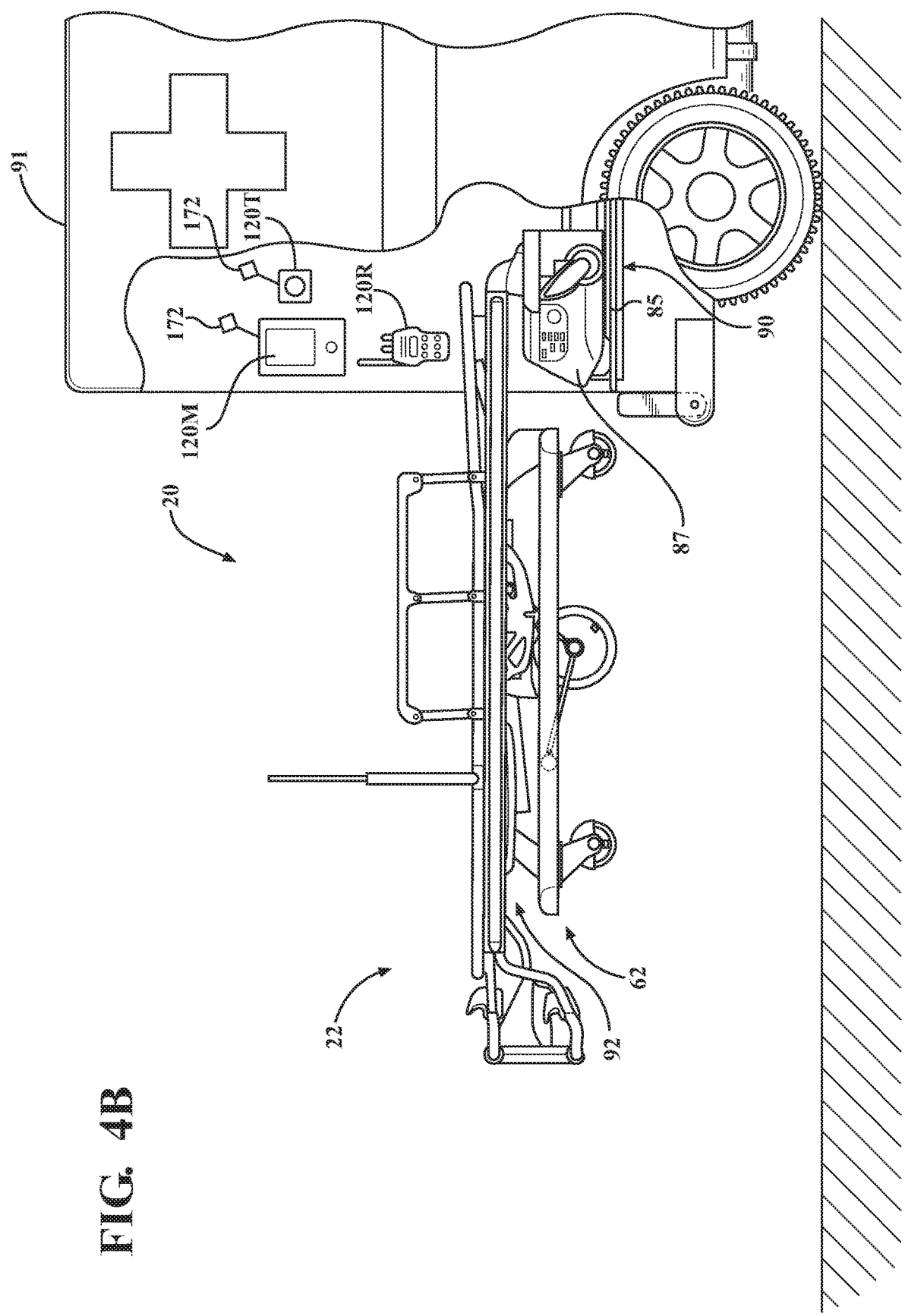
Figure 4C:
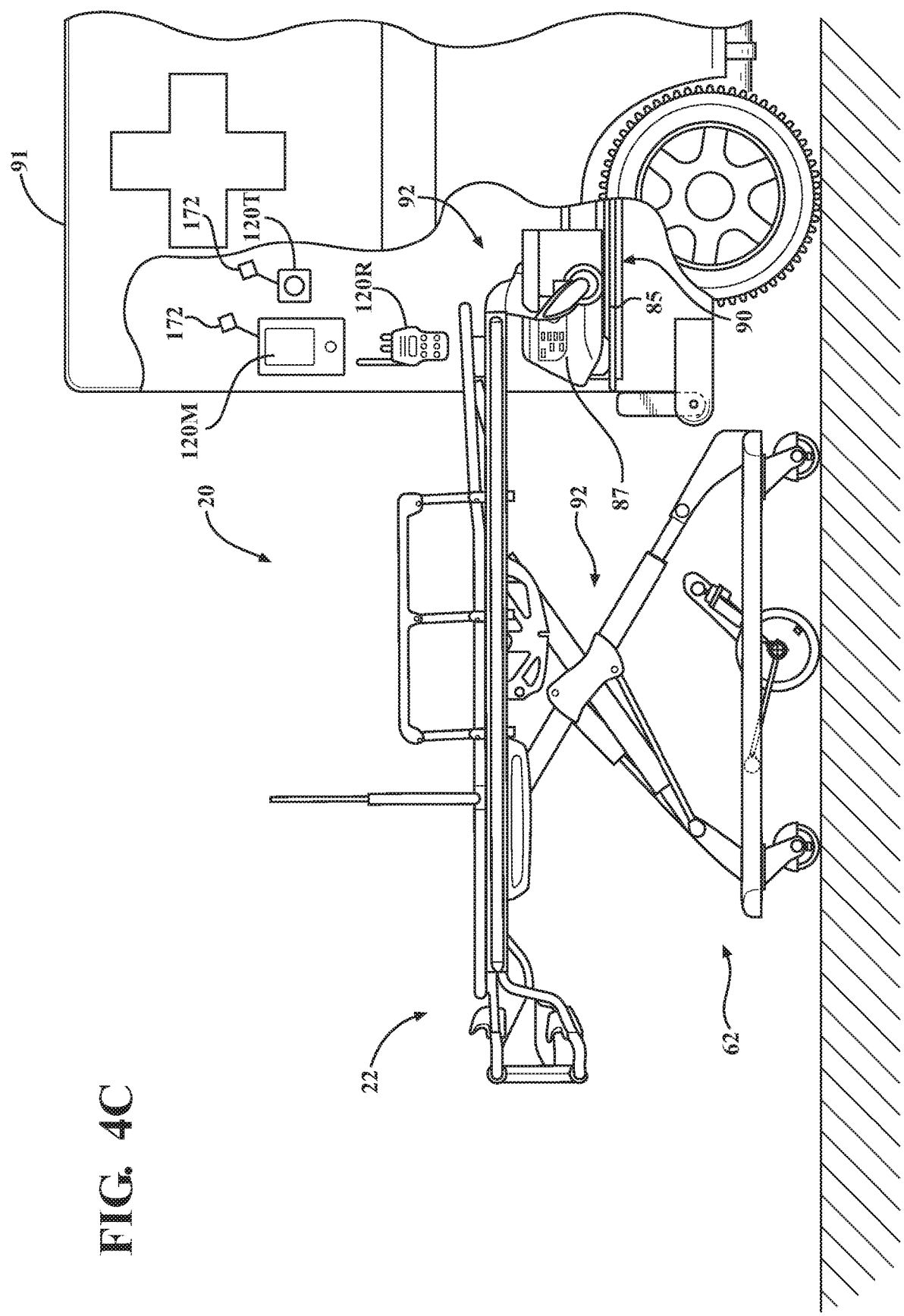

The autonomous patient support apparatus 20 may be loaded in an ambulance 91. Furthermore, as shown in FIG. 3, the ambulance 91 loaded with the autonomous patient support apparatus 20 may include an unloading system 90 for unloading the autonomous patient support apparatus 20 from an ambulance 91. An operation of the unloading system 90 is shown in FIGS. 4A-4C. As shown in FIGS. 4A-4C, the autonomous patient support apparatus 20 may be coupled to a trolley 87 and a track 85 of the unloading system 90. The trolley 87 may then move along the track 85 such that the autonomous patient support apparatus 20 may be positioned within the ambulance 91 (as shown in FIG. 4A) and unloaded from the ambulance (as shown in FIGS. 4B and 4C). The unloading system 90, the trolley 87, and the track 85 can be like the unloading apparatus, the trolley, and the track shown in U.S. Pat. No. 8,439,416, which claims priority to U.S. Provisional Patent App. No. 61/248,374, filed on Oct. 2, 2009, entitled "Ambulance Cot and Loading and Unloading System," the disclosures of which are hereby incorporated by reference in their entirety.

The unloading system 90 may also include a lift mechanism 92, which may be configured to move between a plurality of vertical configurations including a retracted configuration, as shown in FIGS. 4A and 4B, and an extended configuration, as shown in FIG. 4C. The lift mechanism 92 may be configured to facilitate movement of the support frame 22 relative to the base 62. When the autonomous patient support apparatus 20 is being unloaded from the ambulance 91, the lift mechanism 92 moves from the retracted configuration to the extended configuration by moving the base 62. When the autonomous patient support apparatus 20 has been unloaded from the ambulance 91, the lift mechanism 92 can be utilized to move from the extended configuration back to the retracted configuration, or to other configurations therebetween, to position the support frame 22 closer to the base 62. The lift mechanism 92 can be like that shown in the U.S. Patent Application Publication No. 2018/0303689A1.

The unloading system 90 may be operated manually or autonomously. For example, a first responder may manually operate the unloading system 90 when unloading the autonomous patient support apparatus 20 from the ambulance 91. In another instance, the first responder may operate the unloading system 90 by physically depressing a button to activate the unloading system 90. In yet another instance, the unloading system 90 may unload the autonomous patient support apparatus 20 autonomously after the ambulance 91 reaches a location or after receiving an input from a remote computing device.

Figure 5:
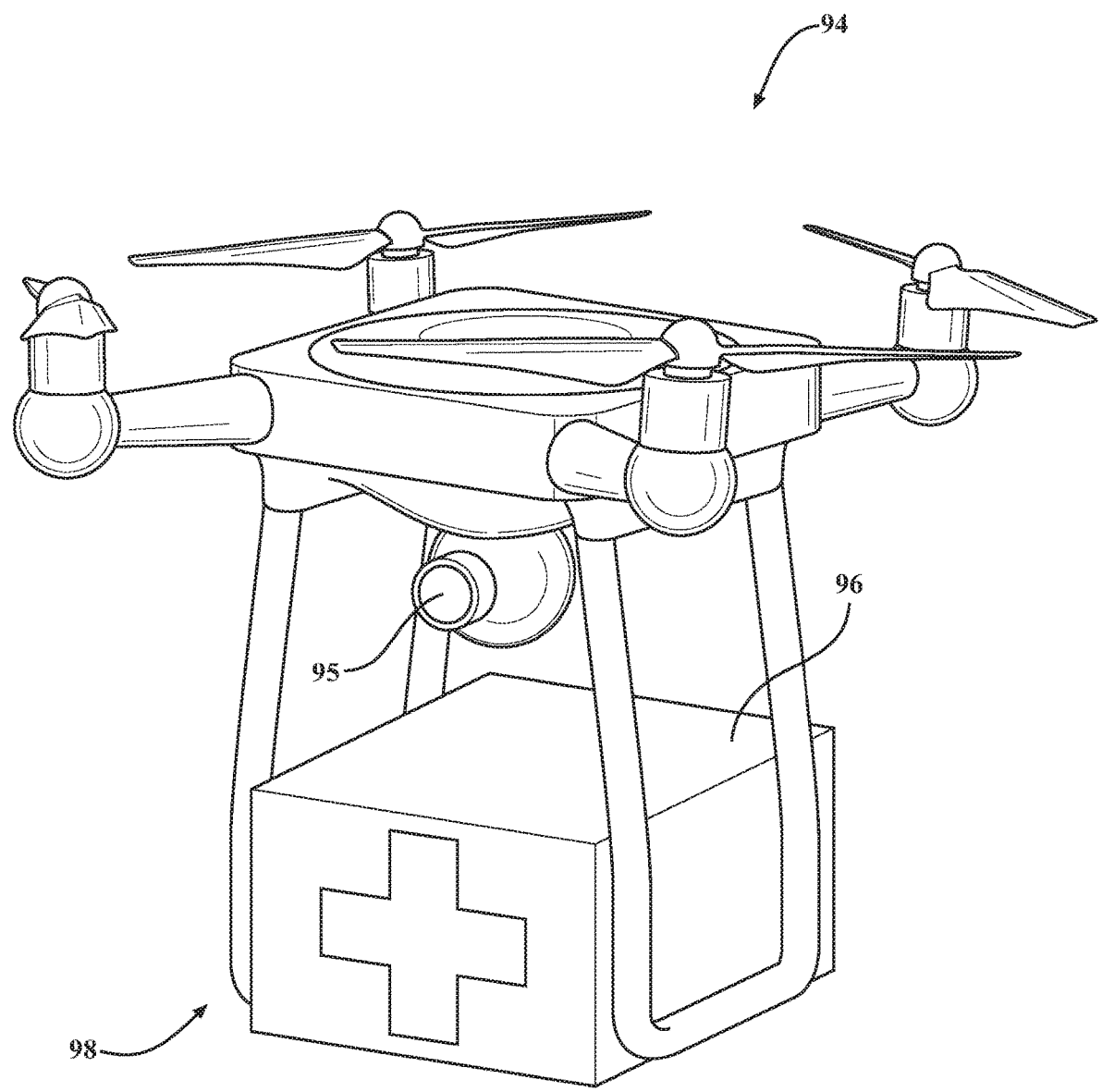
FIG. 5 is a perspective view of an unmanned aerial vehicle.

The autonomous mobile response unit may also include the unmanned aerial vehicle 94, as shown in FIG. 5. The unmanned aerial vehicle 94 may be configured to autonomously transport a medical equipment module 96 to an incident scene, from the ambulance 91 or from another location, in a health care or emergency response setting. The unmanned aerial vehicle 94 shown in FIG. 5 is realized as a multirotor drone; however, the unmanned aerial vehicle 94 may comprise a fixed wing drone or a single rotor drone, or a wheeled vehicle in some embodiments. Additionally, the unmanned aerial vehicle 94 may also include the navigation system 86, the drive system 84, the controller 93, and the obstruction detection system 88.

Furthermore, the unmanned aerial vehicle 94 may include a variety of sensors. For example, the unmanned aerial vehicle 94 may include a variety of imaging sensors, location sensors, and environmental sensors, which may be used to collect imaging data, obstruction data, topographical data, location data, movement data, and weather data. In one example, the unmanned aerial vehicle 94 may include a camera 95, as shown in FIG. 5. The camera 95 may collect imaging data, which may be used to determine a presence of an obstruction, topographical data, and a location of the incident scene.

As shown in FIGS. 1 and 5, the autonomous mobile response unit, realized as the autonomous patient support apparatus 20 in FIG. 1 and the unmanned aerial vehicle 94 in FIG. 5, may be configured to transport a medical equipment module 96. For example, in FIG. 1, the medical equipment module 96 is disposed on and affixed to the patient support surface 50 while being transported by the autonomous patient support apparatus 20. In FIG. 5, a retaining system 98 of the unmanned aerial vehicle 94 retains the medical equipment module 96 while the unmanned aerial vehicle 94 transports the medical equipment module 96, and can be released automatically or manually. In other instances, alternative mechanisms may be employed for transporting the medical equipment module 96. For example, the autonomous patient support apparatus 20 may include a dedicated compartment for housing the medical equipment module 96 during transport. As another example, the retaining system 98 of the unmanned aerial vehicle 94 may include a variety of components, such as a crate, a rope, adhesive, or any other components suitable for retaining and transporting the medical equipment module 96.

Figure 6A:
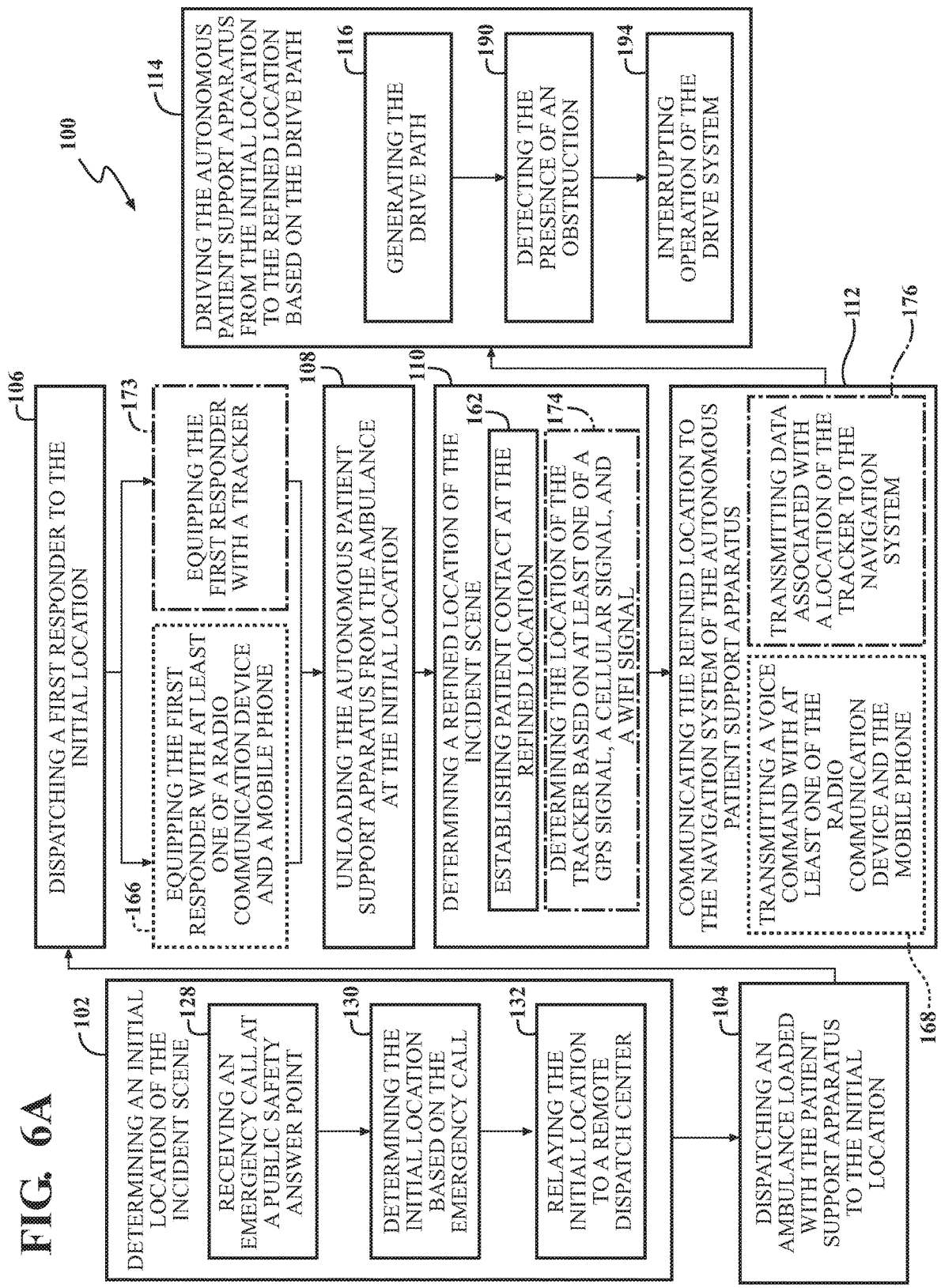
FIG. 6A is a diagrammatic view of a method of transporting the autonomous patient support apparatus to the incident scene.

A method 100 of transporting an autonomous patient support apparatus, such as the above-described autonomous patient support apparatus 20, to an incident scene is represented as a flow chart in FIG. 6A. As shown, the method 100 includes a step 102 of determining an initial location of the incident scene; a step 104 of dispatching an ambulance (such as the above-described ambulance 91) loaded with an autonomous patient support apparatus (such as the above-described autonomous patient support apparatus 20) to the initial location; a step 106 of dispatching a first responder to the initial location; a step 108 of unloading the autonomous patient support apparatus 20 from the ambulance 91 at the initial location; a step 110 of determining a refined location of the incident scene; a step 112 of communicating the refined location of the incident scene to the navigation system 86 of the autonomous patient support apparatus 20; a step 114 of driving, with the drive system 84, the autonomous patient support apparatus 20 based on a drive path 186 such that the autonomous patient support apparatus 20 travels from the ambulance 91 to the refined location; and a step 116 of generating, with the navigation system 86, the drive path 186 from the initial location to the refined location.

The steps of the method 100, and the steps of any other method described herein, may be ordered differently in some embodiments. For example, the step 104 of dispatching an ambulance 91 to the initial location may occur after the step 106 of dispatching a first responder to the initial location. As another example, the step 116 of generating the drive path 186 may occur prior to the step 114 of driving the drive system 84. In such an example, the navigation system 86 may generate the drive path 186 and provide the drive system 84 with the drive path 186, which the drive system 84 subsequently follows to drive the autonomous patient support apparatus 20 during step 114.

Additionally, the steps of the method 100 may include other steps. For instance, referring to the embodiment of FIG. 6A, the step 114 of driving the autonomous patient support apparatus 20 may also include the step 116 of generating the drive path 186. In such an embodiment, the navigation system 86 may be configured to generate the drive path 186 while the drive system 84 is driving the autonomous patient support apparatus 20. As such, the navigation system 86 may generate the drive path 186 based on inputs received while the drive system 84 is driving. Similarly, the steps of any other method described herein may include other steps of the method illustrated in FIG. 6A. For example, in any method described herein, any step of generating a drive path 186 may be included in any step of driving an autonomous mobile response unit, such as the autonomous patient support apparatus 20 or the unmanned aerial vehicle 94.

Referring back to FIG. 3, the steps 102-116 of the method 100 may be executed by components of a system 118 configured to facilitate transporting the autonomous patient support apparatus 20 to the incident scene. As shown, the system 118 includes the unloading system 90 of the ambulance 91, the autonomous patient support apparatus 20, as well as the navigation system 86, drive system 84, obstruction detection system 88, and controller 93. The system 118 also includes a first communication system 120 in communication with the navigation system 86 of the autonomous patient support apparatus 20, a second communication system 122 corresponding to a public safety answering point 124, and a remote dispatch center 126 in communication with the navigation system 86 and the obstruction detection system 88 of the autonomous patient support apparatus 20. In some embodiments, certain components of the system 118 may be omitted.

As shown in FIG. 6A, the step 102 of determining the initial location of the incident scene may include a step 128 of receiving an emergency call at the public safety answering point 124; a step 130 of determining the initial location based on the emergency call; and a step 132 of relaying the initial location from the public safety answering point 124 to the remote dispatch center 126 in communication with the navigation system 86 of the autonomous patient support apparatus 20. Once the initial location is determined during step 102, the method proceeds to steps 104 and 106 of dispatching the ambulance 91 loaded with the autonomous patient support apparatus 20 and the first responder to the initial location.

Figure 6B:
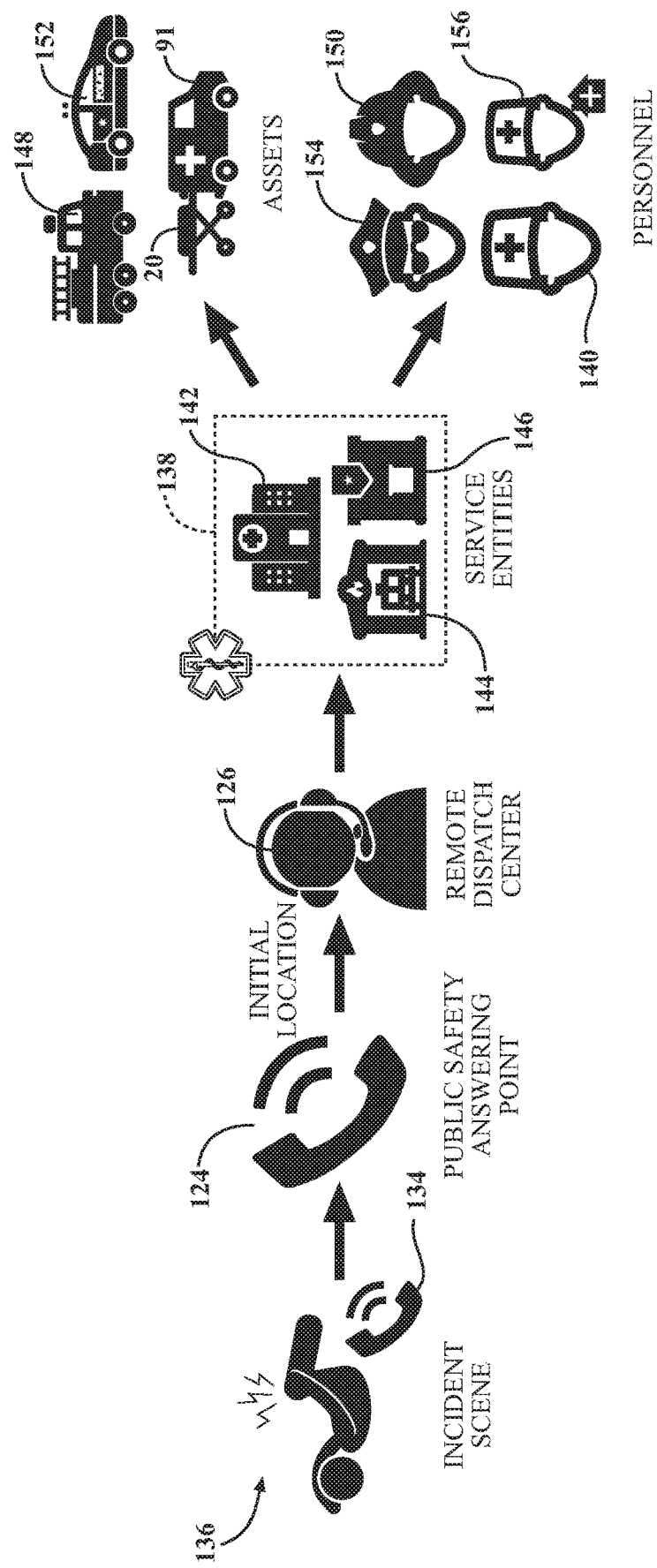

Additional aspects of step 102 of the method 100, including additional steps 128, 130, and 132, are illustrated in FIG. 6B. As shown, the public safety answering point 124 receives an emergency call 134 from an incident scene 136. For example, in some instances, a call-taker operating the second communication system 122, such as a landline telephone system, at the public safety answering point 124 may receive the emergency call 134 from someone "dialing 9-1-1" or another emergency telephone number. In such instances, after the call-taker receives the emergency call 134, the call-taker may begin collecting information regarding the incident scene 136, such as what type of emergency has occurred at the incident scene 136, an approximate location of the incident scene 136, and/or a nearby address of the incident scene 136. In this way, the call-taker may determine the initial location during step 130 based on the approximate location of the emergency. For example, the call-taker may determine an address and/or GPS coordinates of the initial location during step 130 based on the approximate location of the emergency. The call-taker then relays the initial location and any other information regarding the incident scene to the remote dispatch center 126 during step 132. In some instances, the call-taker routes the emergency call to the remote dispatch center 126 via the second communication system 122 and the remote dispatch center 126 continues collecting information regarding the incident scene.

Steps 104 and 106 are also illustrated in FIG. 6B. As shown, the remote dispatch center 126 may communicate with a service entity 138 to dispatch the ambulance 91 loaded with the autonomous patient support apparatus 20 to the incident scene 136 during step 104. Also shown, the remote dispatch center 126 may communicate with the service entity 138 to dispatch the first responder 140 to the incident scene 136 during step 106.

As shown in FIG. 6B, the service entity 138 may comprise one or more of a variety of different types, such as a hospital 142, a fire department 144, a police station 146, or any other suitable type of service entity. Additionally, in various instances, the service entity 138 may have access to or may otherwise comprise a variety of different types of assets, which may be positioned at a physical location, such as at a station or department associated with a service entity 138. The service entity 138 may also communicate with a variety of personnel, who may be "on duty" at a station or department associated with a service entity 138, or may be "off duty" but nevertheless may dispatch or otherwise respond from their place of residence or another location. In one instance, the remote dispatch center 126 may communicate with the fire department 144 to dispatch the ambulance 91, a fire truck 148, a firefighter 150, and the first responder 140 to the incident scene 136. In another instance, the remote dispatch center 126 may communicate with the police station 146 to dispatch the ambulance 91, a police vehicle 150, and a police officer 154 to the incident scene 136. In yet another instance, the remote dispatch center 126 may communicate with the hospital 142 to dispatch the ambulance 91, and a first responder 156 responding from their place of residence. It will be appreciated that the forgoing examples are illustrative and non-limiting. Other instances, including dispatching various types of assets and/or personnel from various locations and/or types of service entities, are contemplated.

Figure 6C:
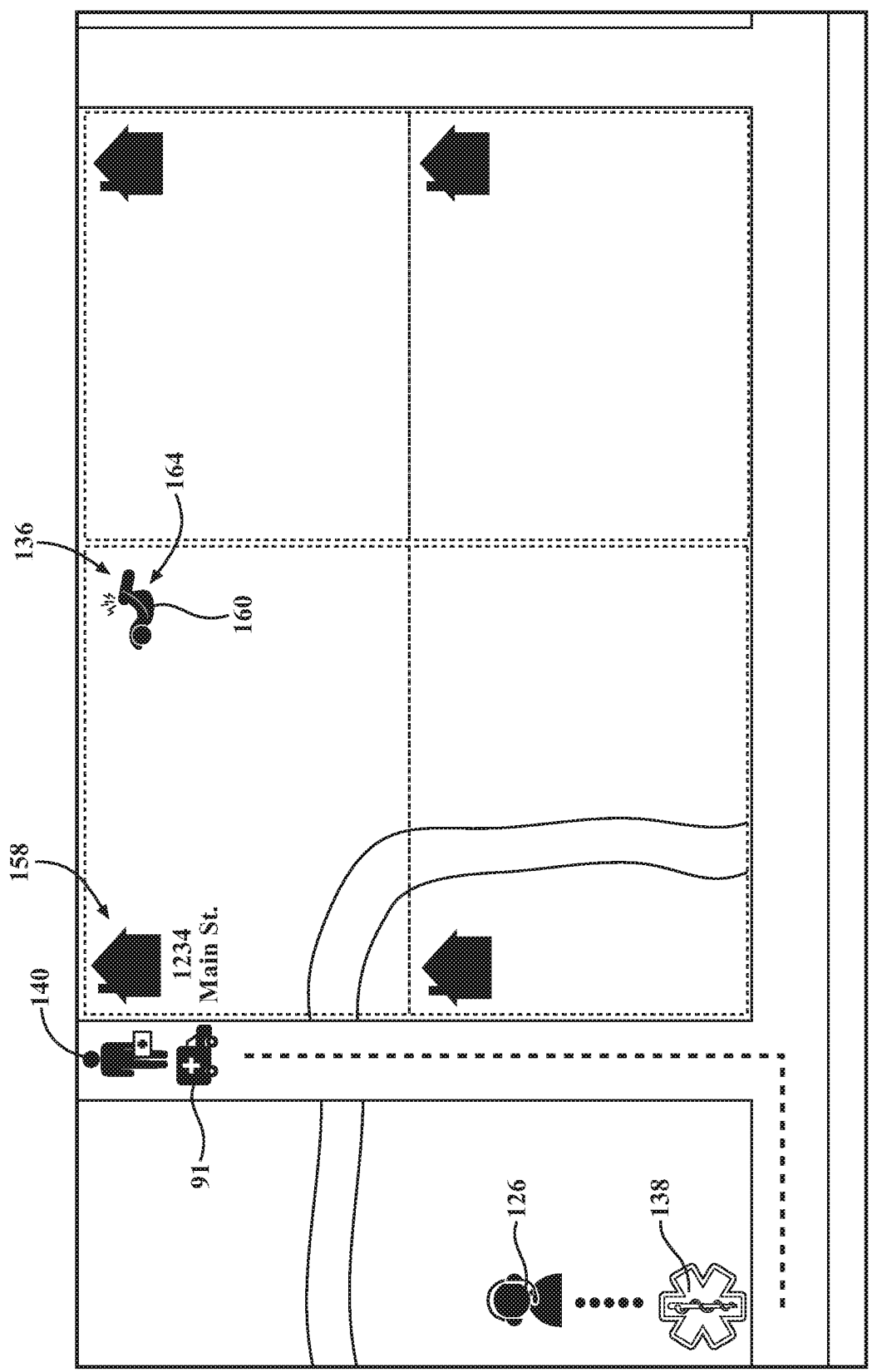

Aspects of steps 104 and 106 are illustrated in FIG. 6C. As shown in this illustrative instance, the remote dispatch center 126 communicates with the service entity 138 to dispatch the ambulance 91 loaded with the autonomous patient support apparatus 20 and the first responder 140 to the initial location 158 of the incident scene 136. In the embodiment of FIG. 6C, four homes are shown, each of which include a respective property area illustrated by dotted lines. In this illustrative instance, the incident scene 136 corresponds to a leg injury to a patient 160 located within a property area of a home with an address of 1234 Main St. As such, the initial location 158 corresponds to the home and the ambulance 91 and the first responder 140 are dispatched to the associated address, 1234 Main St.

Referring back to FIG. 6A, after steps 104 and 106, the method 100 proceeds to the step 108 of unloading the autonomous patient support apparatus 20 from the ambulance 91 at the initial location 158. As previously stated, the autonomous patient support apparatus 20 may be unloaded from the ambulance 91 by the unloading system 90. Here, the unloading system 90 may be manually operated by the first responder 140, or the unloading system 90 may autonomously unload the autonomous patient support apparatus 20 after the ambulance 91 reaches the initial location 158. In still other instances, the unloading system 90 may unload the autonomous patient support apparatus 20 after the unloading system 90 is manually activated by the first responder 140 or remotely activated by the remote dispatch center 126.

The method 100 also includes the step 110 of determining the refined location of the incident scene 136, which may include a step 162 of establishing patient contact at the refined location 164 with the first responder 140. Referring to FIG. 6C, in this illustrative instance, the refined location 164 of the incident scene 136 corresponds to a location suitable for treating the patient 160. For example, in FIG. 6C, the refined location 164 corresponds to a location within the property area of 1234 Main St. where the patient 160 was found by the first responder 140. In some embodiments, step 110 includes the step 162 of establishing contact between the patient 160 at the refined location 164 and the first responder 140. In such an embodiment, the first responder 140 may travel from the initial location 158 while searching for the patient 160 within the property area. Here, establishing contact with the patient 160 when found by the first responder 140 would then define the refined location 164.

The method also includes the step 112 of communicating the refined location 164 of the incident scene 136 to the navigation system 86 of the autonomous patient support apparatus 20. In some instances, the first communication system 120 may be configured to communicate the refined location 164 to the navigation system 86 during step 112. For example, in some embodiments, the method 100 may include a step 166 of equipping the first responder 140 with at least one of a radio communication device and a mobile phone. In such embodiments, the first communication system 120 includes the radio communication device and/or the mobile phone. As shown in FIG. 4B, the radio communication device 120R and the mobile phone 120M may be affixed to the ambulance 91, allowing the first responder 140 to equip the radio communication device 120R and/or the mobile phone 120M upon reaching the initial location 158. Additionally, in such embodiments, step 112 may include a step 168 of transmitting a voice command VC (shown in FIG. 3) with the radio communication device 120R and/or the mobile phone 120M to communicate the refined location 164 to the navigation system 86. For example, the voice command VC may include a description of the refined location 164 from the first responder 140. The radio communication device 120R and/or the mobile phone 120M may transmit the voice command VC to communicate the refined location 164 of the incident scene 136 to the navigation system 86.

In some embodiments, such as the embodiment of FIG. 3, the radio communication device 120R and/or the mobile phone 120M may transmit the voice command VC to the remote dispatch center 126 to communicate the refined location 164 (shown as "RL (164)" in FIG. 3) to the navigation system 86. In such embodiments, the remote dispatch center 126 may process the voice command VC to determine the refined location 164. The remote dispatch center 126 may then transmit the refined location 164 to the navigation system 86. For example, in the embodiment of FIG. 3, the remote dispatch center 126 transmits the refined location 164 to the navigation system 86 via the controller 93.

In embodiments where the method 100 includes the steps 166 and 168, the method 100 may not necessarily include the step 162 of establishing patient contact at the refined location 164. In some instances, the first responder 140 may transmit the voice command VC during step 168 without establishing patient contact at the refined location 164. In one such instance, the refined location 164 may be a location that the autonomous patient support apparatus 20 could reach, but the first responder 140 is unable to reach. As such, the first responder 140 may transmit a voice command VC describing the refined location 164 to communicate the refined location 164 to the navigation system 86. In this way, the autonomous patient support apparatus 20 may reach the patient 160 even if the first responder 140 is not able to.

Figure 6D:
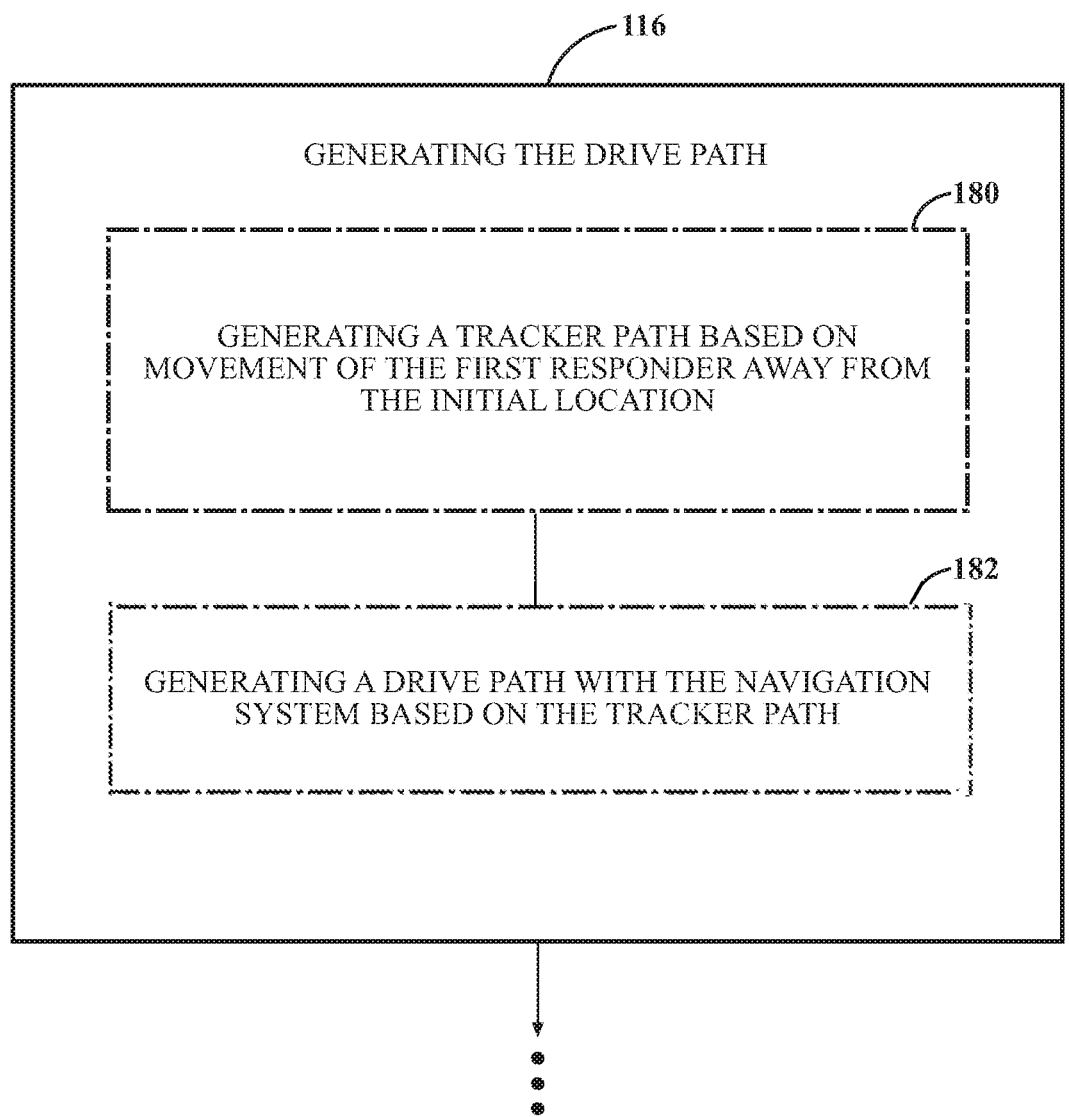
Figure 6E:
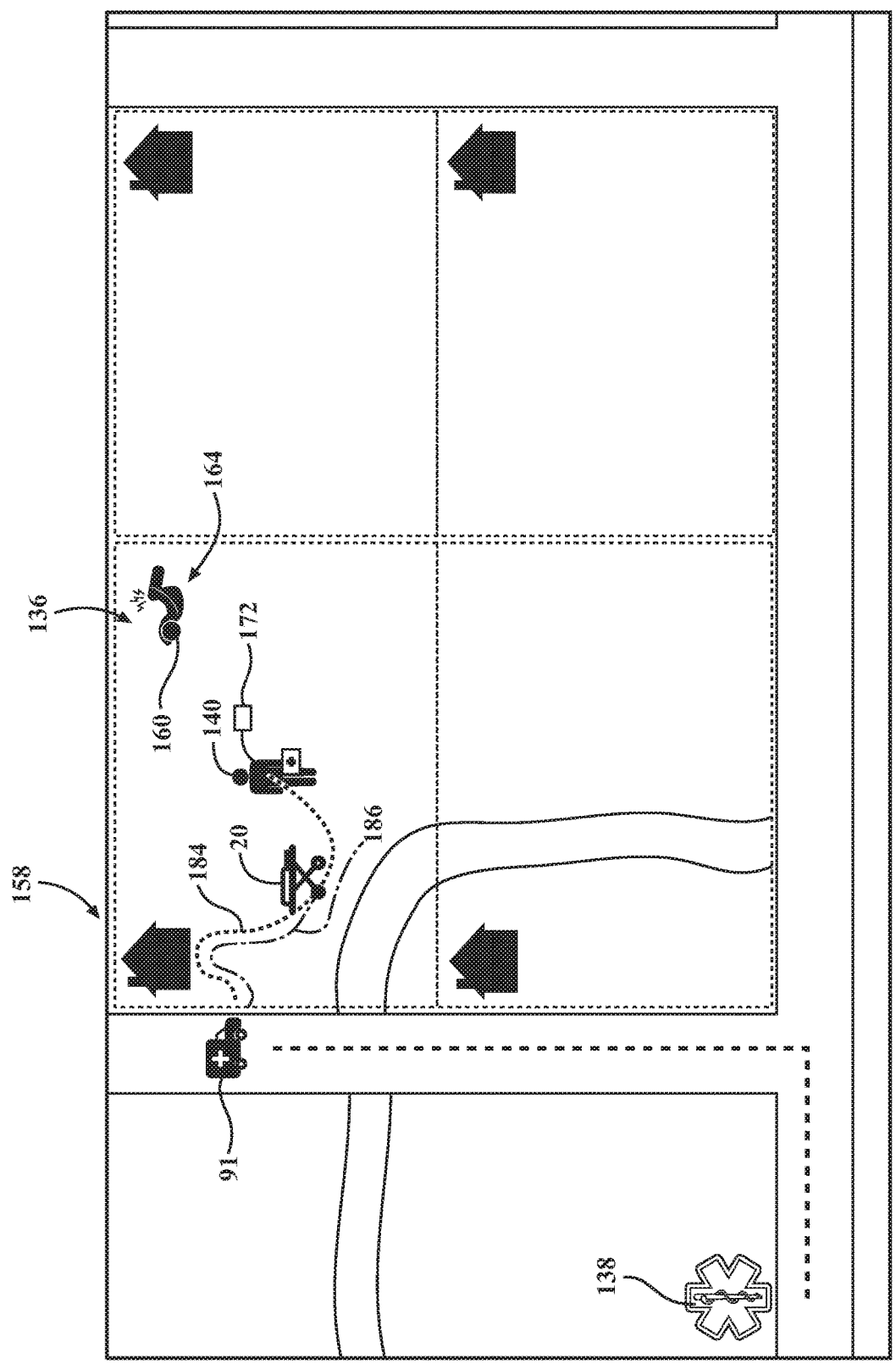
Figure 6F:
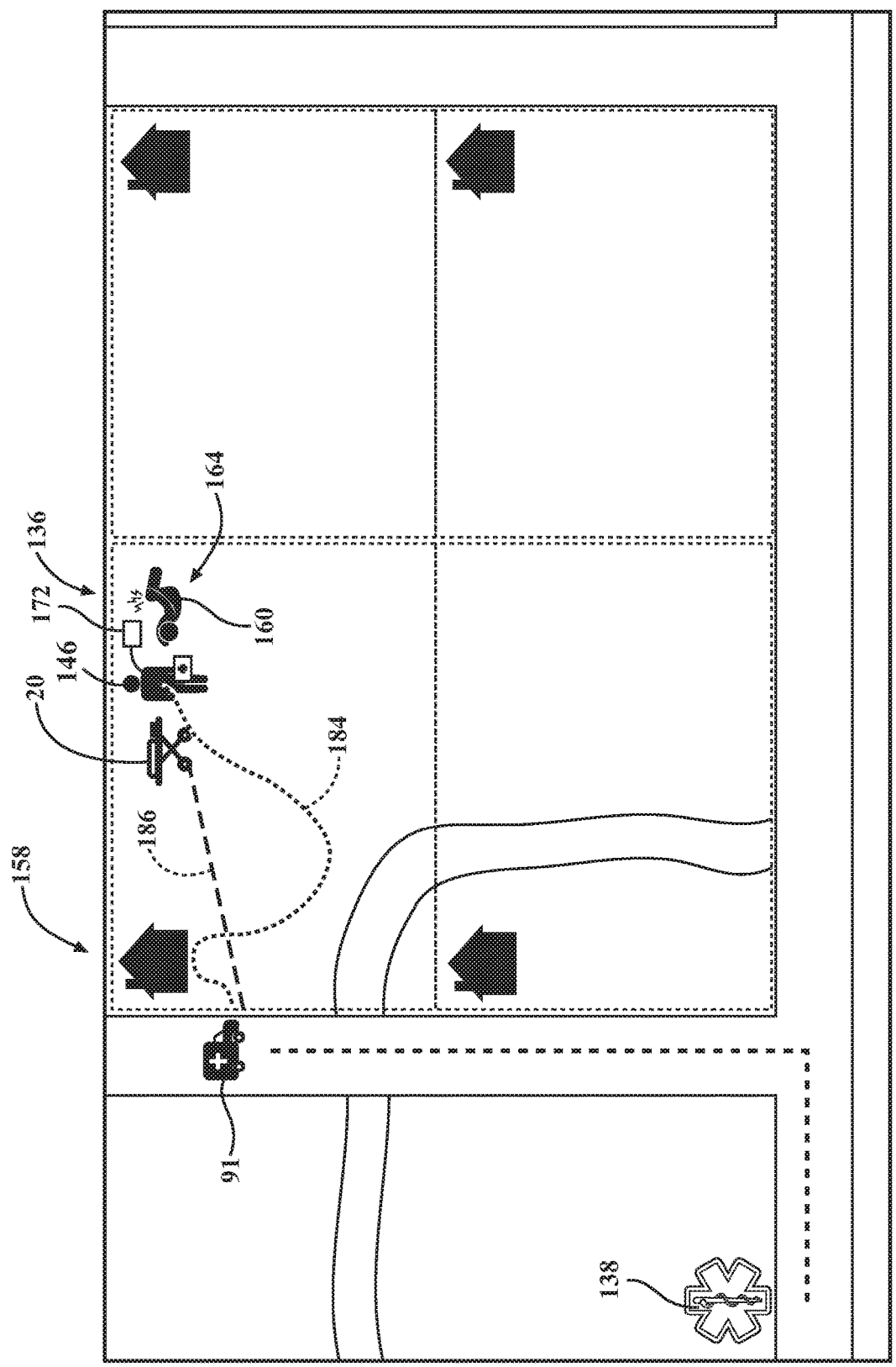

The method 100 may include a step 173 of equipping the first responder 140 with a tracker 172, which is shown in FIGS. 6E and 6F. In such embodiments, the method may include the above-described step 162 of establishing patient contact at the refined location 164 with the first responder 140. As such, the tracker 172 may be configured to determine the refined location 164 of the incident scene 136 based on the first responder 140 traveling from the initial location 158 and establishing patient contact at the refined location 164. In some embodiments, the tracker 172 includes at least one of a GPS tracker, a cellular tracker, and a WiFi tracker. In such embodiments, the step 110 of determining the refined location 164 includes a step 174 in which the tracker 172 determines its location based on at least one of a GPS signal, a cellular signal, and a WiFi signal. As such, to determine the refined location 164 during step 110, the first responder 140 may establish patient contact at the refined location 164 with the tracker 172 during step 162, and the tracker 172 may determine its location using a GPS signal, a cellular signal, and/or a WiFi signal during step 174.

In some embodiments, the first communication system 120 includes a mobile computing device such as the mobile phone 120M, a laptop computer, a tablet, or any other computing system suitable for communicating the refined location 164. In such embodiments, the tracker 172 may be coupled to the mobile computing device and the step 112 of communicating the refined location 164 of the incident scene 136 includes a step 176 of transmitting data D1 (shown in FIG. 3) associated with a location of the tracker 172 to the navigation system 86 of the autonomous patient support apparatus 20. In embodiments where the tracker 172 is coupled to the mobile computing device, the mobile computing device may execute the step 176. Furthermore, in such embodiments, the mobile computing device may transmit the data D1 associated with the location of the tracker 172 to the navigation system 86 via the remote dispatch center 126. As such, the remote dispatch center 126 may process the data D1 associated with the location of the tracker 172 prior to transmitting the data to the navigation system 86.

In other embodiments, the first communication system 120 may include the tracker 172 and the tracker 172 may include a tracker user interface, such as a touchscreen, a button, a switch, or any other user interface suitable for receiving an input from a user of the tracker 172. For example, the tracker user interface may be a handheld device comprising a button, such as the tracker user interface 120T shown in FIG. 4B. In such embodiments, the step 112 of communicating the refined location 164 of the incident scene 136 includes the step 176 of transmitting data D1 associated with the location of the tracker 172 to the navigation system 86 of the autonomous patient support apparatus 20. In embodiments where the tracker 172 includes the tracker user interface 120T, the tracker 172 may execute the step 176 after the tracker user interface 120T is actuated. For example, in an instance where the tracker user interface 120T is realized as a touchscreen, the tracker 172 may transmit data D1 associated with the location of the tracker 172 after a "TRANSMIT" button is actuated on the touchscreen. Additionally, the tracker 172 may transmit the data D1 associated with the location of the tracker 172 to the navigation system 86 via the remote dispatch center 126.

As shown in FIG. 6D, the method 100 includes the step 116 of generating the drive path 186 with the navigation system 86. In an embodiment including the step 166 of equipping the first responder 140 with at least one of a radio communication device 120R and a mobile phone 120M, the navigation system 86 may determine the drive path 186 during step 116 based on a voice command VC received from the first responder 140 via the radio communication device 120R and/or the mobile phone 120M. The controller 93 may then control the drive system 84 based on the drive path 186 such that the autonomous patient support apparatus 20 travels from the initial location 158 to the refined location 164.

In embodiments including the tracker 172, the step 116 of generating the drive path 186 may include a step 180 of generating a tracker path 184 based on movement of the first responder 140 away from the initial location 158. In such embodiments, step 180 may be executed by the tracker 172 and the tracker path 184 includes a plurality of locations associated with the tracker 172. Additionally, in embodiments including step 180, the step 116 of generating the drive path 186 may also include a step 182 of generating the drive path 186 with the navigation system 86 based on the tracker path 184. The controller 93 may then control the drive system 84 based on the drive path 186.

FIG. 6E illustrates one embodiment of steps 180 and 182. As shown, the first responder 140 is equipped with the tracker 172 and is moving towards the refined location 164 of the incident scene 136. Accordingly, during step 180, the tracker 172 generates the tracker path 184 based on the movement of the first responder 140 and during step 182, the navigation system 86 generates the drive path 186. In FIG. 6E, the drive path 186 is generated in accordance with a "follow me" mode as disclosed in U.S. Patent Application Publication No. 2014/0076644A1, which claims priority to U.S. Provisional Patent App. No. 61/702,316, filed on Sep. 18, 2012, entitled "Powered Patient Support Apparatus," the disclosures of which are hereby incorporated by reference in their entirety. As shown, the controller 93 controls the drive system 84 based on the drive path 186 such that the autonomous patient support apparatus 20 follows the first responder 140.

FIG. 6F illustrates another embodiment of steps 180 and 182. As shown, the first responder 140 is equipped with the tracker 172 and has established patient contact at the incident scene 136. Accordingly, during step 180, the tracker 172 generates the tracker path 184 based on the movement of the first responder 140 and during step 182, the navigation system 86 generates the drive path 186. However, in the embodiment of FIG. 6F, the drive path 186 is generated such that a distance between the initial location 158 and the refined location 164 is minimized.

Referring to FIG. 6A, steps 166 and 168 are illustrated using dotted lines ("---"). Embodiments of any method herein including a step that is illustrated using the dotted lines also include step 166. For example, embodiments of the method 100 that include the step 168 of transmitting the voice command VC with the radio communication device 120R and/or the mobile phone 120M also include the step 166 of equipping the first responder 140 with the radio communication device 120R and/or the mobile phone 120M.

Referring to FIGS. 6A and 6D, steps 173, 174, 176, 180, and 182 are illustrated using dot-dash lines ("-•-"). Embodiments of any method herein including a step that is illustrated using the dot-dash lines also include step 173. For example, embodiments of the method 100 that include the step 176 of transmitting data D1 associated with the location of the tracker 172 to the navigation system 86 also include the step 173 of equipping the first responder 140 with the tracker 172. As another example, embodiments of the method 100 that include the step 180 of generating the tracker path 184 also include the step 173 of equipping the first responder 140 with the tracker 172.

Figure 6G:
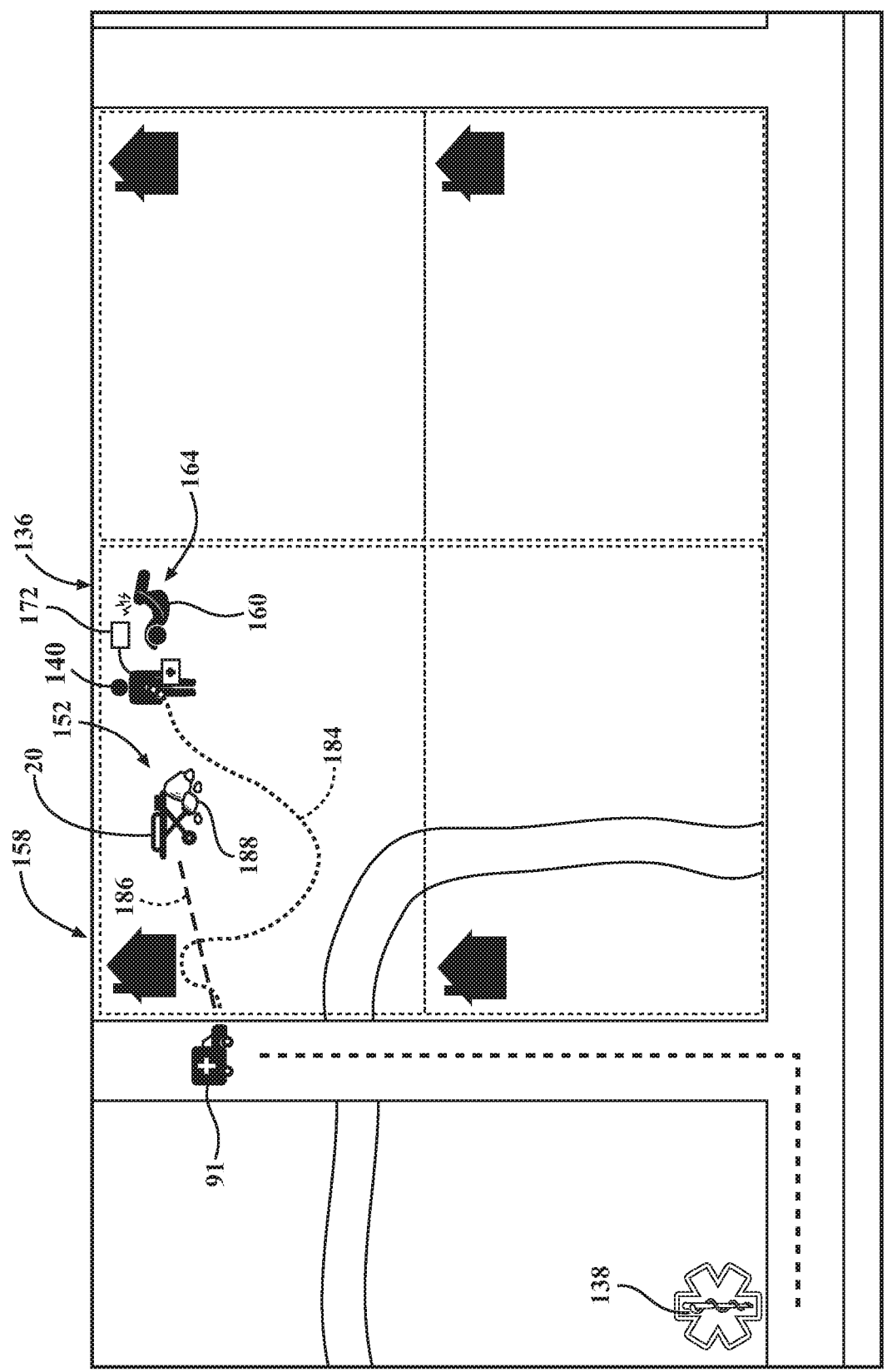

In FIG. 6G, an instance where the autonomous patient support apparatus 20 has encountered an obstruction 188 is shown. As shown in FIG. 6G, the obstruction 188 prevents the drive system 84 from driving the autonomous patient support apparatus 20 to the refined location 20. In such instances, the autonomous patient support apparatus 20 may include the above-described obstruction detection system 88. Referring back to FIG. 6A, the method 100 may further include a step 190 of detecting a presence of the obstruction 188 at an obstruction location 192 and a step 194 of interrupting operation of the drive system 84 in response to detecting the obstruction 188 at the obstruction location 192. The obstruction detection system 88 may be configured to detect the presence of the obstruction 188 during step 190 and may be configured to communicate with the controller 93 to interrupt operation of the drive system 84 during step 194.

Figure 6H:
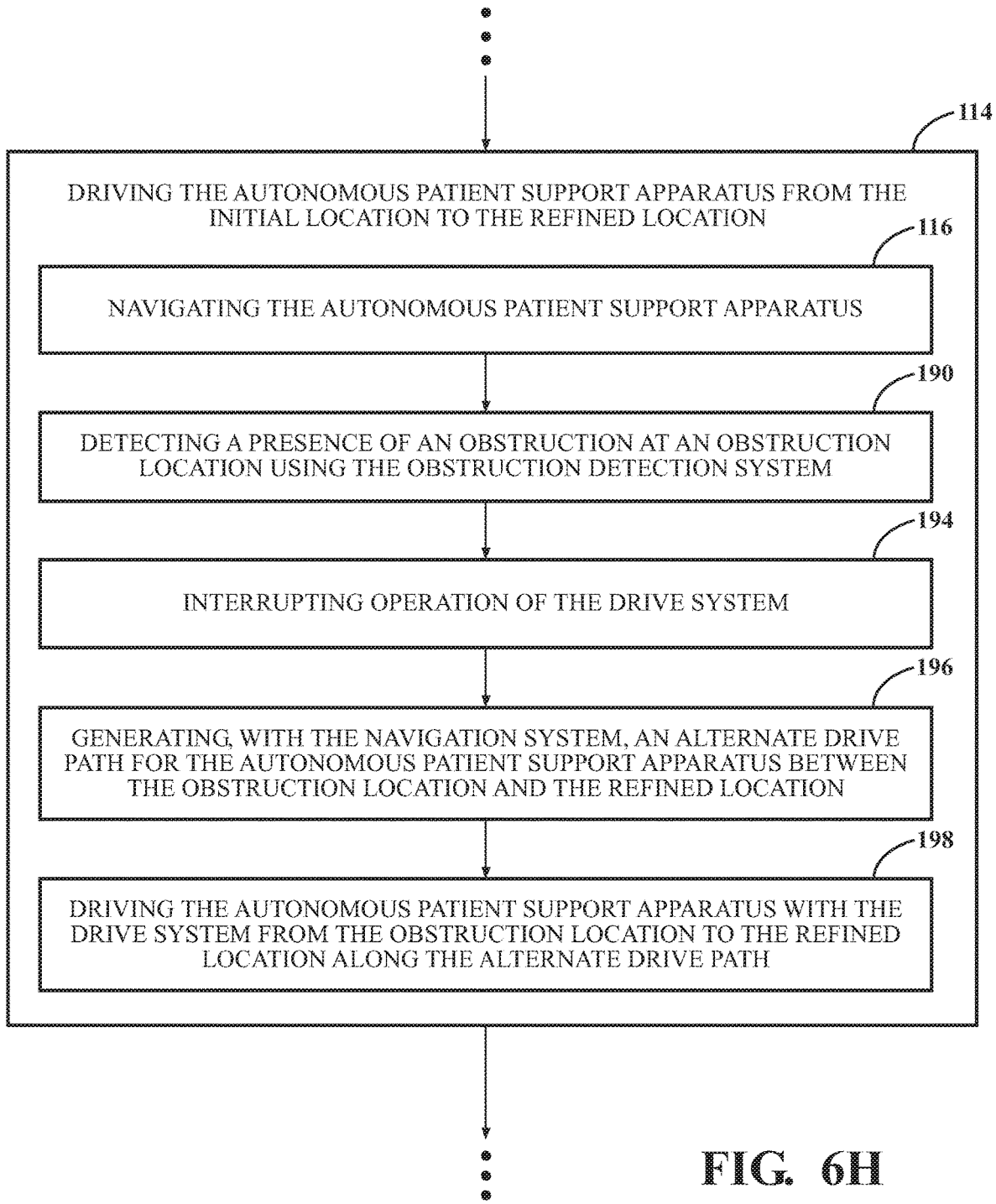

After detecting the presence of the obstruction 188, the method 100 may proceed in a variety of ways. For example, as shown in FIG. 6H, the method may proceed to a step 196 of generating, with the navigation system 86, an alternate drive path for the autonomous patient support apparatus 20 between a location of the obstruction location 192 and the refined location 164. In such an embodiment, the obstruction detection system 88 may communicate with the navigation system 86 via the controller 93. The method may then proceed to a step 198 of driving the autonomous patient support apparatus 20 with the drive system 84 from the obstruction location 192 along the alternate drive path. For example, in FIG. 6G, the obstruction 188 is illustrated as a pile of rocks, which are preventing the drive system 84 from driving the patient support apparatus 20 along the drive path 186. During step 196, the navigation system 86 may generate an alternate drive path, which bypasses the obstruction 188. Accordingly, the autonomous patient support apparatus 20 may bypass the obstruction 188 by driving from the obstruction location 192 along the alternate drive path.

In another example, shown in FIG. 6I, the method 100 may proceed to a step 200 of determining that the autonomous patient support apparatus 20 cannot reach the refined location 164 with the drive system 84. The method 100 may then proceed to a step 202 of generating an alarm A (shown in FIG. 3) with the patient support apparatus 20 to indicate that the obstruction 188 cannot be traversed without intervention. As shown in FIG. 3, the alarm A may include an alarm A transmitted to the remote dispatch center 126 and/or to the first responder 140 via the first communication system 120. The alarm A may also include an audible alarm, a visual alarm, a tactile alarm, or any other alarm suitable for indicating that the obstruction 188 cannot be traversed without intervention. Steps 200 and 202 may be executed by the obstruction detection system 88.

Figure 6J:
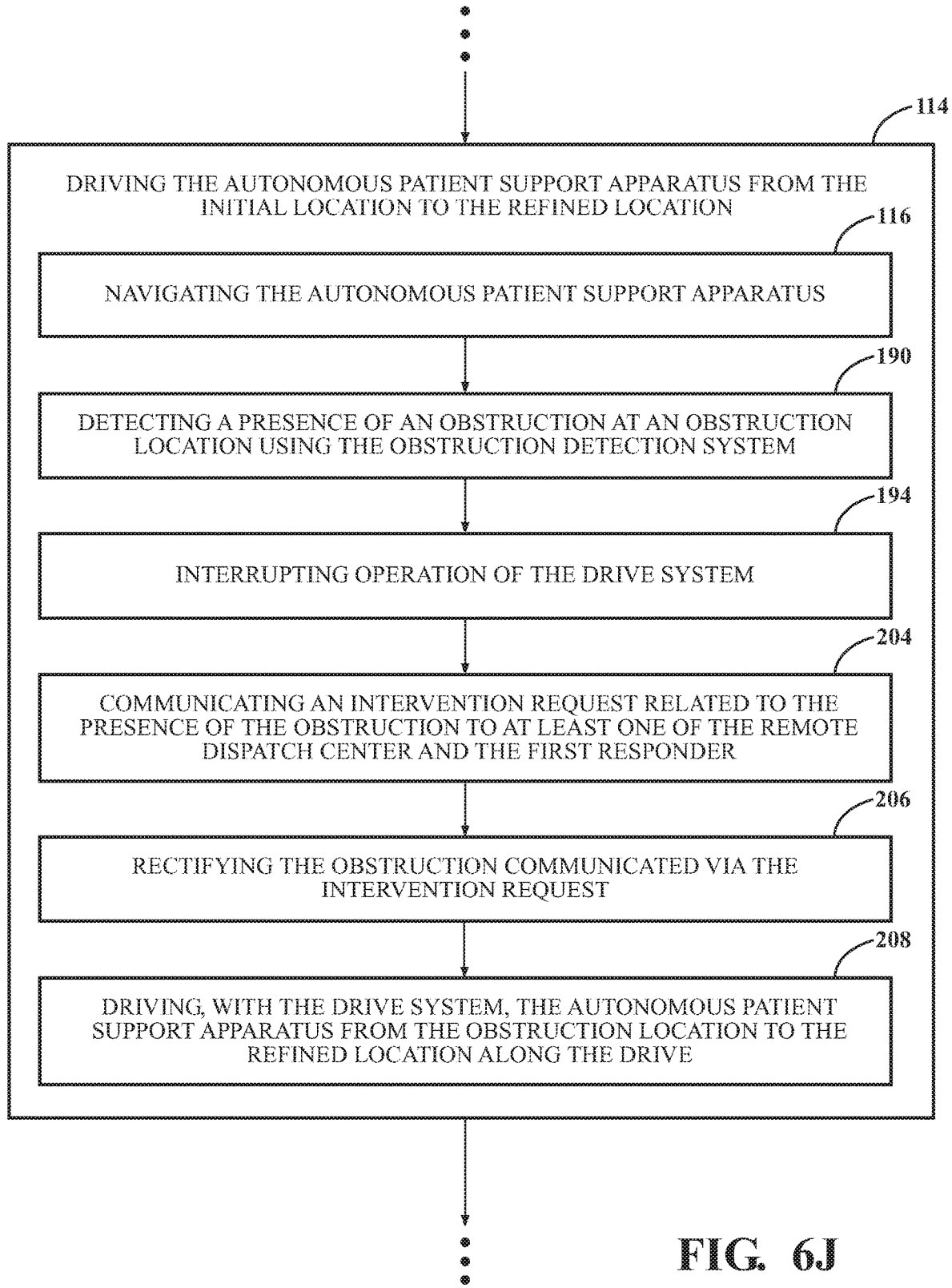

In yet another example, shown in FIG. 6J, the method 100 may proceed to a step 204 of communicating, with the obstruction detection system 88, an intervention request IR (shown in FIG. 3) related to the presence of the obstruction 188 to the remote dispatch center 126 and/or to the first responder 140 via the first communication system 120. Accordingly, the method 100 may then proceed to a step 206 of rectifying the obstruction 188 communicated via the intervention request IR and a step 208 of driving, with the drive system 84, the autonomous patient support apparatus 20 from the obstruction location 192 to the refined location 164 along the drive path 186. For example, referring to FIG. 6G, the obstruction 188 is illustrated as a pile of rocks, which are preventing the drive system 84 from driving the patient support apparatus 20 along the drive path 186. During step 206, the first responder 140 may move the pile of rocks to rectify the obstruction 188. Accordingly, the drive system 84 may then continue driving the autonomous patient support apparatus 20 along the drive path 186.

Figure 7A:
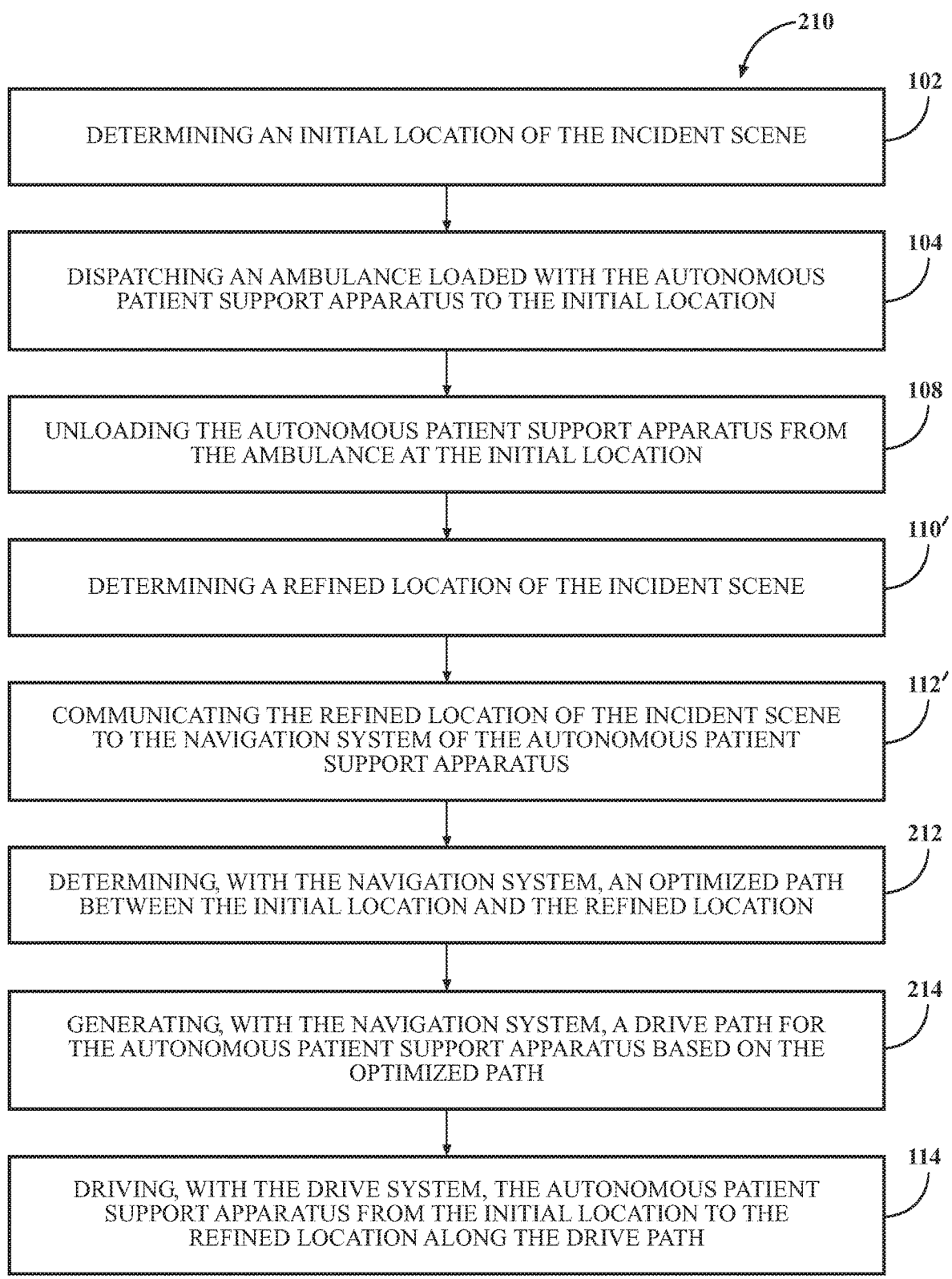
FIG. 7A is a diagrammatic view of a method of transporting the autonomous patient support apparatus to the incident scene via an optimized path.

FIG. 7A illustrates a method 210 of transporting an autonomous patient support apparatus, such as the above-described autonomous patient support apparatus 20, to an incident scene 136 via an optimized drive path. As shown, the method 210 includes the above-described step 102 of determining the initial location 158 of the incident scene 136; the above-described step 104 of dispatching the ambulance 91 loaded with the autonomous patient support apparatus 20 to the initial location 158; the above-described step 108 of unloading the autonomous patient support apparatus 20 from the ambulance 91 at the initial location 158; and the above-described step 114 of driving, with the drive system 84, the autonomous patient support apparatus 20 from the initial location 158 to the refined location 164.

The method 210 also includes a second embodiment 110' of the step 110 of determining the refined location 164 of the incident scene 136 and a second embodiment 112' of the step 112 of communicating the refined location 164 of the incident scene 136 to the navigation system 86 of the autonomous patient support apparatus 20. Additionally, the method 210 includes a step 212 of determining, with the navigation system 86, an optimized path between the initial location 158 and the refined location 164; and a step 214 of generating, with the navigation system 86, the drive path (also shown as "DP (186)" in FIG. 7B) for the autonomous patient support apparatus 20 based on the optimized path.

Figure 7B:
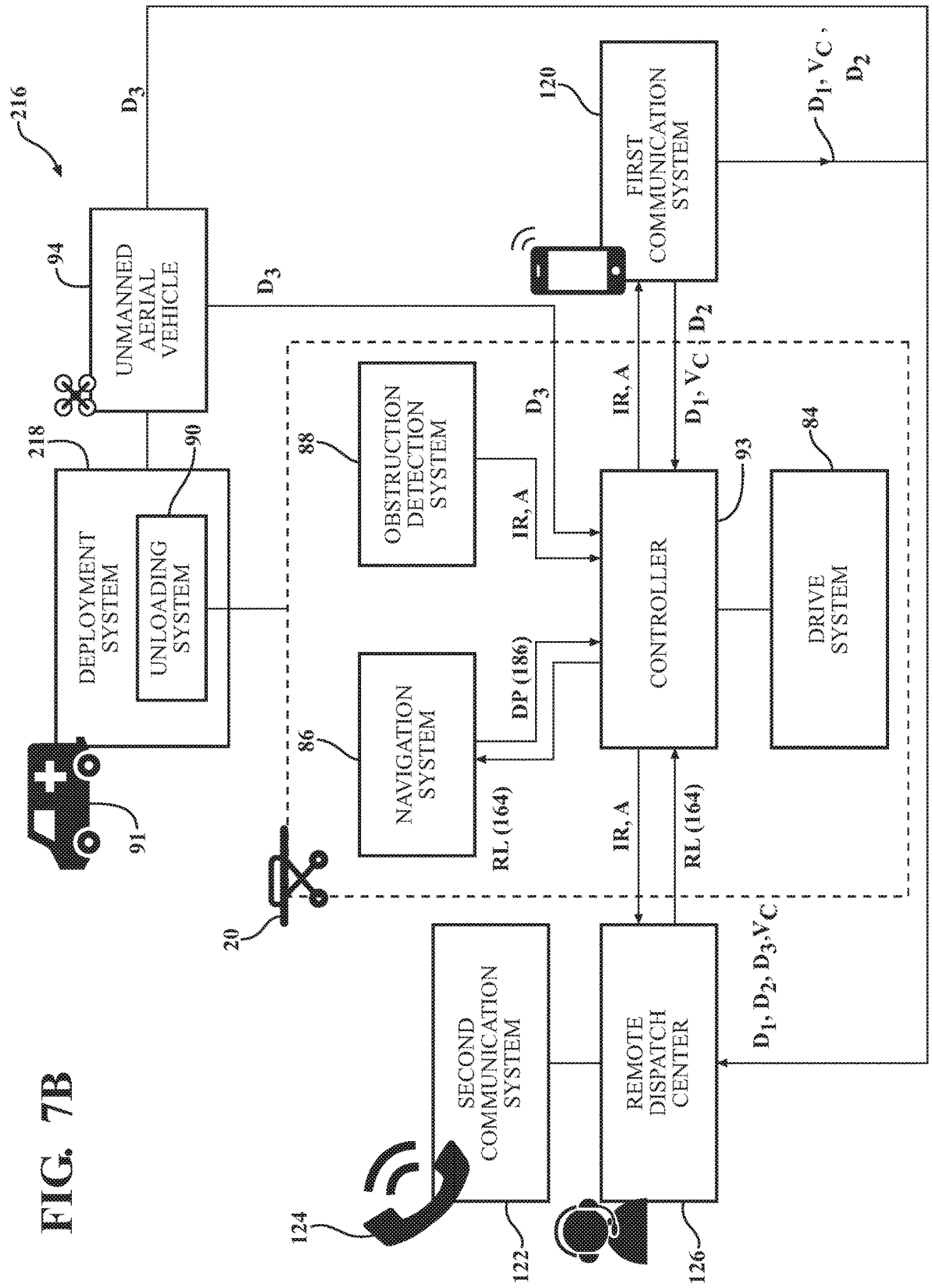
FIG. 7B is a schematic view of a system for transporting the autonomous patient support apparatus to the incident scene via the optimized path.
Figure 7C:
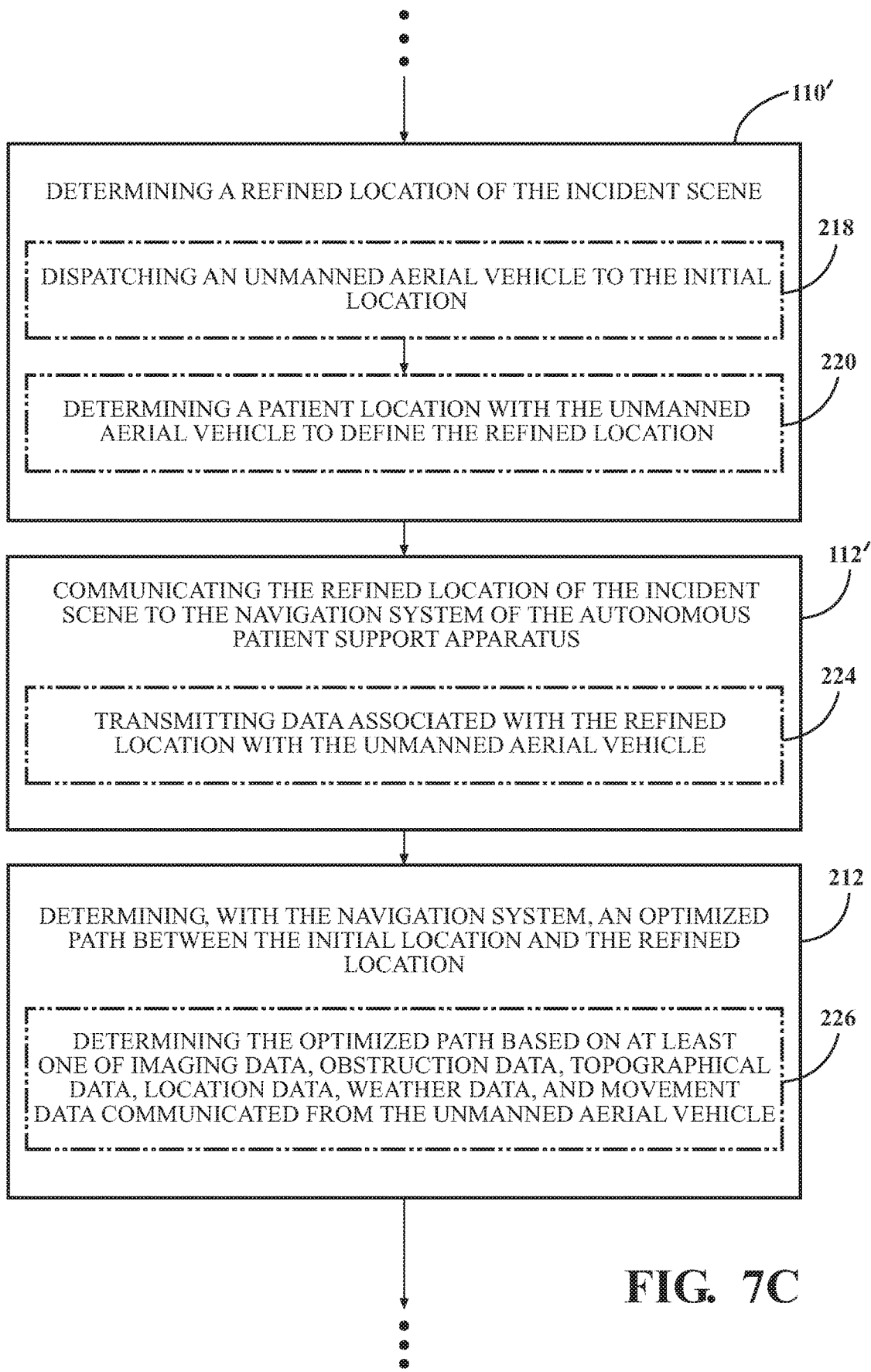
FIGS. 7C-7S are diagrammatic views of embodiments of the method of transporting the autonomous patient support apparatus to the incident scene via the optimized path.
Figure 7D:
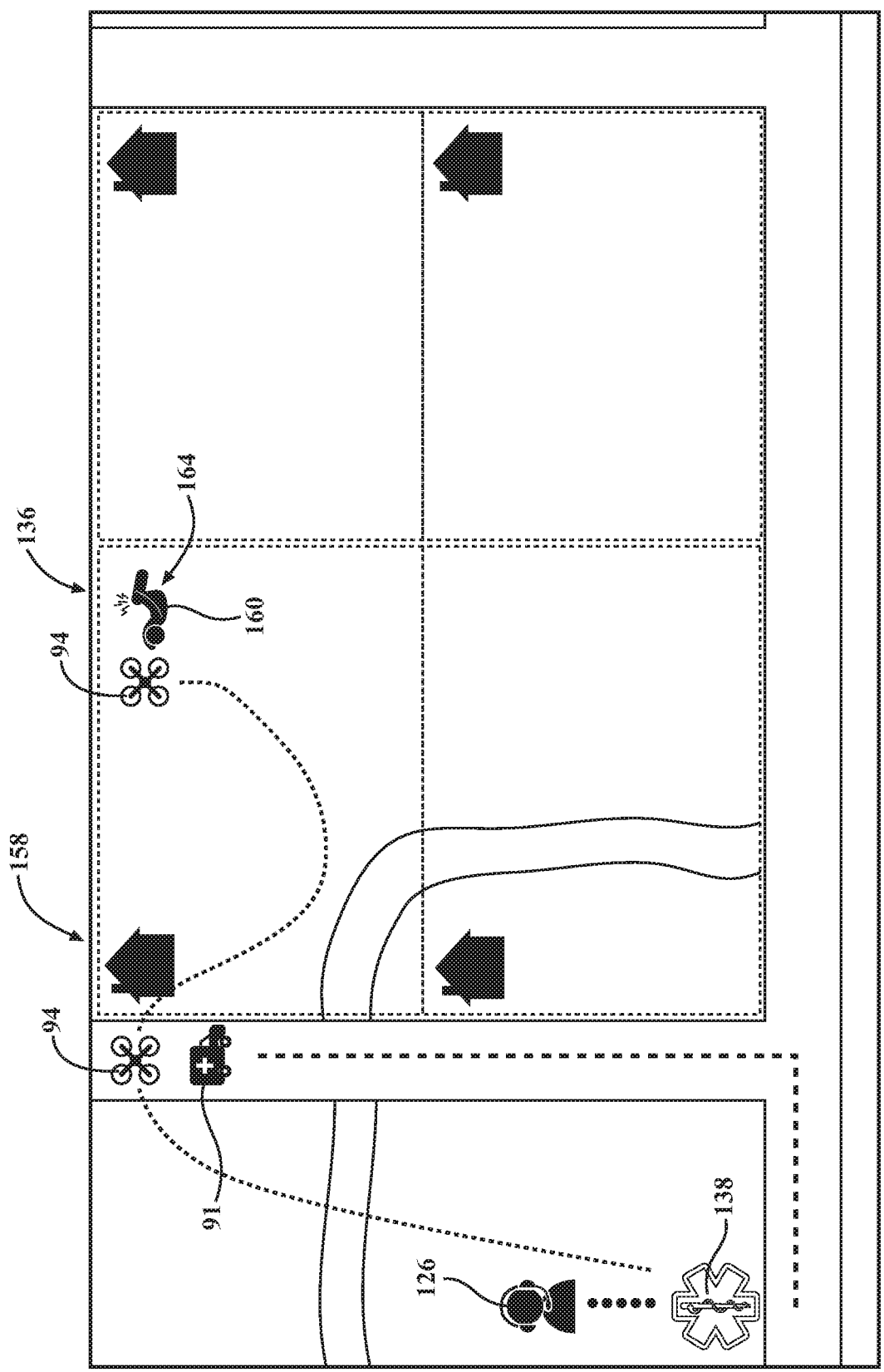
Figure 7F:
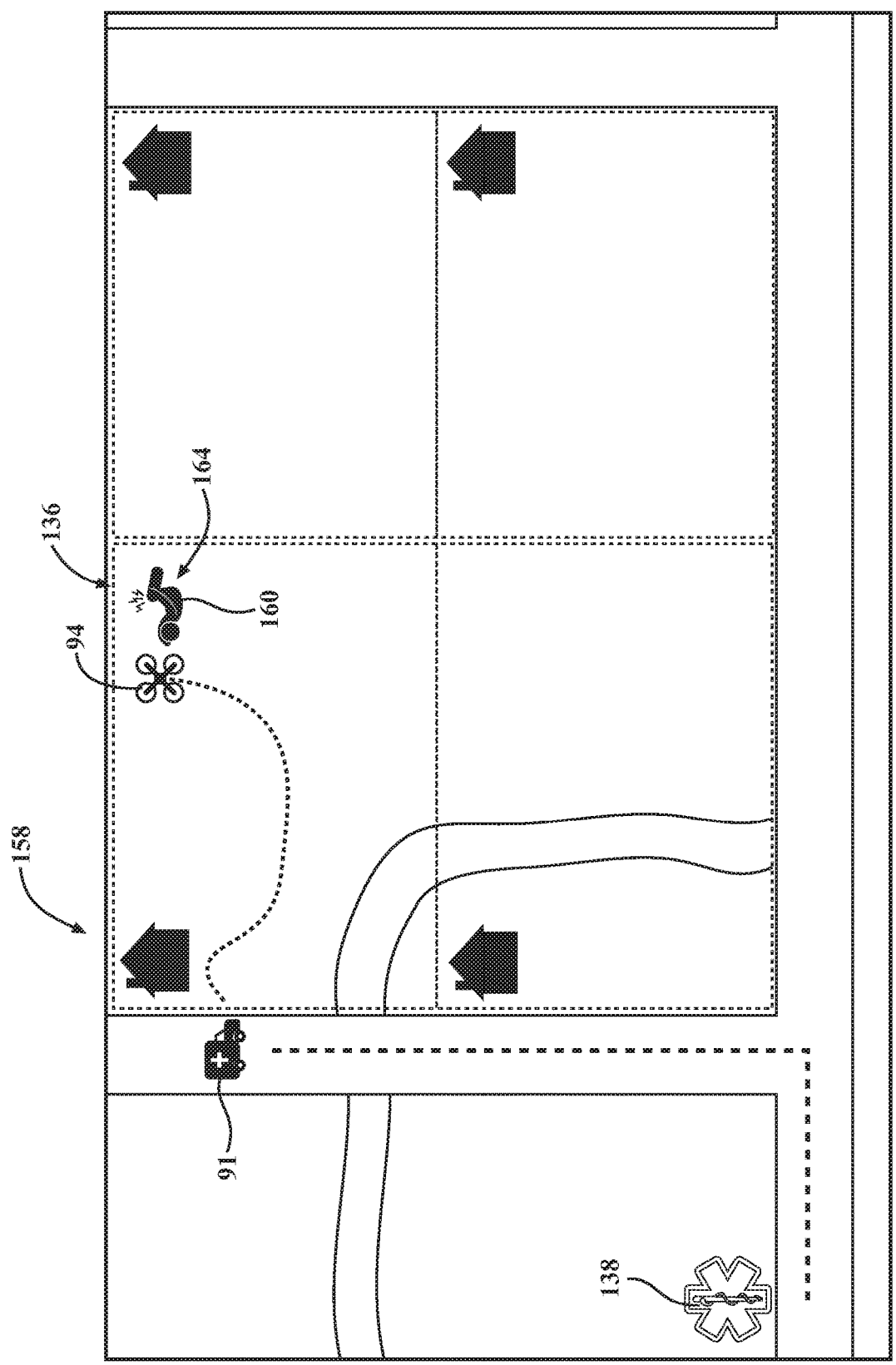
Figure 7G:
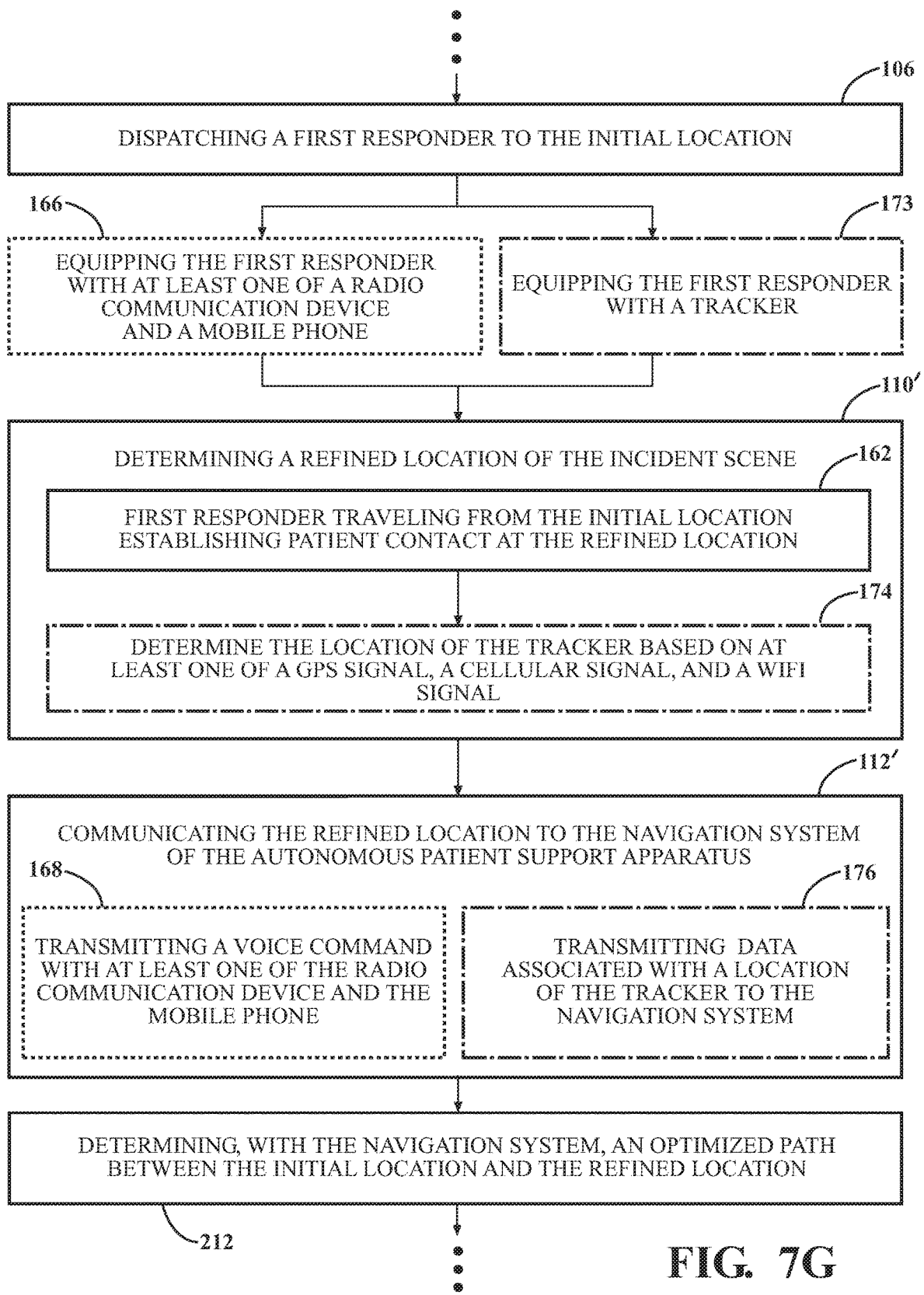
Figure 7H:
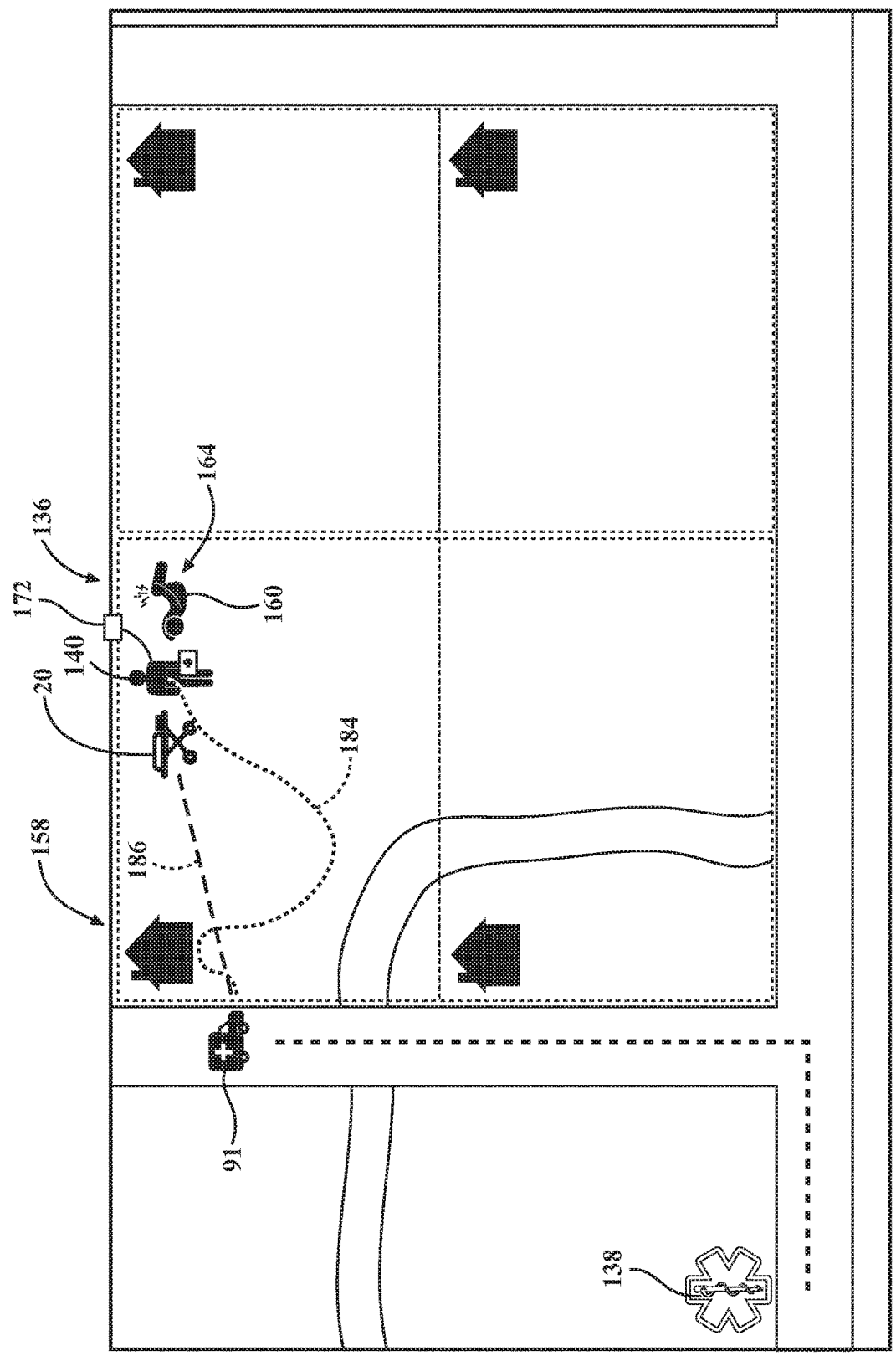

Referring to FIG. 7H, one instance of the method 210 is shown. As shown, the first responder 140 establishes patient contact to determine the refined location 164 of the incident scene 136. The navigation system 86 then determines an optimized path (not shown in FIG. 7H) between the initial location 158 and the refined location 164 during step 212. In some embodiments, the optimized path may be based on at least one of topographical data, street mapping data, traffic data, and building infrastructure data. In such embodiments, the navigation system 86 may receive this information from the first responder 140 in the form of data D2 (shown in FIG. 7B) associated with the first responder 140 traveling from the initial location 158 to the refined location 164. The navigation system 86 may also receive this information from an internet connection. Accordingly, the navigation system 86 generates the drive path 186 for the autonomous patient support apparatus 20 based on the optimized path during step 214. The controller 93 then controls the drive system 84 to drive the autonomous patient support apparatus 20 from the initial location 158 to the refined location 164 along the drive path 186.

As shown in FIG. 7B, the steps 102, 104, 108, 110', 112', 212, and 214 may be executed by components of a system 216 for transporting the autonomous patient support apparatus 20 to the incident scene 136 via the optimized path. As shown, the system 216 includes the components of system 118 and a deployment system 218 of the ambulance 91. In one instance, the deployment system 218 may deploy an unmanned aerial vehicle, such as the above-described unmanned aerial vehicle 94 from the ambulance 91. In another instance, the deployment system 218 may include the unloading system 90 and may unload the autonomous patient support apparatus 20 from the ambulance 91. In some embodiments, some of the components of system 216 may be omitted.

In some embodiments, the ambulance 91 may be loaded with an unmanned aerial vehicle, such as the above-described unmanned aerial vehicle 94. In such embodiments, the step 110' may include a step 218 of dispatching the unmanned aerial vehicle 94 from the ambulance 91 to the initial location 158 as shown in FIG. 7C. The step 110' also includes a step 220 of determining a location of the patient 160 with the unmanned aerial vehicle 94 to define the refined location 164 of the incident scene. The steps 218 and 220 are further illustrated in FIG. 7D. As shown, the unmanned aerial vehicle 94 is dispatched to the initial location 158 and then determines the location of the patient 160 by travelling toward the incident scene 136 in order to define the refined location 164. For example, as previously stated, the unmanned aerial vehicle 94 may include a variety of sensors, such as an imaging sensor realized as the camera 95 (shown in FIG. 5) and a location sensor. As such, the camera 95 may capture imaging data while the unmanned aerial vehicle 94 travels towards the incident scene 136. The imaging data may then be analyzed to determine the refined location 164 relative to the location of the unmanned aerial vehicle 94.

In another embodiment where the ambulance 91 is loaded with the unmanned aerial vehicle 94, the step 110' includes a step 222 of deploying the unmanned aerial vehicle 94 from the ambulance 91 at the initial location 158, as shown in FIG. 7E. The step 110' also includes the above-described step 220. The steps 222 and 220 are further illustrated in FIG. 7F. As shown, the unmanned aerial vehicle 94 is deployed from the ambulance 91 at the initial location 158 and then determines the location of the patient 160 by travelling toward the incident scene 136 in order to define the refined location 164. The unmanned aerial vehicle 94 may be deployed from the ambulance 91 by the deployment system 218.

In embodiments where the ambulance 91 is loaded with the unmanned aerial vehicle 94, the step 112', as shown in FIGS. 7C and 7E, may include a step 224 of transmitting data D3 (shown in FIG. 7B) associated with the refined location 164 with the unmanned aerial vehicle 94. As shown in FIG. 7B, the data D3 associated with the refined location 164 may be transmitted from the unmanned aerial vehicle 94 to the navigation system 86 via the controller 93 and via the remote dispatch center 126. The data D3 associated with the refined location 164 may include imaging data, obstruction data, topographical data, location data, weather data, and movement data. As such, the step 212 of determining, with the navigation system 86, an optimized path between the initial location 158 and the refined location 164 may include a step 226 of determining the optimized path based on at least one of imaging data, obstruction data, topographical data, location data, weather data, and movement data communicated from the unmanned aerial vehicle 94. For example, during step 226, the navigation system 86 may determine the optimized path based on imaging data of topographical features communicated from the unmanned aerial vehicle 94.

Referring to FIGS. 7C and 7E, steps 218, 220, 222, 224, and 226 are illustrated using dot-dot-dash lines ("••-"). Embodiments of any method herein including a step that is illustrated using the dot-dot-dash lines also include either step 218 or 222. For example, embodiments of the method 210 that include the step 226 of determining the optimized path based on imaging data, obstruction data, topographical data, location data, weather data, and/or movement data communicated from the unmanned aerial vehicle 94 include either the step 218 of dispatching the unmanned aerial vehicle 94 to the initial location 158 or the step 222 of deploying the unmanned aerial vehicle 94 from the ambulance 91 at the initial location 158.

FIG. 7G illustrates an embodiment where the method 210 includes the step 112' of communicating the refined location 164 to the navigation system 86. In embodiments where the first responder 140 is equipped with the radio communication device 120R and/or the mobile phone 120M, the step 112' may include the above-described step 168 of transmitting the voice command VC (also shown in FIG. 7B) with the radio communication device 120R and/or the mobile phone 120M. In such an embodiment, the voice command VC may include a description of the refined location 164 from the first responder 140. During step 212, the navigation system 86 may then determine the optimized path between the initial location 158 and the refined location 164 based on the voice command VC. In embodiments where the tracker 172 is coupled to the above-described mobile computing device or where the tracker 172 includes the above-described tracker user interface 120T, the step 112' may also include the above-described step 176 of transmitting data D1 (also shown in FIG. 7B) associated with the location of the tracker 172 to the navigation system 86. During step 212, the navigation system 86 may then determine the optimized path between the initial location 158 and the refined location 164 based on the data D1 associated with the location of the tracker 172.

FIG. 7H illustrates the embodiment where the method includes the step 112' and where the tracker is coupled to the mobile computing device. In such an embodiment, the method 210 includes the steps 106, 173, 110', 162, 174, 112', 176, and 212. As shown, the first responder 140 is equipped with the tracker 172, the first responder 140 establishes patient contact at the refined location 164, the tracker 172 determines its location at the refined location 164 during step 174, and the mobile computing device transmits data D1 associated with the location of the tracker 172 to the navigation system 86. The navigation system 86 then determines the optimized path based on the data D1 associated with the location of the tracker 172 and generates the drive path 186 accordingly. The controller 93 then controls the drive system 84 to drive the autonomous patient support apparatus 20 from the initial location 158 to the refined location 164 along the drive path 186.

Figure 7I:
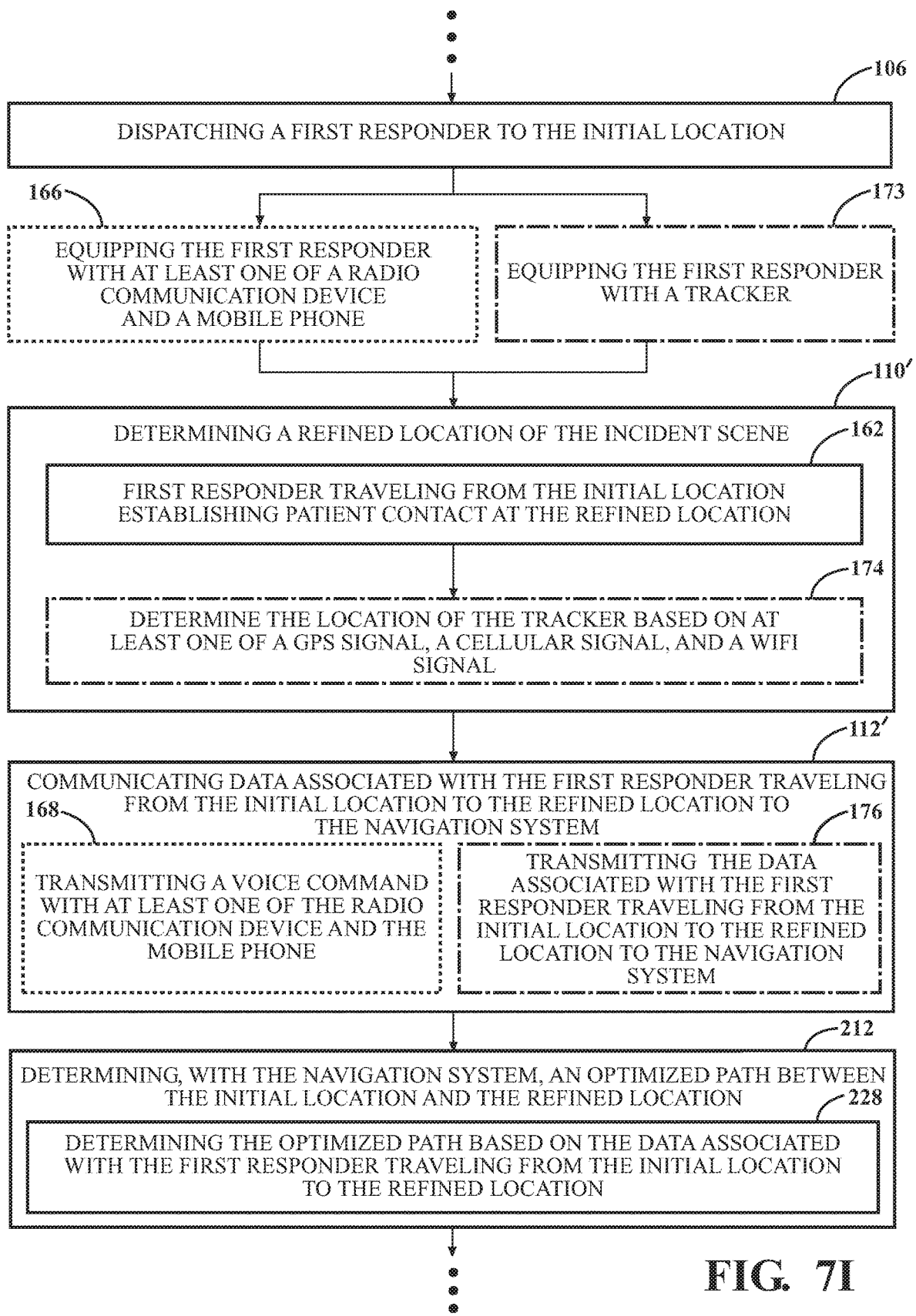

FIG. 7I illustrates an embodiment where the method 210 includes a step 112' of communicating data D2 (shown in FIG. 7B) associated with the first responder 140 traveling from the initial location 158 to the refined location 164 to the navigation system 86 of the autonomous patient support apparatus 20. As shown, the data D2 associated with the first responder 140 traveling from the initial location 158 to the refined location 164 may be transmitted to the navigation system 86 via the controller 93 and via the remote dispatch center 126. Additionally, the step 212 of determining the optimized path with the navigation system 86 may include a step 228 of determining the optimized path based on the data D2 associated with the first responder 140 traveling from the initial location 158 to the refined location 164.

In embodiments where the first responder 140 is equipped with at least one of the radio communication device 120R and the mobile phone 120M, the step 112' may include the step 168 of transmitting the voice command VC with the radio communication device 120R and/or the mobile phone 120M. In such an embodiment, the voice command VC may include a description of any suitable information associated with the first responder 140 traveling from the initial location 158 to the refined location 164. For example, the voice command VC may include a description of topographical features, a warning of a potential obstruction, and/or a suggested optimized path.

Similarly, in embodiments where the first responder 140 is equipped with the tracker 172, the step 112' includes the step 176 of transmitting the data D2 associated with the first responder 140 traveling from the initial location 158 to the refined location 164 to the navigation system 86. For example, the data D2 may include a notification of topographical features, a warning of a potential obstruction, and/or a suggested optimized path. In an embodiment where the tracker 172 is coupled to the mobile computing device, the mobile computing device may transmit the data D2 associated with the first responder 140 traveling from the initial location 158 to the refined location 164 to the navigation system 86. For example, the mobile computing device may transmit data D2 indicating a location and an approximate size of a pond that the first responder 140 encountered. In an embodiment where the tracker 172 includes the tracker user interface 120T, the tracker 172 may transmit the data D2 associated with the first responder 140 after the first responder 140 actuates the tracker user interface 120T. For example, the tracker 172 may transmit data D2 indicating a location of a steep cliff after the first responder 140 depresses a button on the tracker user interface 120T.

Figure 7J:
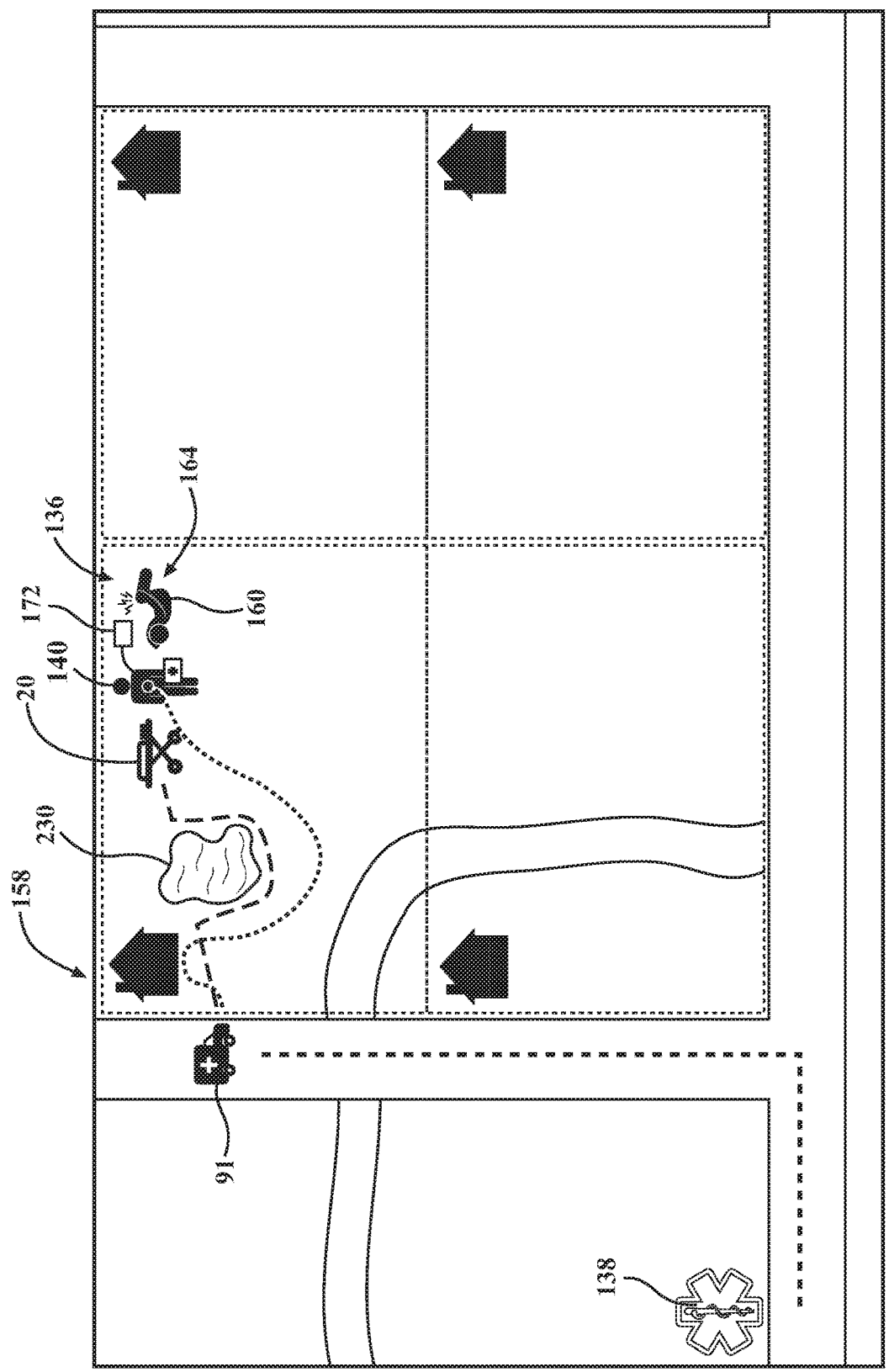

FIG. 7J illustrates an embodiment where the first responder 140 is equipped with the tracker 172, and the method 210 includes the step 112' of transmitting the data D2 associated with the first responder 140 traveling from the initial location 158. In such an embodiment, the method 210 includes the steps 106, 173, 162, 176, 174, 112', 176, 212, and 228. As shown, the tracker 172 is carried by the first responder 140 and the first responder 140 observes a pond 230 while traveling from the initial location 158 to the refined location 164. In FIG. 7J, the tracker 172 may be coupled to the mobile computing device. Accordingly, the mobile computing device transmits data D2 indicating a location of the pond 230 to the navigation system 86 in the form of data D2 associated with the first responder 140 traveling from the initial location 158 to the refined location 164. For example, the first responder 140 may transmit the location of the pond 230 to the navigation system 86 by pressing an "OBSTRUCTION DETECTED" button on a touchscreen of the mobile computing device. The navigation system 86 then determines the optimized path such that the autonomous patient support apparatus 20 avoids the pond 230 when traveling to the refined location 164 and generates the drive path 186 around the pond 230. The controller 93 then controls the drive system 84 to drive the autonomous patient support apparatus 20 from the initial location 158 to the refined location 164 along the drive path 186.

Figure 7K:
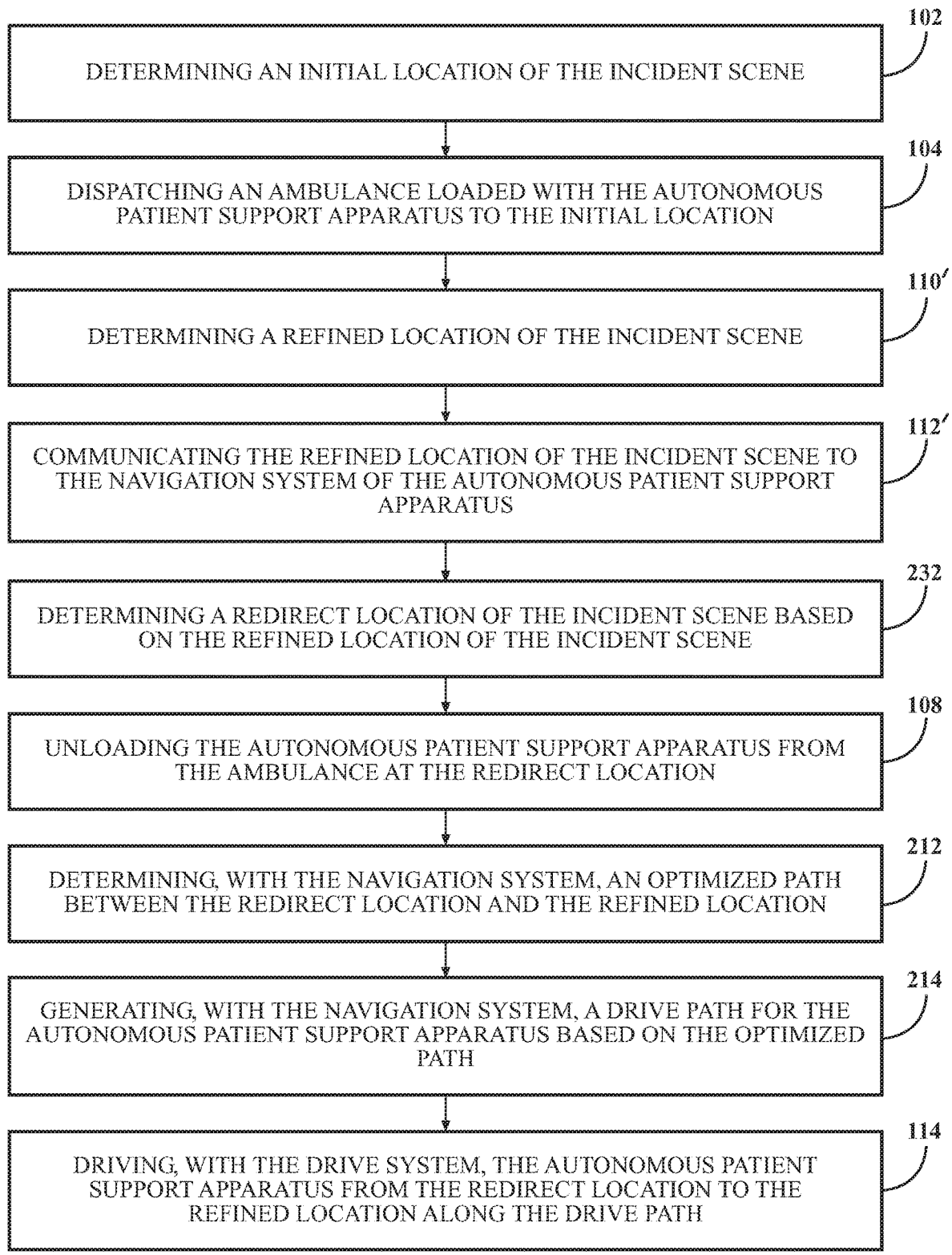

FIG. 7K illustrates an embodiment where the method 210 includes a step 232 of determining a redirect location of the incident scene 136 based on the refined location 164 of the incident scene 136. For example, the first responder 140 may determine that the autonomous patient support apparatus 20 may not reach or will encounter great difficulty when attempting to reach the refined location 164. In such embodiments, the navigation system 86 determines the redirect location of the incident scene 136 after the refined location 164 is determined and communicated to the navigation system 86 during steps 110' and 112', respectively. For instance, during step 112', data D1 associated with the location of the tracker 172 and/or data D2 associated with the first responder 140 traveling from the initial location 158 to the refined location 164 may be transmitted to the navigation system 86. For example, the first responder 140 may encounter a river or hazardous terrain, and may notify the navigation system 86 via data D2 associated with the first responder 140 traveling from the initial location 158 to the refined location 164. The navigation system 86 may then determine a redirect location.

During step 232, the navigation system 86 may determine the redirect location of the incident scene based on the refined location 164. As shown in FIG. 7M, step 232 may include the step 234 of evaluating each of the initial location 158 and the redirect location relative to the refined location 164 based on one or more of an obstacle presence, topographical data, street mapping data, street traffic data, and building infrastructure data. The navigation system 86 may also evaluate a distance between the initial location 158 and the refined location compared to a distance between the redirect location and the refined location 164.

After the navigation system 86 determines the redirect location, the unloading system 90 unloads the autonomous patient support apparatus 20 during step 108 at the redirect location. The method 210 then proceeds to the above-described step 212 of determining, with the navigation system 86, the optimized path. However, in this instance of step 212, the navigation system 86 determines the optimized path between the redirect location and the refined location 164. The method 210 then proceeds to generate the drive path 186 during step 214 and drives the autonomous patient support apparatus 20 along the drive path 186 during step 114.

Figure 7L:
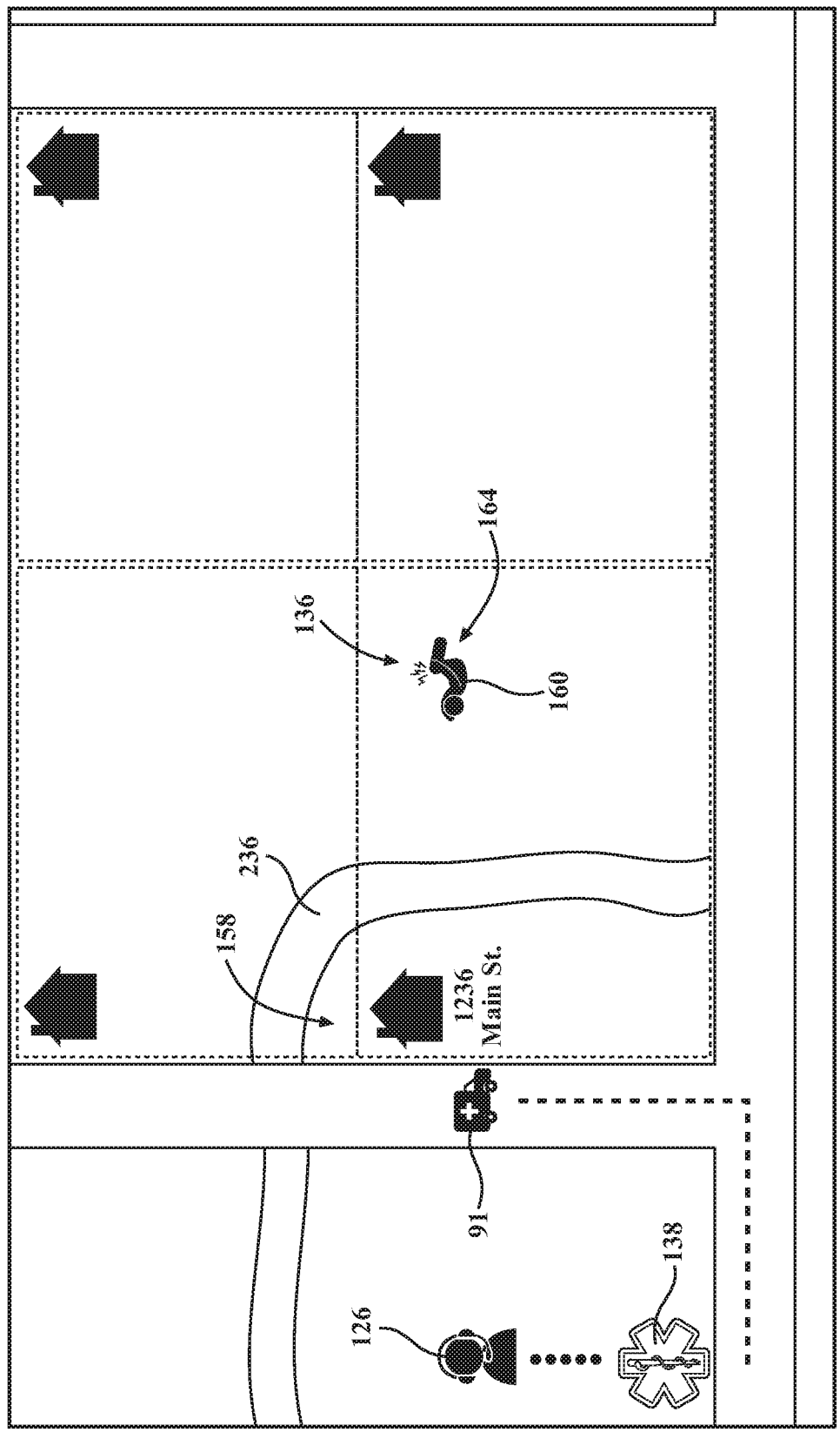
Figure 7M:
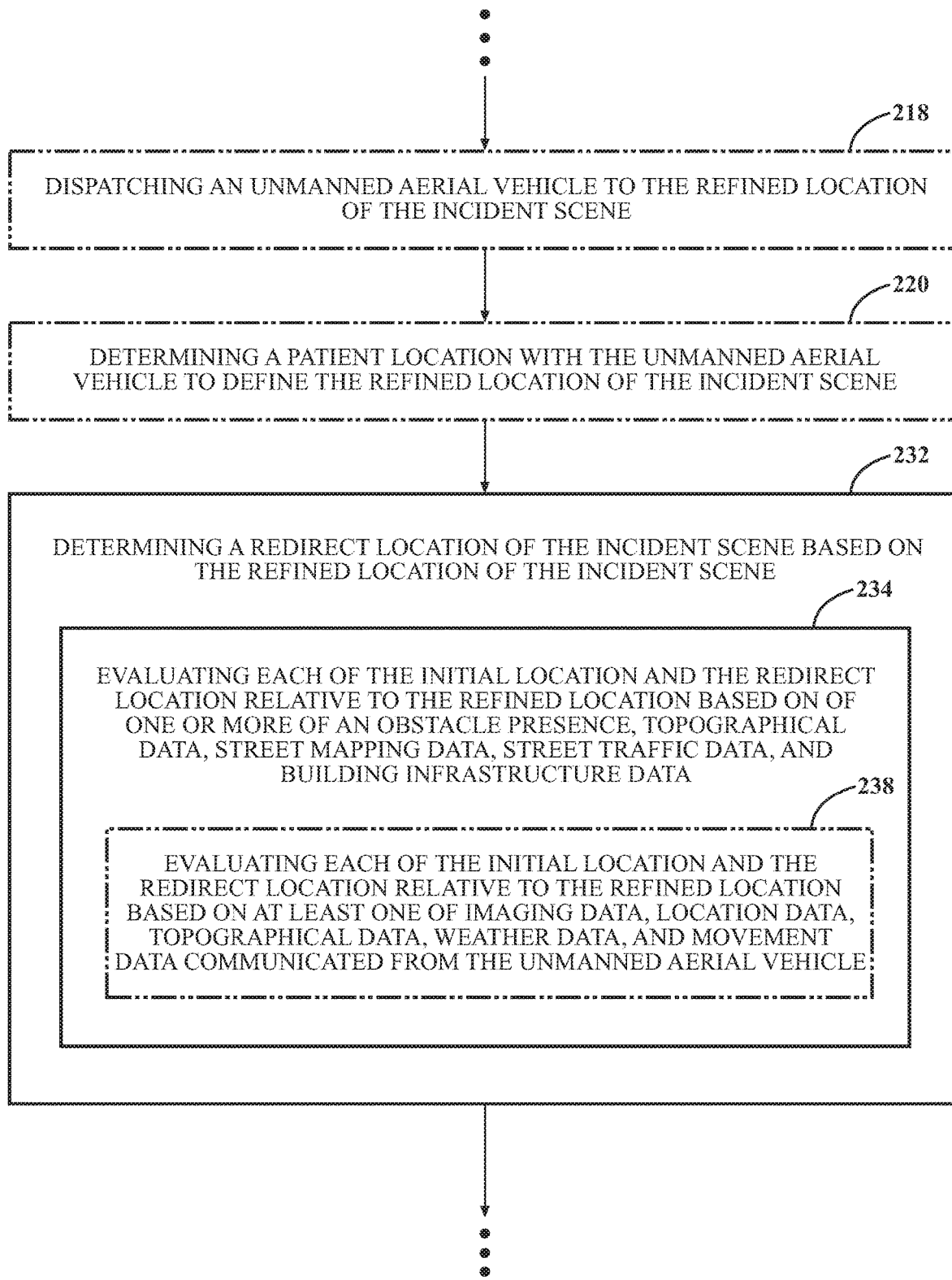

To illustrate the embodiment where the method 210 includes the step 232 of determining the redirect location of the incident scene 136, FIG. 7L illustrates an embodiment where the incident scene occurs in a backyard of a home with a river 236. As shown in FIG. 7L, the ambulance 91 is dispatched to the home with the address 1236 Main St. by the remote dispatch center 126.

Figure 7N:
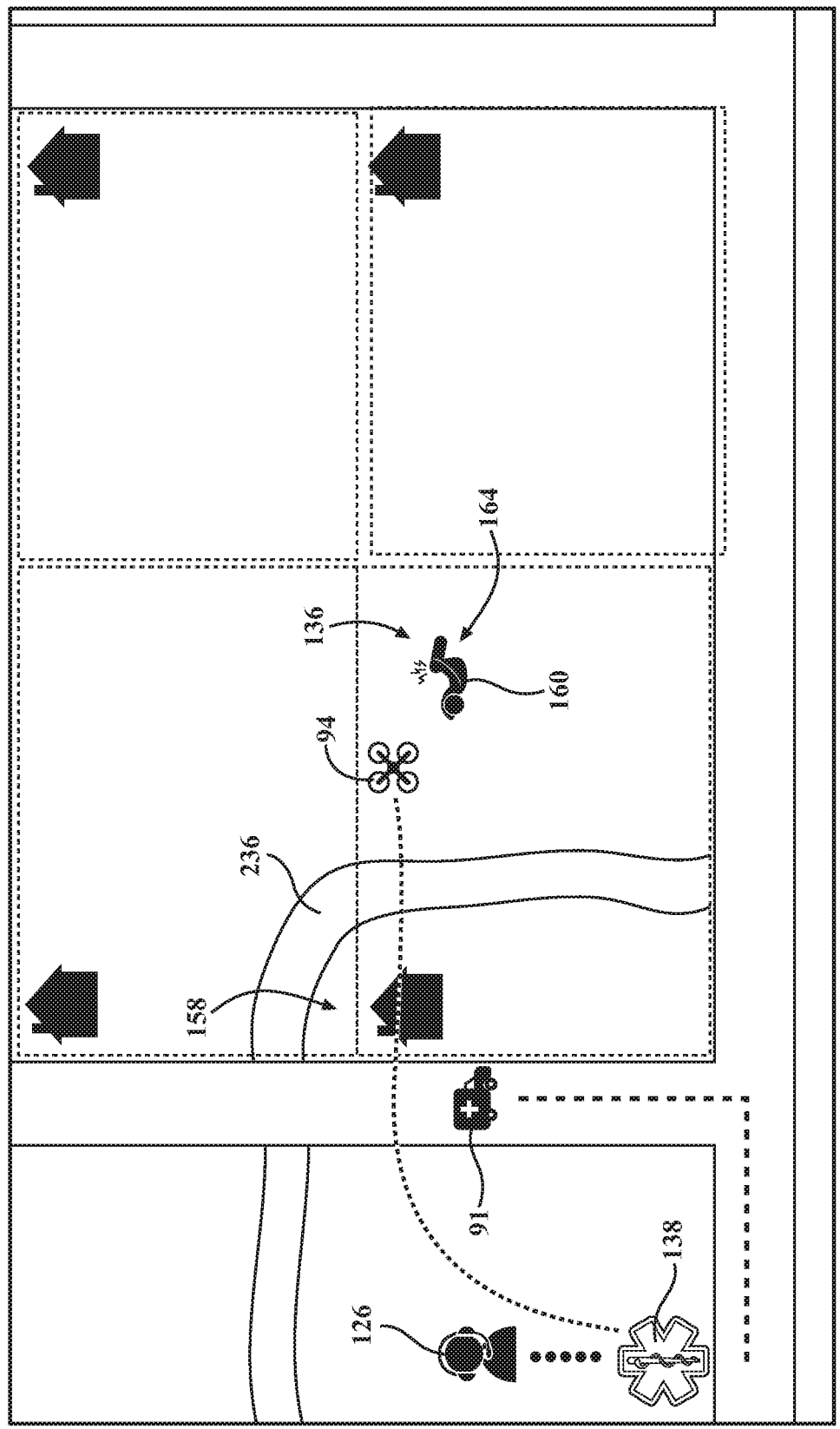
Figure 70:
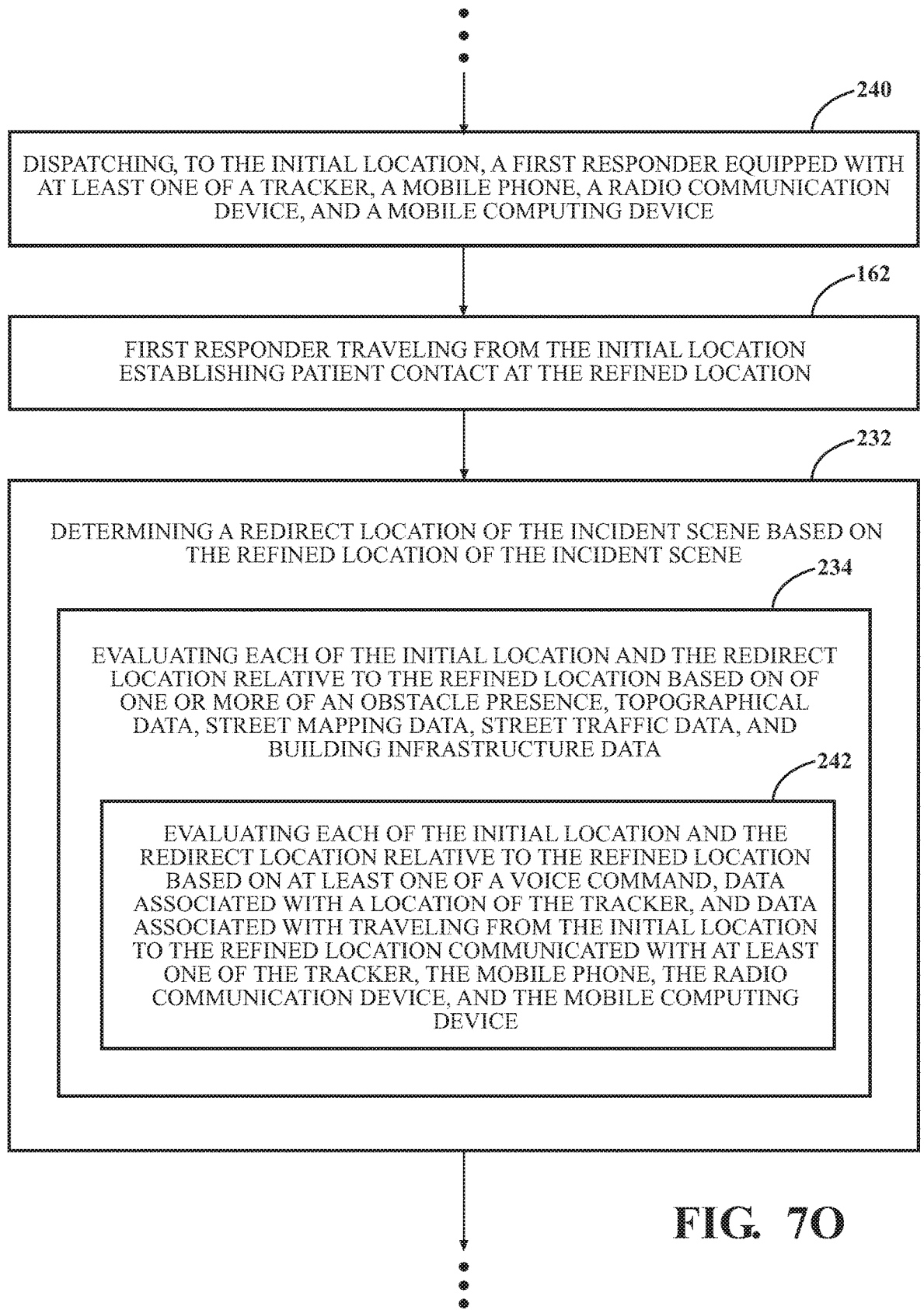

In an embodiment shown in FIG. 7M and FIG. 7N, the method 210 may include an instance of the step 218 where the unmanned aerial vehicle 94 is dispatched to the refined location 164, and the step 220 where the unmanned aerial vehicle 94 determines the patient location to define the refined location 164. The unmanned aerial vehicle 94 may then communicate the refined location 164 to the navigation system 86 during step 112'. The navigation system 86 may then determine, during a step 232 and step 234, the redirect location based on the refined location 164. In the embodiment of FIG. 7M, the step 234 may include a step 238 of evaluating each of the initial location 158 and the redirect location relative to the refined location 164 based on at least one of imaging data, location data, weather data, and movement data communicated from the unmanned aerial vehicle 94. For example, the unmanned aerial vehicle 94 of FIG. 7N may communicate imaging data of the river 236. Accordingly, during step 232, the navigation system 86 may determine the redirect location based on the imaging data of the river 236.

Figure 7P:
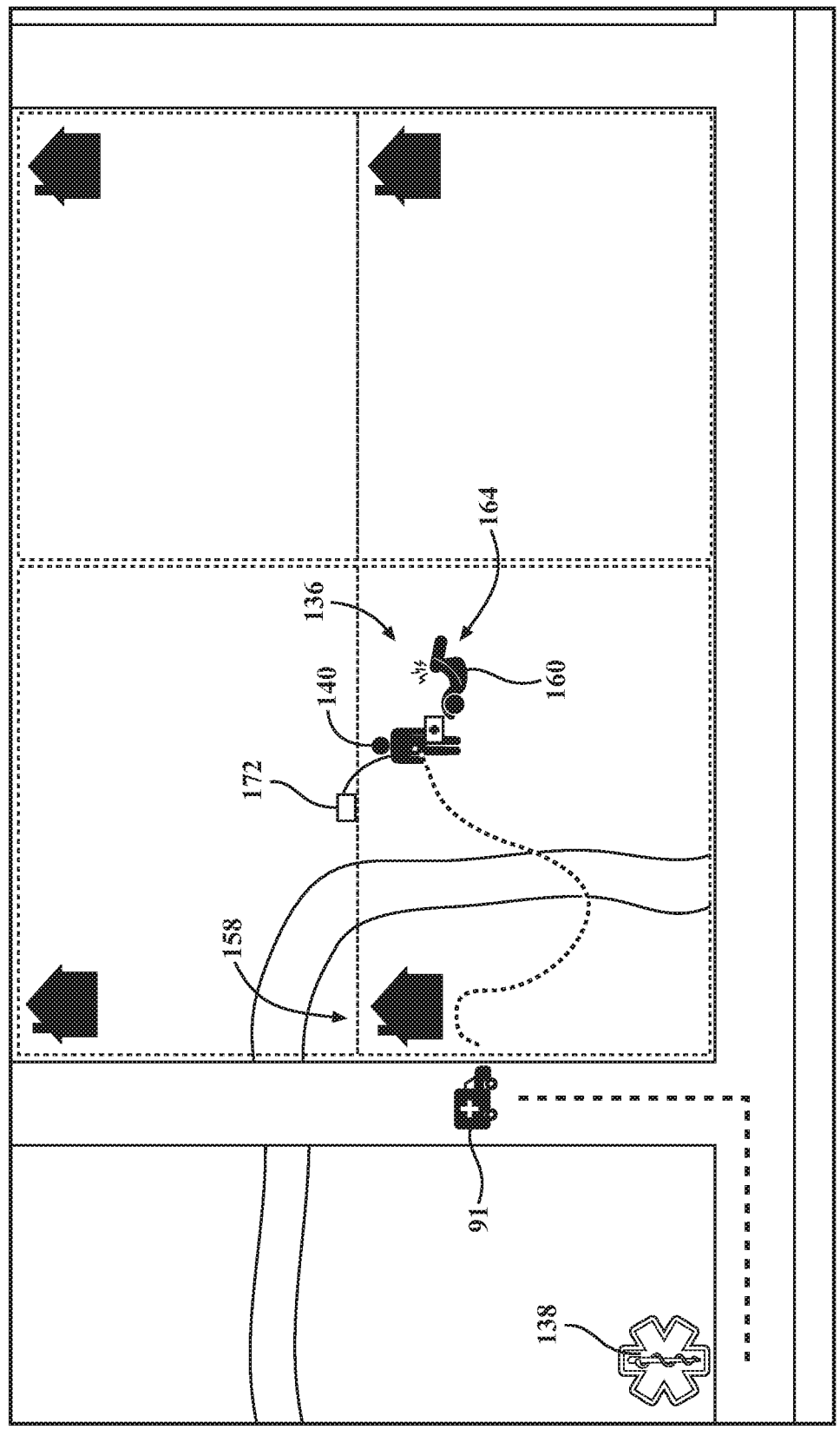

In an embodiment of FIGS. 7O and 7P, the method 210 may include a step 240 of dispatching, to the initial location 158, the first responder 140 equipped with at least one of the tracker 172, the mobile phone 120M, the radio communication device 120R, and the mobile computing device. The method 210 also includes the step 162 of establishing patient contact at the refined location 164 with the first responder 140. The navigation system 86 may then determine, during step 232 and step 234, the redirect location based on the refined location 164. In the embodiment of FIG. 7O, the step 234 may include a step 242 of evaluating each of the initial location 158 and the redirect location relative to the refined location 164 based on at least one of a voice command VC, data associated with a location of the tracker 172, and data associated with traveling from the initial location 158 to the refined location 164 communicated with at least one of the tracker 172, the mobile phone 120M, the radio communication device 120R, and the mobile computing device.

For example, in the embodiment of FIG. 7P, the first responder 140 equipped with the tracker 172 travels to the refined location 164. Accordingly, the navigation system 86 may determine the redirect location after evaluating each of the initial location 158 and the redirect location relative to the refined location 164 based on data D1 associated with the location of the tracker 172 and/or data associated with traveling from the initial location 158 to the refined location 164. In one instance, the first responder 140 may cross the river 236 and notify the navigation system 86 of the location of the river 236 and that the navigation system 86 should determine a redirect location because, for example, the first responder 140 recognizes that the autonomous patient support apparatus 20 will be unable to traverse the river 236.

Figure 7Q:
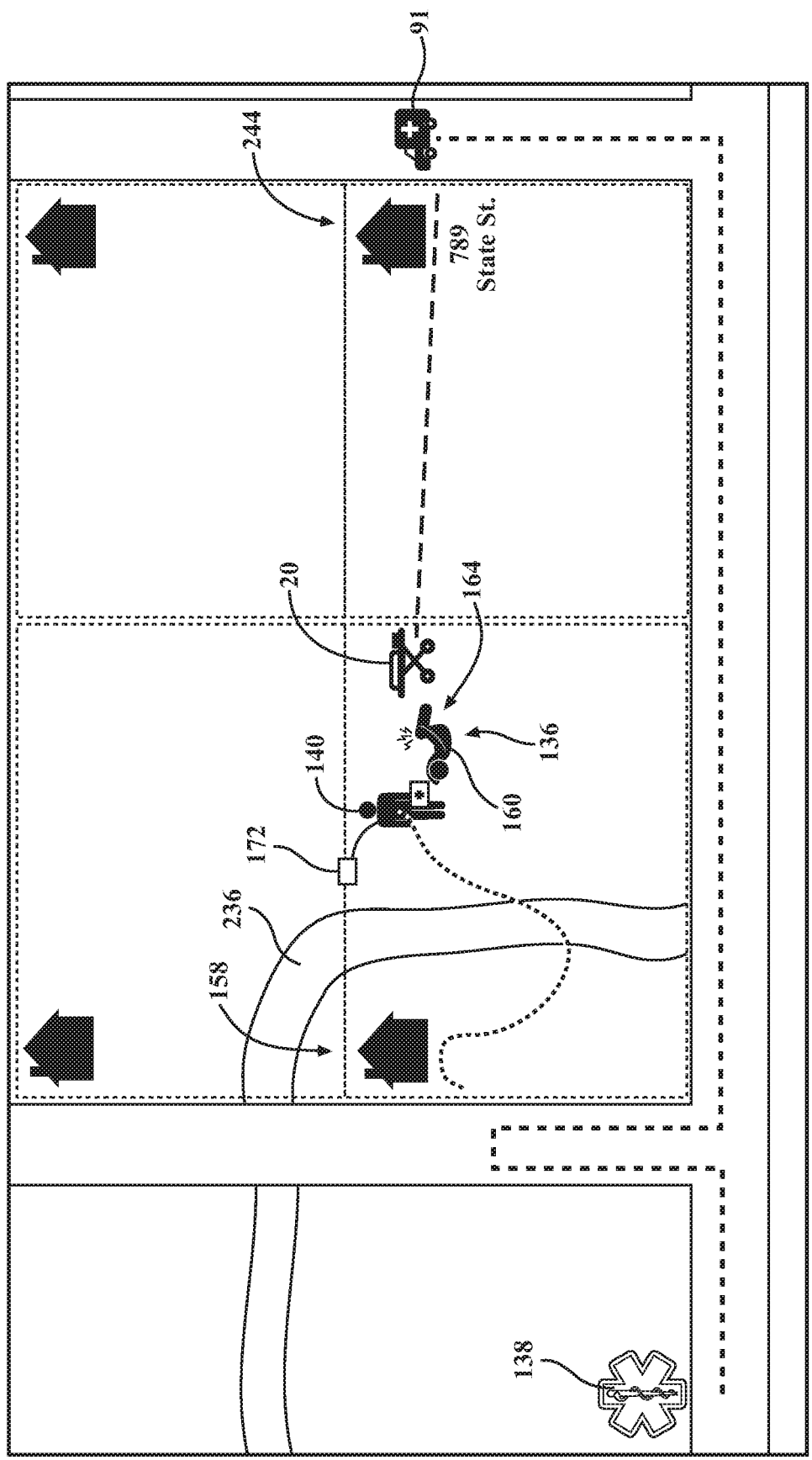

In the embodiment of FIGS. 7K and 7Q, after the method 210 determines the redirect location during step 232, the method 210 proceeds to an instance of the step 108 of unloading the autonomous patient support apparatus 20. However, in this instance, the autonomous patient support apparatus 20 is unloaded at the redirect location 244 instead of the initial location 158. As shown in FIG. 7Q, the ambulance 91 travels to the redirect location 244, a home associated with an address 789 State St., and unloads the autonomous patient support apparatus 20 there. The controller 93 then controls the drive system 84 to drive the autonomous patient support apparatus 20 to the refined location 164 from the redirect location 244.

Figure 7R:
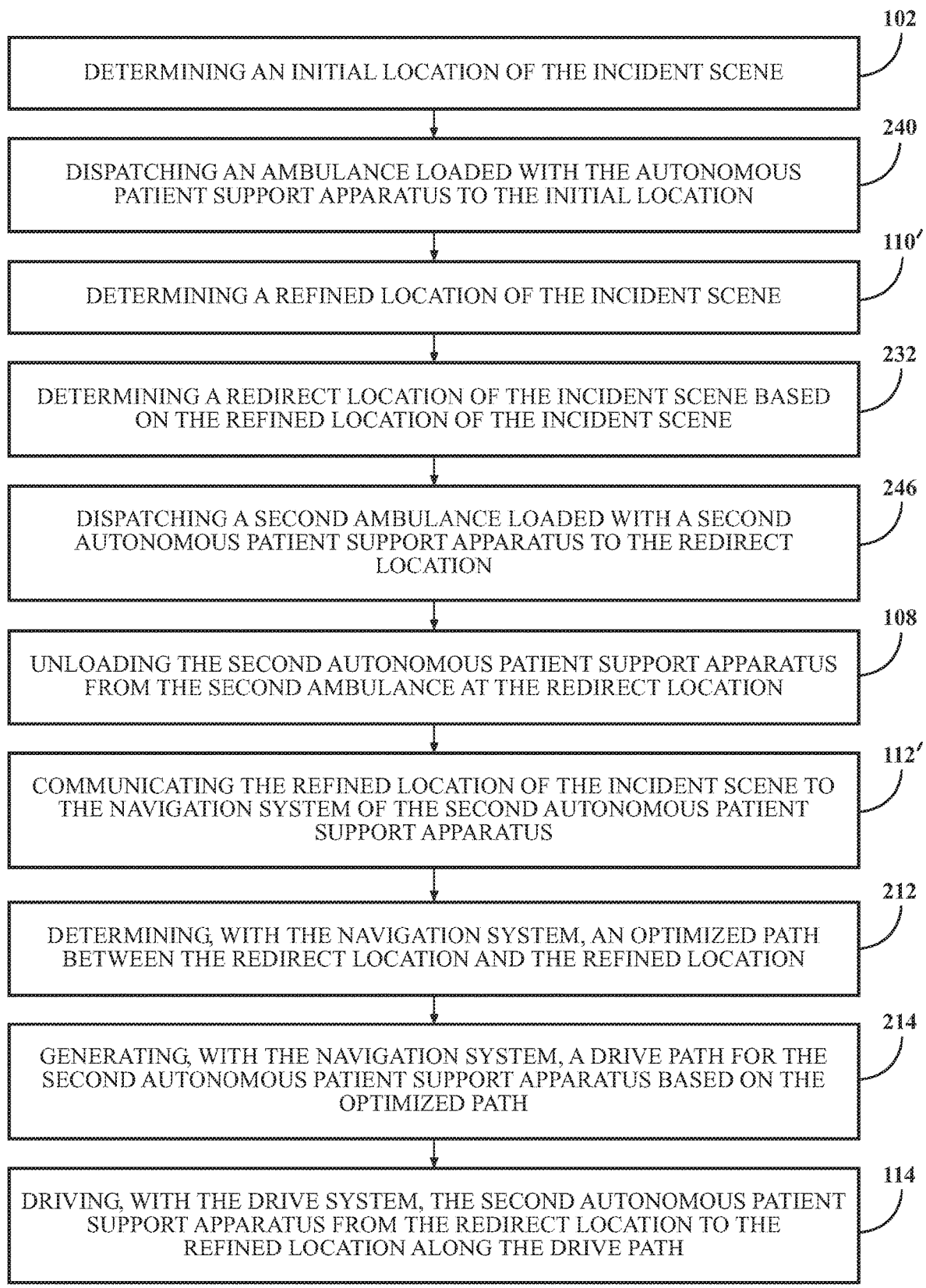
Figure 7S:
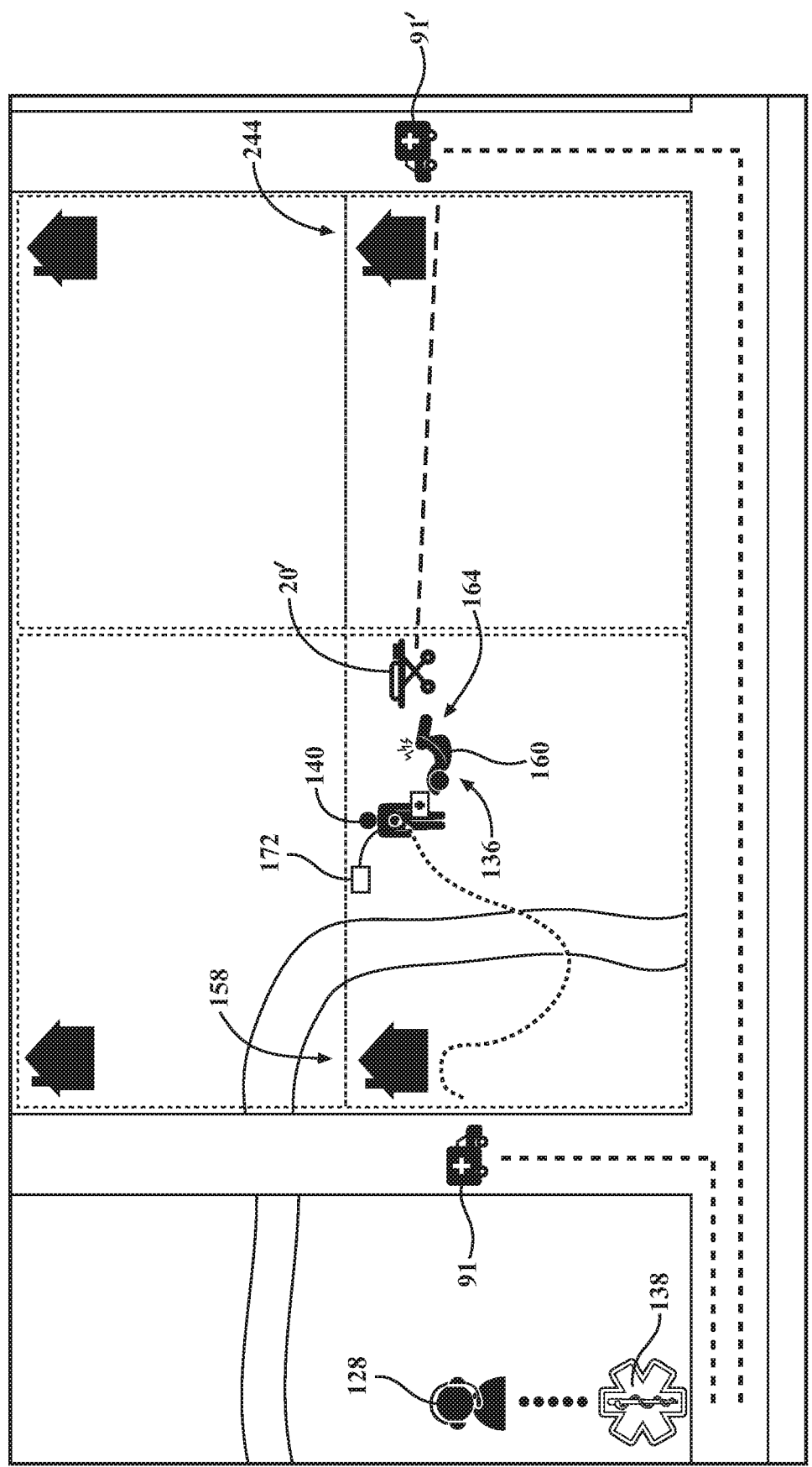

In the embodiment of FIGS. 7R and 7S, the method 210 includes a step 246 of dispatching a second ambulance 91' loaded with a second autonomous patient support apparatus 20' to the redirect location 244. To drive the second ambulance 91' to the refined location 164, the method 210 also includes an instance of the step 108 of unloading the second autonomous patient support apparatus 20' from the second ambulance 91' at the redirect location 244; an instance of the step 112' where the refined location 164 is communicated to the navigation system 86 of the second autonomous patient support apparatus 20'; an instance of the steps 212 and 214 where the navigation system 86 determines the optimized path and generates a drive path for the second autonomous patient support apparatus 20'; and an instance of the step 114 where the drive system 84 drives the second autonomous patient support apparatus 20' from the redirect location 244 to the refined location 164. As shown in FIG. 7S, the second ambulance 91' is dispatched by the remote dispatch center 126 to the redirect location 244. The second autonomous patient support apparatus 20' is then unloaded from the second ambulance 91' and drives to the refined location 164.

Figure 8A:
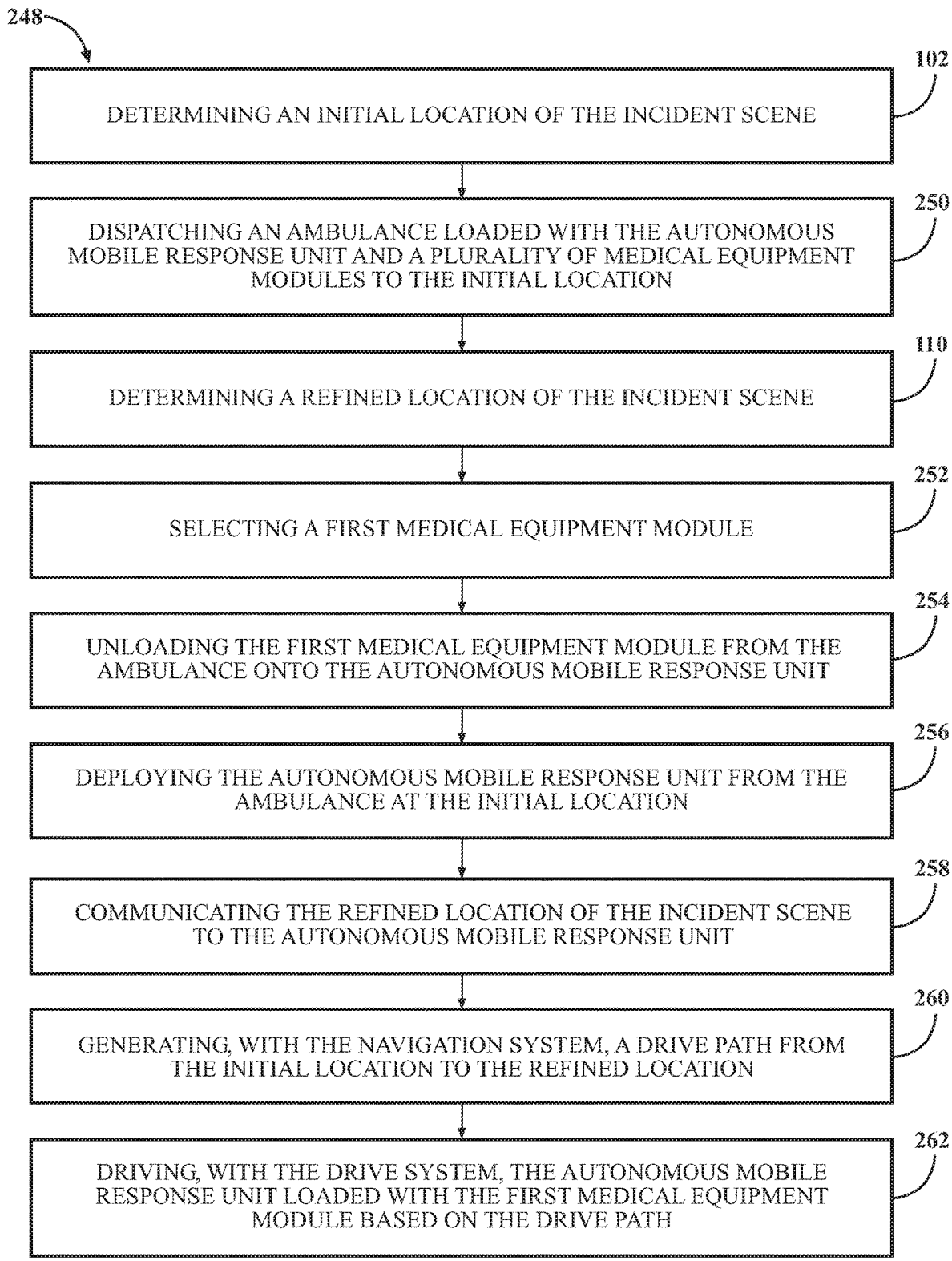
FIG. 8A is a diagrammatic view of a method of transporting medical equipment to the incident scene with an autonomous mobile response unit.

FIG. 8A illustrates a method 248 of transporting medical equipment modules 96, such as a trauma kit, a drug box, an O$_2$ bottle, a defibrillator, and/or a heart monitor, to an incident scene. As shown, the method 210 includes the above-described step 102 of determining the initial location 158 of the incident scene 136 and the above-described step 110 of determining the refined location 164 of the incident scene 136.

The method 248 also includes a step 250 of dispatching an ambulance 91 loaded with the autonomous mobile response unit and a plurality of medical equipment modules 96 to the initial location 158; a step 252 of selecting a first medical equipment module, such as one of the medical equipment modules 96 shown in FIG. 1 or the medical equipment module 96 shown in FIG. 5; a step 254 of dispensing the first medical equipment module 96 from the ambulance 91 onto the autonomous mobile response unit; a step 256 of deploying the autonomous mobile response unit from the ambulance 91 at the initial location 158; a step 258 of communicating the refined location 164 of the incident scene 136 to the autonomous mobile response unit; a step 260 of generating, with the navigation system 86, a drive path 186 from the initial location 158 to the refined location 164; and a step 262 of driving, with the drive system 84, the autonomous mobile response unit loaded with the first medical equipment module 96 based on the drive path 186.

Figure 8B:
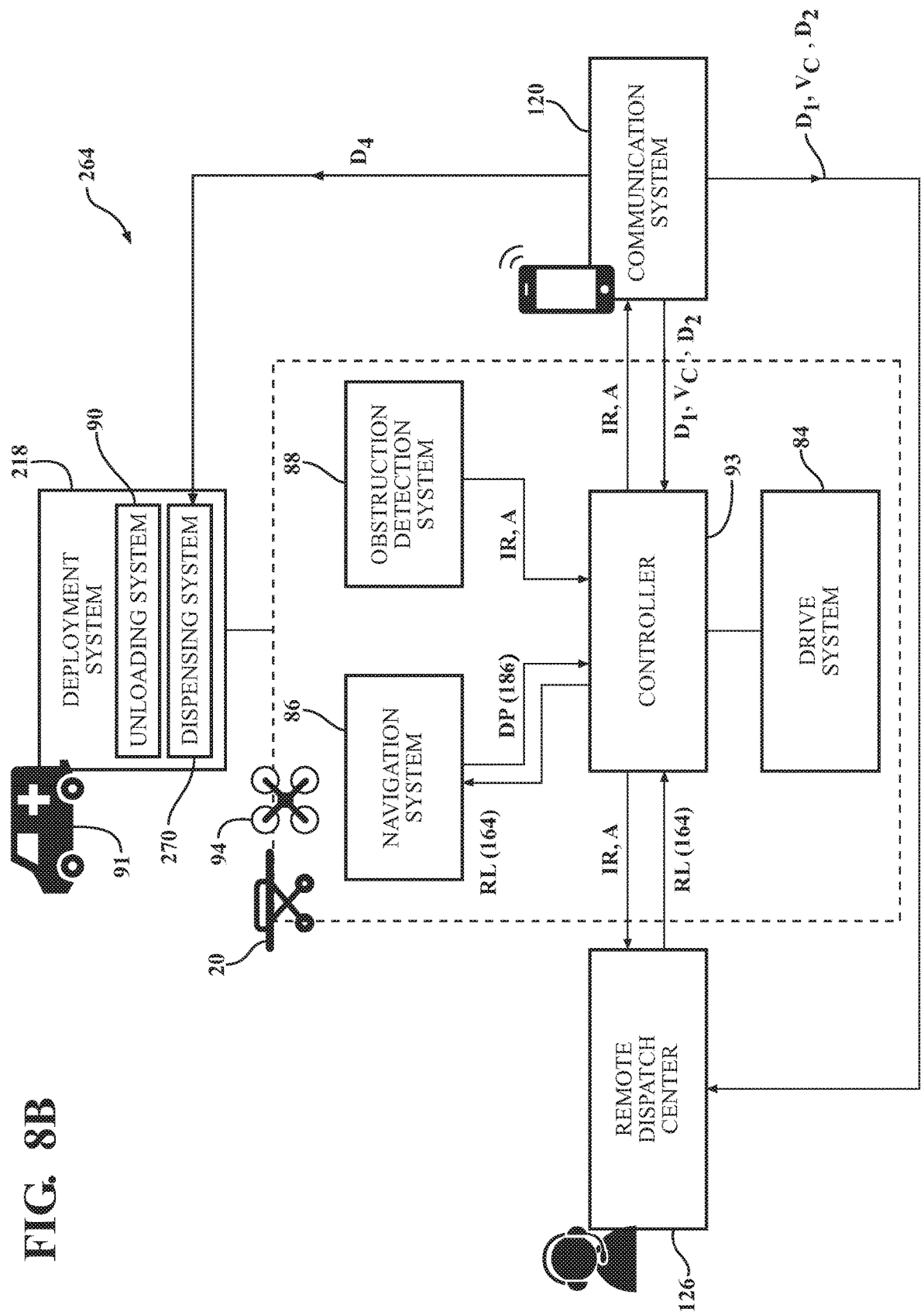
FIG. 8B is a schematic view of a system for transporting medical equipment to the incident scene with the autonomous mobile response unit.

As shown in FIG. 8B, the steps 102, 110, and 250-262 may be executed by components of a system 264 for transporting medical equipment modules 96 to an incident scene 136. As previously stated, the autonomous mobile response unit may include the autonomous patient support apparatus 20 and/or the unmanned aerial vehicle 94. As shown in FIG. 8B, the autonomous patient support apparatus 20 and the unmanned aerial vehicle 94 may include the navigation system 86, the drive system 84, the controller 93, and the obstruction detection system 88.

The system 264 may also include a dispensing system 270 configured to dispense medical equipment modules 96 from the ambulance 91 onto the autonomous mobile response unit. For example, in an embodiment where the autonomous mobile response unit is the unmanned aerial vehicle 94, the dispensing system 270 may dispense a medical equipment module 96 into the retaining system 98 (see FIG. 5) of the unmanned aerial vehicle 94. In an embodiment where the autonomous mobile response unit is the autonomous patient support apparatus 20, a medical equipment module 96 may be dispensed onto and affixed to the patient support surface 50 (see FIG. 5) of the autonomous patient support apparatus 20. The dispensing system 270 may be operated manually or autonomously. For example, a first responder 140 may activate the dispensing system 270 by physically depressing a button. In another example, the dispensing system 270 may dispense a medical equipment module 96 after receiving an input from a remote computing device.

As shown, the system 264 may also include components of the above-described system 216. However, the system 264 may omit the second communication system 122, which is included in systems 118, 216. In some embodiments, components of the system 264 may be omitted.

Figure 8C:
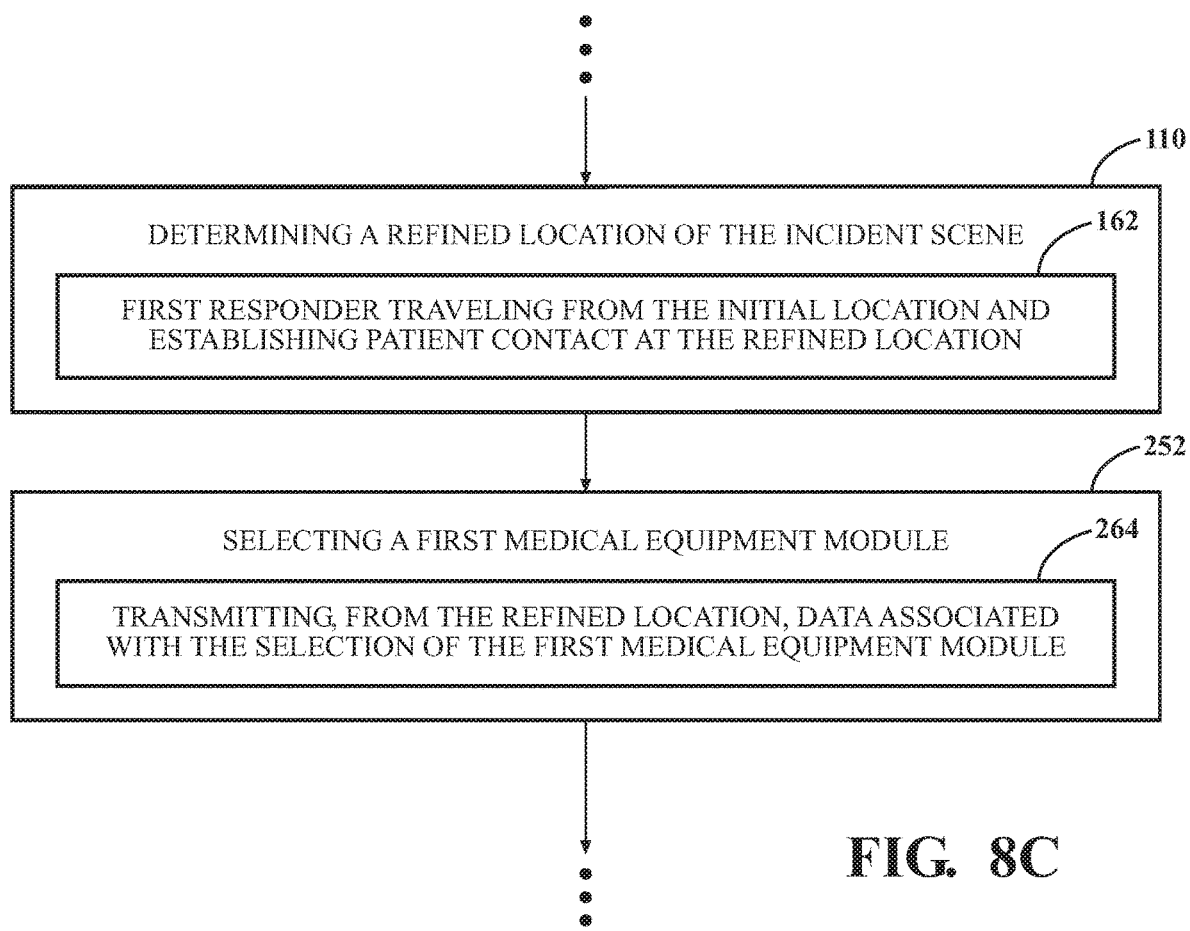
FIGS. 8C-8F are diagrammatic views of embodiments of the method of transporting medical equipment to the incident scene with the autonomous mobile response unit.

FIG. 8C further illustrates the step 252 of selecting a first medical equipment module 96. As shown, the step 252 may include a step 264 of transmitting from the refined location 164, with the communication system 120, data D4 associated with the selection of the first medical equipment module 96. In such embodiments, the first responder 140 travels to the refined location 164 during step 162 and, after evaluating the patient's 160 condition, determines types of equipment that are needed. The first responder 140 then selects the first medical equipment module 96 accordingly using the communication system 120.

Figure 8D:
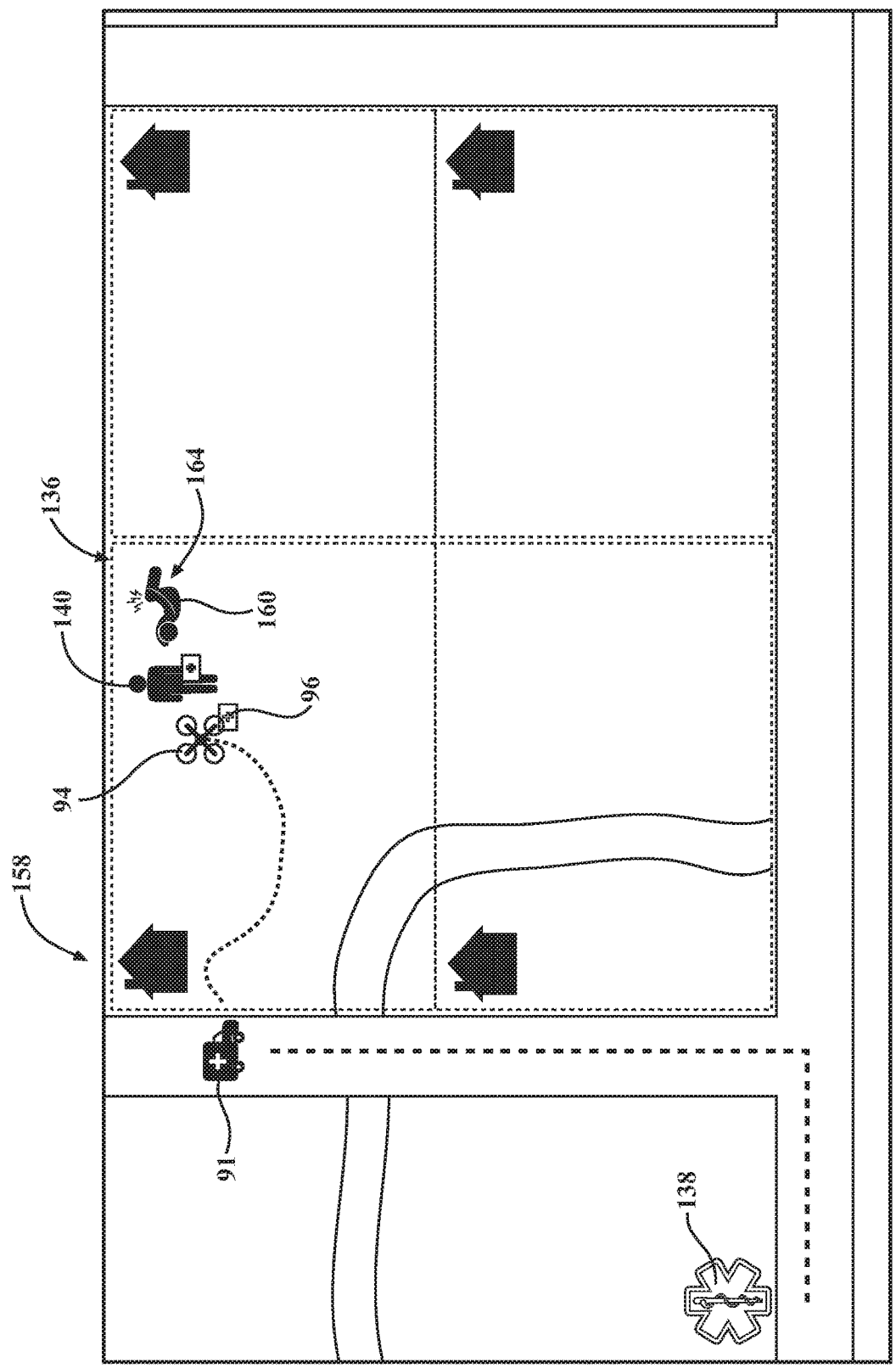

FIG. 8D illustrates an embodiment where the autonomous mobile response unit is the unmanned aerial vehicle 94 and the method 248 includes the step 252 of selecting the first medical equipment module 96. As shown, the first responder 140 travels to the refined location 164 during step 110. The first responder 140 then selects the first medical equipment module 96 during step 252 by transmitting, from the refined location 164, data D4 associated with the selection of the first medical equipment module 96. After the first medical equipment module 96 is dispensed onto the unmanned aerial vehicle 94 by the dispensing system 270 during step 254, the unmanned aerial vehicle 94 is deployed from the ambulance 91 during step 256, receives the refined location 164 during step 258, generates a drive path 186 during step 260, and drives to the refined location 164 during step 262. As such, the first medical equipment module 96 is transported to the incident scene 136.

Figure 8E:
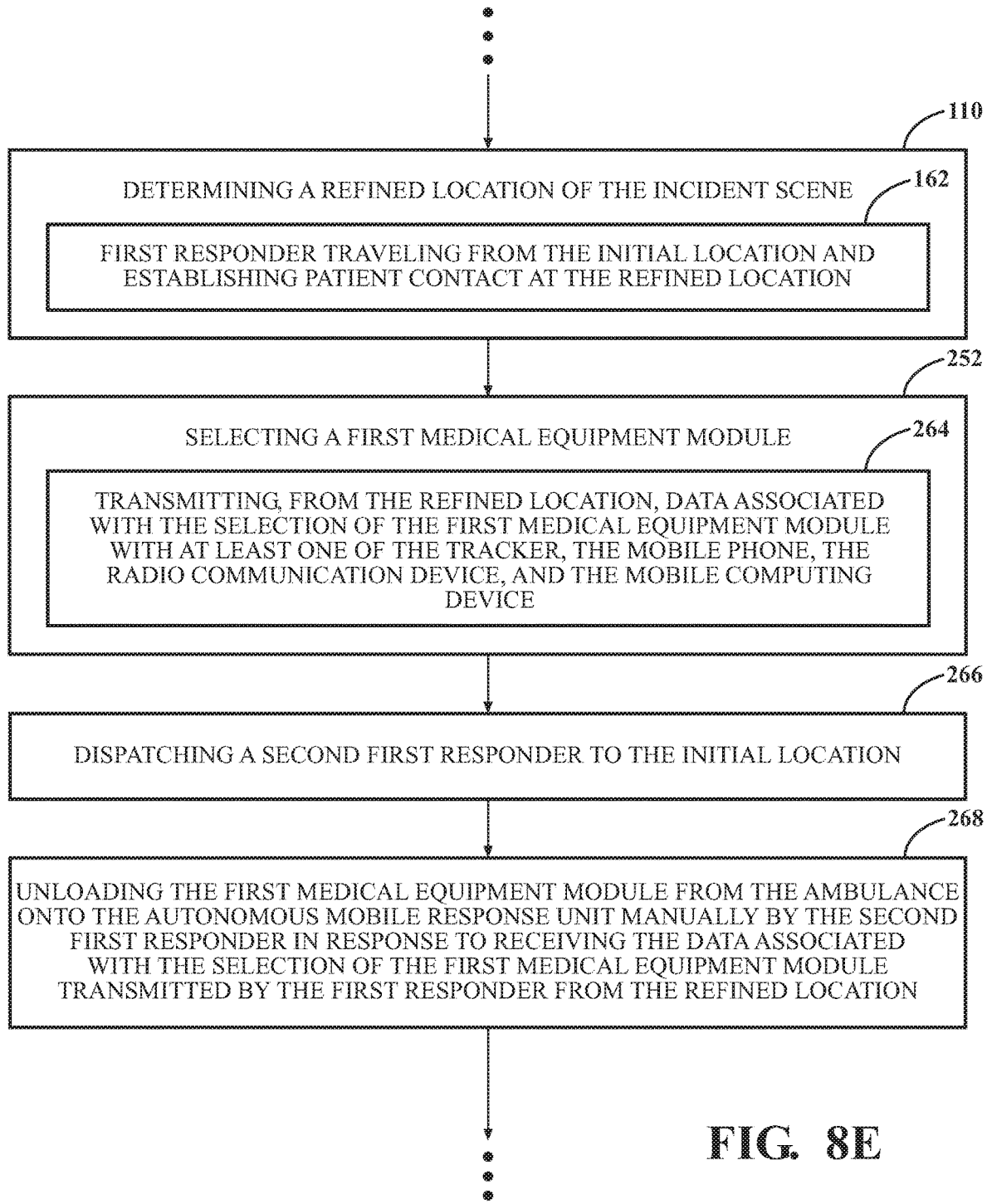
Figure 8F:
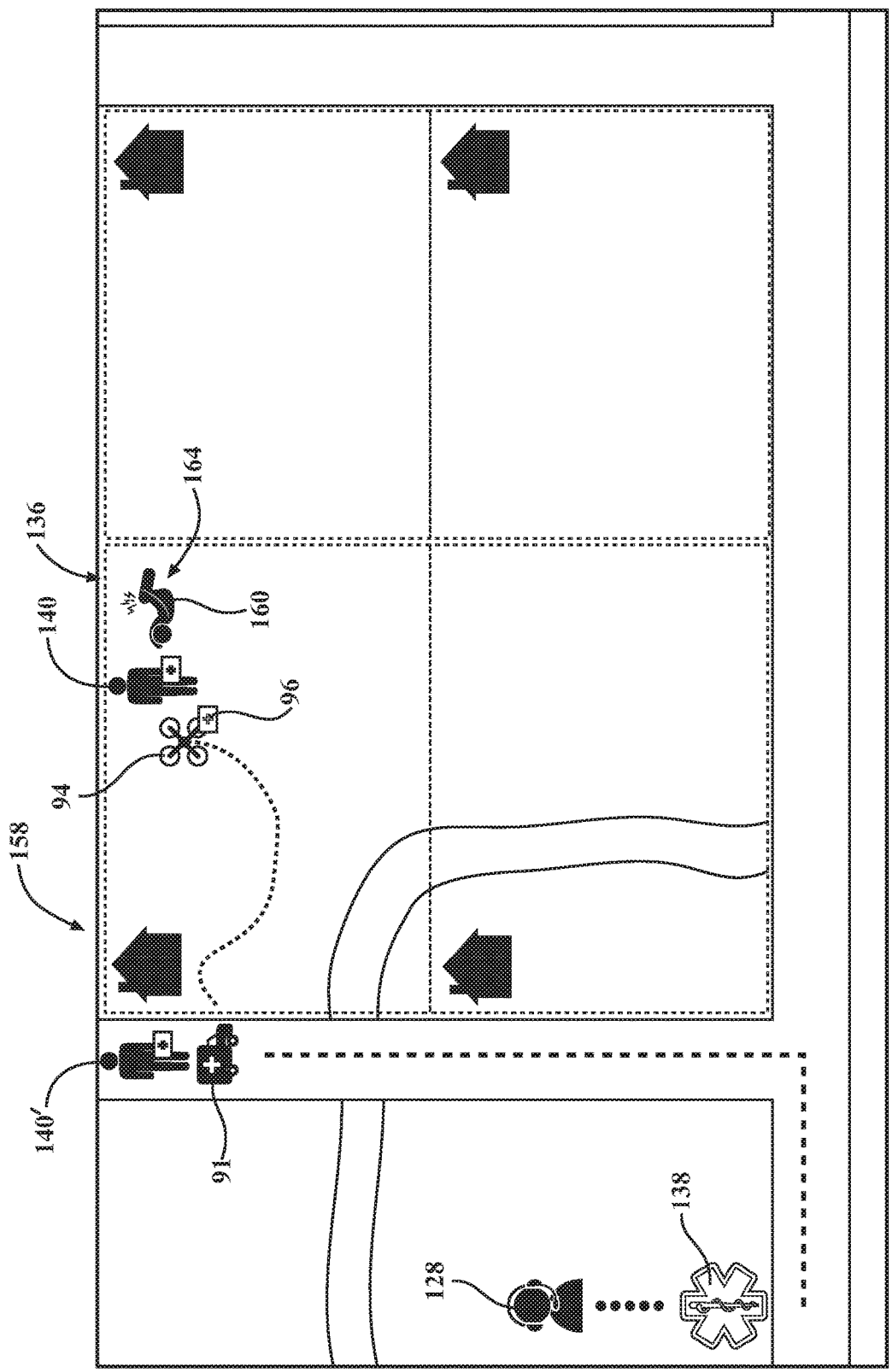

FIG. 8E illustrates an embodiment where the method 248 includes a step 266 of dispatching a second first responder 140' (shown in FIG. 8F) to the initial location 158 and a step 268 of manually dispensing the first medical equipment module 96 from the ambulance 91 onto the autonomous mobile response unit with the second first responder 140' in response to receiving the data D4 associated with the selection of the first medical equipment module 96 transmitted by the first responder 140 from the refined location 164. FIG. 8F further illustrates this embodiment. In FIG. 8F, the first responder 140 has traveled to the refined location 164 and has selected the first medical equipment module 96 during step 252. As shown, the second first responder 140' is then dispatched to the initial location 158 during step 266 and manually dispenses the first medical equipment module 96 from the ambulance 91 onto the unmanned aerial vehicle 94 using the dispensing system 270. The unmanned aerial vehicle 94 then drives to the refined location 164, providing the first responder 140 with the first medical equipment module 96.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A system comprising:
an autonomous patient support apparatus including a navigation system, a base supporting a plurality of caster wheels, a support frame disposed above the base, a patient support surface coupled to the support frame for supporting a patient, a lift mechanism to move the support frame relative to the base between a plurality of vertical configurations, and a drive system fixed to the base and having at least one auxiliary wheel arranged between the plurality of caster wheels to drive the autonomous patient support apparatus;
a remote dispatch center configured to:
dispatch a first responder to an initial location of an incident scene, and
dispatch an ambulance loaded with the autonomous patient support apparatus to the initial location;
an unloading system configured to unload the autonomous patient support apparatus from the ambulance at the initial location, the unloading system including a trolley and a track, wherein the patient support apparatus is configured to couple to the trolley and the trolley is configured to move along the track; and
a communication system configured to communicate a refined location of the incident scene to the navigation system of the autonomous patient support apparatus; and
wherein the navigation system of the autonomous patient support apparatus is configured to generate a drive path between the initial location and the refined location for the drive system to drive the autonomous patient support apparatus along from the initial location to the refined location with the at least one auxiliary wheel.

2. The system as set forth in claim 1, wherein the communication system is further defined as a first communication system and wherein the system further comprises a second communication system configured to receive an emergency call at a public safety answering point.

3. The system as set forth in claim 2, wherein the second communication system is further configured to relay the initial location from the public safety answering point to the remote dispatch center in communication with the navigation system of the autonomous patient support apparatus.

4. The system as set forth in claim 1, wherein the communication system comprises at least one of a radio communication device and a mobile phone, the at least one of the radio communication device and the mobile phone being configured to transmit a voice command to communicate the refined location of the incident scene to the navigation system.

5. The system as set forth in claim 4, wherein the at least one of the radio communication device and the mobile phone is further configured to transmit the voice command to a remote dispatch center.

6. The system as set forth in claim 1, further comprising a tracker equipped to the first responder, the tracker being configured to determine the refined location of the incident scene based on the first responder traveling from the initial location and establishing patient contact at the refined location.

7. The system as set forth in claim 6, wherein the tracker comprises at least one of a GPS tracker configured to determine the location of the tracker based on a GPS signal, a cellular tracker configured to determine the location of the tracker based on a cellular signal, and a WiFi tracker configured to determine the location of the tracker based on a WiFi signal.

8. The system as set forth in claim 6, wherein the communication system comprises a mobile computing device, wherein the tracker is coupled to the mobile computing device, and wherein the mobile computing device is configured to transmit data associated with a location of the tracker to the navigation system of the autonomous patient support apparatus.

9. The system as set forth in claim 8, wherein the mobile computing device is further configured to transmit the data associated with the location of the tracker to the navigation system of the autonomous patient support apparatus via the remote dispatch center.

10. The system as set forth in claim 6, wherein the communication system comprises the tracker, and wherein the tracker comprises a tracker user interface configured to transmit data associated with a location of the tracker to the navigation system of the autonomous patient support apparatus in response to being actuated.

11. The system as set forth in claim 10, wherein the tracker user interface is further configured to transmit data to the navigation system of the autonomous patient support apparatus via the remote dispatch center.

12. The system as set forth in claim 6, wherein the tracker is further configured to generate a tracker path based on movement of the first responder away from the initial location, the tracker path comprising a plurality of locations associated with the tracker.

13. The system as set forth in claim 12, wherein the navigation system is further configured to:
   generate the drive path based on the tracker path generated based on the movement of the first responder; and
   navigate the drive system based on the drive path.

14. The system as set forth in claim 1, wherein the navigation system is further configured to navigate the drive system based on the drive path.

15. The system as set forth in claim 1, wherein the system further comprises:
   an obstruction detection system configured to:
      detect a presence of an obstruction at an obstruction location; and
      interrupt operation of the drive system in response to detecting the obstruction at the obstruction location.

16. The system as set forth in claim 15, wherein the navigation system is further configured to generate, with the navigation system, an alternate drive path for the autonomous patient support apparatus between the obstruction location and the refined location; and
   wherein the drive system is further configured to drive the autonomous patient support apparatus from the obstruction location to the refined location along the alternate drive path.

17. The system as set forth in claim 15, wherein the obstruction detection system is further configured to:
   determine that the autonomous patient support apparatus cannot reach the refined location with the drive system; and
   generate an alarm with the autonomous patient support apparatus to indicate that the obstruction cannot be traversed without intervention.

18. The system as set forth in claim 15, wherein the obstruction detection system is further configured to communicate an intervention request related to the presence of the obstruction to at least one of the remote dispatch center and the first responder; and
   wherein the drive system is further configured to drive the autonomous patient support apparatus from the obstruction location to the refined location along the drive path after the obstruction communicated via the intervention request is rectified.

* * * * *